(12) United States Patent
Sullivan et al.

(10) Patent No.: US 11,045,217 B2
(45) Date of Patent: *Jun. 29, 2021

(54) UTERINE FIBROID TISSUE REMOVAL DEVICE

(71) Applicant: HOLOGIC, INC., Marlborough, MA (US)

(72) Inventors: Roy Hewitt Sullivan, Marlborough, MA (US); Albert Chun-Chi Chin, Marlborough, MA (US); Eric Karl Litscher, Marlborough, MA (US); William Lucas Churchill, Marlborough, MA (US); Ronald David Adams, Marlborough, MA (US); William Harwick Gruber, Marlborough, MA (US); David Jacobs, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 169 days.

This patent is subject to a terminal disclaimer.

(21) Appl. No.: 16/190,770

(22) Filed: Nov. 14, 2018

(65) Prior Publication Data

US 2019/0183528 A1 Jun. 20, 2019

Related U.S. Application Data

(63) Continuation of application No. 15/365,502, filed on Nov. 30, 2016, now Pat. No. 10,130,389, which is a (Continued)

(51) Int. Cl.
*A61B 17/32* (2006.01)
*A61B 17/42* (2006.01)
(Continued)

(52) U.S. Cl.
CPC .. *A61B 17/32002* (2013.01); *A61B 17/00234* (2013.01); *A61B 17/3205* (2013.01);
(Continued)

(58) Field of Classification Search
CPC ...... A61B 17/320016; A61B 17/32002; A61B 17/320783; A61B 17/3205; A61B 17/3207; A61B 17/32004; A61B 2017/320004
See application file for complete search history.

(56) References Cited

U.S. PATENT DOCUMENTS 2,708,437 A 5/1955 Hutchins
2,849,002 A 8/1958 Oddo et al.
(Continued)

FOREIGN PATENT DOCUMENTS

EP 0010650 5/1980
EP 0044877 2/1982
(Continued)

OTHER PUBLICATIONS

Decision of Rejection for Chinese Patent Application No. 201610066887.3, dated Jun. 10, 2019, with partial translation in English prepared by foreign associate.
(Continued)

*Primary Examiner* — Sarah A Simpson
(74) *Attorney, Agent, or Firm* — Vista IP Law Group, LLP

(57) ABSTRACT

A uterine fibroid tissue removal device includes an inner tube disposed within an outer tube and configured to be translated and rotated relative to the outer tube, and a separately formed unitary distal tip member attached to a distal end of the inner tube, such that the distal tip member translates and rotates relative to the outer tube along with the inner tube, wherein a distal facing open cutting end of the
(Continued)

distal tip member in fluid communication with an axial lumen of the distal tip member translates across a tissue resection window in a sidewall of the outer tube so as to sever tissue extending therethrough, the distal tip member axial lumen being in fluid communication with an axial lumen of the inner tube, wherein an outer diameter of the distal tip member is greater than an outer diameter of the inner tube.

19 Claims, 44 Drawing Sheets

Related U.S. Application Data continuation of application No. 14/983,024, filed on Dec. 29, 2015, now Pat. No. 9,539,019, which is a continuation of application No. 14/680,276, filed on Apr. 7, 2015, now Pat. No. 9,339,288, which is a continuation of application No. 12/432,686, filed on Apr. 29, 2009, now Pat. No. 9,095,366.

(51) Int. Cl.
| | | |
|---|---|---|
| *A61B 17/3205* | (2006.01) | |
| *A61M 1/00* | (2006.01) | |
| *A61B 17/00* | (2006.01) | |
| *A61B 17/34* | (2006.01) | |
| *A61B 17/3201* | (2006.01) | |
| *A61B 17/3207* | (2006.01) | |
| *A61B 17/29* | (2006.01) | |
| *A61B 18/14* | (2006.01) | |
| *A61B 17/22* | (2006.01) | |

(52) U.S. Cl.
CPC ......... *A61B 17/320016* (2013.01); *A61B 17/32053* (2013.01); *A61B 17/3415* (2013.01); *A61B 17/42* (2013.01); *A61M 1/0082* (2014.02); *A61B 17/3201* (2013.01); *A61B 17/32056* (2013.01); *A61B 17/320725* (2013.01); *A61B 17/320783* (2013.01); *A61B 17/3462* (2013.01); *A61B 2017/0046* (2013.01); *A61B 2017/0073* (2013.01); *A61B 2017/00331* (2013.01); *A61B 2017/00398* (2013.01); *A61B 2017/00424* (2013.01); *A61B 2017/00526* (2013.01); *A61B 2017/00685* (2013.01); *A61B 2017/22078* (2013.01); *A61B 2017/22079* (2013.01); *A61B 2017/2905* (2013.01); *A61B 2017/320004* (2013.01); *A61B 2017/320024* (2013.01); *A61B 2017/320028* (2013.01); *A61B 2017/320064* (2013.01); *A61B 2017/320775* (2013.01); *A61B 2017/347* (2013.01); *A61B 2017/3466* (2013.01); *A61B 2017/4216* (2013.01); *A61B 2018/1407* (2013.01); *A61B 2217/005* (2013.01); *A61B 2217/007* (2013.01)

(56) References Cited

U.S. PATENT DOCUMENTS

| | | | |
|---|---|---|---|
| 3,369,034 | A | 2/1968 | Chalmers et al. |
| 3,561,429 | A | 2/1971 | Jewett |
| 4,040,311 | A | 8/1977 | Page, Jr. et al. |
| 4,188,952 | A | 2/1980 | Loschilov et al. |
| 4,198,981 | A | 4/1980 | Sinnreich |
| 4,203,444 | A | 5/1980 | Bonnell et al. |
| 4,246,902 | A | 1/1981 | Martinez |
| 4,261,360 | A | 4/1981 | Perez |
| 4,316,465 | A | 2/1982 | Dotson, Jr. |
| 4,598,698 | A | 7/1986 | Siegmund |
| 4,598,710 | A | 7/1986 | Klienberg et al. |
| 4,603,694 | A | 8/1986 | Wheeler |
| 4,650,462 | A | 3/1987 | DeSatnick et al. |
| 4,662,869 | A | 5/1987 | Wright |
| 4,673,393 | A | 6/1987 | Suzuki et al. |
| 4,700,694 | A | 10/1987 | Shishido |
| 4,729,763 | A | 3/1988 | Henrie |
| 4,848,323 | A | 7/1989 | Marijnissen et al. |
| 4,850,423 | A | 7/1989 | Allen et al. |
| 4,895,565 | A | 1/1990 | Hillstead |
| RE33,258 | E | 7/1990 | Onik et al. |
| 4,949,718 | A | 8/1990 | Neuwirth et al. |
| 4,998,527 | A | 3/1991 | Meyer |
| 5,061,238 | A | 10/1991 | Shuler |
| 5,078,725 | A | 1/1992 | Enderle et al. |
| 5,104,377 | A | 4/1992 | Levine |
| 5,108,414 | A | 4/1992 | Enderle et al. |
| 5,125,903 | A | 6/1992 | McLaughlin et al. |
| 5,163,433 | A | 11/1992 | Kagawa et al. |
| 5,163,949 | A | 11/1992 | Bonutti |
| 5,176,628 | A | 1/1993 | Charles et al. |
| 5,183,031 | A | 2/1993 | Rossoff |
| 5,195,541 | A | 3/1993 | Obenchain |
| 5,201,756 | A | 4/1993 | Horzewski et al. |
| 5,222,971 | A | 6/1993 | Willard et al. |
| 5,246,016 | A | 9/1993 | Lieber et al. |
| 5,259,836 | A | 11/1993 | Thurmond et al. |
| 5,269,798 | A | 12/1993 | Winkler |
| 5,275,609 | A | 1/1994 | Pingleton et al. |
| 5,284,472 | A | 2/1994 | Sussman et al. |
| 5,304,115 | A | 4/1994 | Pflueger |
| 5,320,091 | A | 6/1994 | Grossi et al. |
| 5,334,183 | A | 8/1994 | Wuchinich |
| 5,350,390 | A | 9/1994 | Sher |
| 5,361,752 | A | 11/1994 | Moll et al. |
| 5,377,668 | A | 1/1995 | Ehmsen et al. |
| 5,392,765 | A | 2/1995 | Muller |
| 5,402,772 | A | 4/1995 | Moll et al. |
| 5,403,276 | A | 4/1995 | Schechter et al. |
| 5,423,844 | A | 6/1995 | Miller |
| 5,443,470 | A | 8/1995 | Stern et al. |
| 5,450,843 | A | 9/1995 | Moll et al. |
| 5,458,112 | A | 10/1995 | Weaver |
| 5,472,439 | A | 12/1995 | Hurd |
| 5,484,401 | A | 1/1996 | Rodriguez et al. |
| 5,490,860 | A | 2/1996 | Middle et al. |
| 5,503,626 | A | 4/1996 | Goldrath |
| 5,505,730 | A | 4/1996 | Edwards |
| 5,507,760 | A | 4/1996 | Wynne et al. |
| 5,514,091 | A | 5/1996 | Yoon |
| 5,522,790 | A | 6/1996 | Moll et al. |
| 5,526,822 | A | 6/1996 | Burbank et al. |
| 5,540,658 | A | 7/1996 | Evans et al. |
| 5,575,788 | A | 11/1996 | Baker et al. |
| 5,601,583 | A | 2/1997 | Donahue et al. |
| 5,602,449 | A | 2/1997 | Krause et al. |
| 5,618,296 | A | 4/1997 | Sorensen et al. |
| 5,624,395 | A | 4/1997 | Mikhail et al. |
| 5,624,399 | A | 4/1997 | Ackerman |
| 5,656,013 | A | 8/1997 | Yoon |
| 5,695,511 | A | 12/1997 | Cano et al. |
| 5,697,940 | A | 12/1997 | Chu et al. |
| 5,709,664 | A | 1/1998 | Vanderbroek et al. |
| 5,725,524 | A | 3/1998 | Kordis |
| 5,730,725 | A | 3/1998 | Yoon |
| 5,738,629 | A | 4/1998 | Moll et al. |
| 5,741,287 | A | 4/1998 | Alden et al. |
| 5,743,850 | A | 4/1998 | Moll et al. |
| 5,743,851 | A | 4/1998 | Moll et al. |
| 5,749,845 | A | 5/1998 | Hildebrand et al. |
| 5,749,889 | A | 5/1998 | Bacich et al. |
| 5,755,731 | A | 5/1998 | Grinberg |
| 5,759,185 | A | 6/1998 | Grinberg |
| 5,775,333 | A | 7/1998 | Burbank et al. |
| 5,782,800 | A | 7/1998 | Yoon |
| 5,800,493 | A | 9/1998 | Stevens et al. |
| 5,807,401 | A | 9/1998 | Grieshaber et al. |
| 5,823,945 | A | 10/1998 | Moll et al. |

(56) References Cited

U.S. PATENT DOCUMENTS

| | | | |
|---|---|---|---|
| 5,823,971 A | 10/1998 | Robinson et al. | |
| 5,843,046 A | 12/1998 | Motisi et al. | |
| 5,855,549 A | 1/1999 | Newman | |
| 5,857,585 A | 1/1999 | Tolkoff et al. | |
| 5,865,728 A | 2/1999 | Moll et al. | |
| 5,873,815 A | 2/1999 | Kerin et al. | |
| 5,891,134 A | 4/1999 | Goble et al. | |
| 5,899,915 A | 4/1999 | Saadat | |
| 5,902,251 A | 5/1999 | VanHooydonk | |
| 5,904,649 A | 5/1999 | Andrese | |
| 5,904,680 A | 5/1999 | Kordis et al. | |
| 5,906,615 A | 5/1999 | Thompson | |
| 5,911,739 A | 6/1999 | Kordis et al. | |
| 5,916,198 A | 6/1999 | Dillow | |
| 5,928,161 A | 7/1999 | Krulevitch et al. | |
| 5,954,714 A | 9/1999 | Saadat et al. | |
| 5,954,715 A | 9/1999 | Harrington et al. | |
| 5,961,444 A | 10/1999 | Thompson | |
| 5,961,532 A | 10/1999 | Finely et al. | |
| 5,964,755 A | 10/1999 | Edwards | |
| 5,964,777 A | 10/1999 | Drucker | |
| 5,972,000 A | 10/1999 | Beyer et al. | |
| 5,979,494 A | 11/1999 | Perkins et al. | |
| 6,002,968 A | 12/1999 | Edwards | |
| 6,017,316 A | 1/2000 | Ritchart et al. | |
| 6,032,673 A | 3/2000 | Savage et al. | |
| 6,039,748 A | 3/2000 | Savage et al. | |
| 6,042,590 A | 3/2000 | Sporri et al. | |
| 6,068,626 A | 5/2000 | Harrington et al. | |
| 6,080,129 A | 6/2000 | Blaisdell | |
| 6,086,544 A | 7/2000 | Hibner et al. | |
| 6,099,541 A | 8/2000 | Klopotek | |
| 6,117,070 A | 9/2000 | Akiba | |
| 6,119,973 A | 9/2000 | Galloway | |
| 6,126,635 A | 10/2000 | Simpson et al. | |
| 6,139,570 A | 10/2000 | Saadat et al. | |
| 6,149,632 A | 11/2000 | Landuyt | |
| 6,159,209 A | 12/2000 | Hakky | |
| 6,190,357 B1 | 2/2001 | Ferrari et al. | |
| 6,216,043 B1 | 4/2001 | Swanson et al. | |
| 6,216,044 B1 | 4/2001 | Kordis | |
| 6,221,007 B1 | 4/2001 | Green | |
| 6,251,121 B1 | 6/2001 | Saadat | |
| 6,293,952 B1 | 9/2001 | Brosens et al. | |
| 6,319,272 B1 | 11/2001 | Brenneman et al. | |
| 6,328,686 B1 | 12/2001 | Kovac | |
| 6,378,524 B1 | 4/2002 | Jones | |
| 6,387,110 B1 | 5/2002 | Drucker et al. | |
| 6,395,012 B1 | 5/2002 | Yoon et al. | |
| 6,402,701 B1 | 6/2002 | Kaplan et al. | |
| 6,428,498 B2 | 8/2002 | Uflacker | |
| 6,428,539 B1 | 8/2002 | Baxter et al. | |
| 6,432,116 B1 | 8/2002 | Callister et al. | |
| 6,440,061 B1 | 8/2002 | Wenner et al. | |
| 6,458,076 B1 | 10/2002 | Pruitt | |
| 6,471,644 B1 | 10/2002 | Sidor, Jr. | |
| 6,494,909 B2 | 12/2002 | Greenhigh | |
| 6,517,561 B1 | 2/2003 | Phillips | |
| 6,537,207 B1 | 3/2003 | Rice et al. | |
| 6,547,784 B1 | 4/2003 | Thompson et al. | |
| 6,565,557 B1 | 5/2003 | Sporri et al. | |
| 6,605,037 B1 | 8/2003 | Moll et al. | |
| 6,607,545 B2 | 8/2003 | Kammerer et al. | |
| 6,612,977 B2 | 9/2003 | Staskin et al. | |
| 6,626,924 B1 | 9/2003 | Klopotek | |
| 6,626,940 B2 | 9/2003 | Crowley | |
| 6,638,235 B2 | 10/2003 | Miller et al. | |
| 6,638,289 B1 * | 10/2003 | Johnson | A61B 17/32002 606/170 |
| 6,673,023 B2 | 1/2004 | Pflueger | |
| 6,673,101 B1 | 1/2004 | Fitzgerald et al. | |
| 6,682,477 B2 | 1/2004 | Boebel et al. | |
| 6,705,986 B2 | 3/2004 | Fiegel et al. | |
| 6,709,667 B1 | 3/2004 | Lowe et al. | |
| 6,742,236 B1 | 6/2004 | Dion et al. | |
| 6,758,882 B2 | 7/2004 | Nakamura et al. | |
| 6,763,833 B1 | 7/2004 | Khera et al. | |
| 6,802,825 B2 | 10/2004 | Ackerman et al. | |
| 6,805,131 B2 | 10/2004 | Kordis | |
| 6,812,204 B1 | 11/2004 | McHale et al. | |
| 6,821,274 B2 | 11/2004 | Mchale et al. | |
| 6,821,282 B2 | 11/2004 | Perry et al. | |
| 6,827,703 B1 | 12/2004 | Ackerman | |
| 6,858,024 B1 | 2/2005 | Berg et al. | |
| 6,896,682 B1 | 5/2005 | Mcclellan et al. | |
| 6,951,569 B2 | 10/2005 | Nohilly et al. | |
| 6,960,203 B2 | 11/2005 | Xiao et al. | |
| 6,979,332 B2 | 12/2005 | Adams | |
| 6,997,925 B2 | 2/2006 | Maguire et al. | |
| 7,037,321 B2 | 5/2006 | Sachdeva et al. | |
| 7,070,559 B2 | 7/2006 | Adams et al. | |
| 7,105,003 B2 | 9/2006 | Hitebrandt | |
| 7,150,713 B2 | 12/2006 | Shener et al. | |
| 7,189,206 B2 | 3/2007 | Quick et al. | |
| 7,226,459 B2 | 6/2007 | Cesarini | |
| 7,226,460 B2 | 6/2007 | Gibson et al. | |
| 7,241,297 B2 | 7/2007 | Shaolian et al. | |
| 7,249,602 B1 | 7/2007 | Emanuel | |
| 7,458,940 B2 | 12/2008 | Miller | |
| 7,462,187 B2 | 12/2008 | Johnson et al. | |
| 7,468,060 B2 | 12/2008 | Utley et al. | |
| 7,481,817 B2 | 1/2009 | Sauer | |
| 7,491,212 B2 | 2/2009 | Sikora et al. | |
| 7,497,833 B2 | 3/2009 | Miller | |
| 7,510,563 B2 | 3/2009 | Cesarini et al. | |
| 7,588,545 B2 | 9/2009 | Cohen et al. | |
| 7,611,474 B2 | 11/2009 | Hibner et al. | |
| 7,666,200 B2 | 2/2010 | Heisler | |
| 7,749,254 B2 | 7/2010 | Sobelman et al. | |
| 7,753,857 B2 | 7/2010 | Hibner | |
| 7,763,033 B2 | 7/2010 | Gruber et al. | |
| 7,785,250 B2 | 8/2010 | Nakao | |
| 7,806,835 B2 | 10/2010 | Hibner et al. | |
| 7,922,737 B1 | 4/2011 | Cesarini et al. | |
| 7,938,804 B2 | 5/2011 | Fischvogt | |
| 7,963,433 B2 | 6/2011 | Whitman et al. | |
| 7,981,130 B2 | 7/2011 | Seeh | |
| 8,025,656 B2 | 9/2011 | Gruber et al. | |
| 8,528,563 B2 | 9/2013 | Gruber et al. | |
| 8,574,253 B2 | 11/2013 | Gruber et al. | |
| 8,647,349 B2 | 2/2014 | Gruber et al. | |
| 8,834,487 B2 | 9/2014 | Gruber et al. | |
| 8,840,625 B2 | 9/2014 | Adams et al. | |
| 8,840,626 B2 | 9/2014 | Adams et al. | |
| 8,951,274 B2 | 2/2015 | Adams et al. | |
| 9,095,366 B2 * | 8/2015 | Sullivan | A61B 17/3415 |
| 9,339,288 B2 * | 5/2016 | Sullivan | A61B 17/3205 |
| 9,539,019 B2 * | 1/2017 | Sullivan | A61B 17/3205 |
| 10,130,389 B2 * | 11/2018 | Sullivan | A61M 1/0082 |
| 2001/0008575 A1 | 7/2001 | Rho et al. | |
| 2001/0029371 A1 | 10/2001 | Kordis | |
| 2001/0039963 A1 | 11/2001 | Spear et al. | |
| 2001/0041900 A1 | 11/2001 | Callister | |
| 2001/0047183 A1 | 11/2001 | Privitera et al. | |
| 2001/0056222 A1 | 12/2001 | Rudischauser et al. | |
| 2002/0010457 A1 | 1/2002 | Duchon et al. | |
| 2002/0020417 A1 | 1/2002 | Nobles et al. | |
| 2002/0068934 A1 | 6/2002 | Edwards et al. | |
| 2002/0082519 A1 | 6/2002 | Miller et al. | |
| 2002/0082634 A1 | 6/2002 | Kammerer et al. | |
| 2003/0050639 A1 | 3/2003 | Yachia et al. | |
| 2003/0083684 A1 | 5/2003 | Cesarini et al. | |
| 2003/0114875 A1 | 6/2003 | Sjostrom | |
| 2003/0153940 A1 | 8/2003 | Nohilly et al. | |
| 2004/0002702 A1 | 1/2004 | Xiao et al. | |
| 2004/0004703 A1 | 1/2004 | Xiao et al. | |
| 2004/0049211 A1 | 3/2004 | Tremulis et al. | |
| 2004/0116955 A1 | 6/2004 | Foltz et al. | |
| 2004/0127932 A1 | 7/2004 | Shah | |
| 2004/0204682 A1 | 10/2004 | Smith | |
| 2004/0204732 A1 * | 10/2004 | Muchnik | A61F 9/00763 606/171 |
| 2004/0225187 A1 | 11/2004 | Kamrava et al. | |
| 2004/0255957 A1 | 12/2004 | Cafferata | |

(56) References Cited

U.S. PATENT DOCUMENTS

| | | |
|---|---|---|
| 2004/0267157 A1 | 12/2004 | Miller et al. |
| 2005/0027245 A1 | 2/2005 | Sachdeva et al. |
| 2005/0045183 A1 | 3/2005 | Callister et al. |
| 2005/0080318 A1 | 4/2005 | Squicciarini |
| 2005/0090849 A1 | 4/2005 | Adams |
| 2005/0096669 A1 | 5/2005 | Rabiner et al. |
| 2005/0107663 A1 | 5/2005 | Saadat et al. |
| 2005/0113715 A1 | 5/2005 | Schwindt et al. |
| 2005/0113836 A1 | 5/2005 | Lozier et al. |
| 2005/0113857 A1 | 5/2005 | Nohilly et al. |
| 2005/0177168 A1 | 8/2005 | Brunnett et al. |
| 2005/0222598 A1 | 10/2005 | Ho et al. |
| 2005/0234437 A1 | 10/2005 | Baxter et al. |
| 2005/0240206 A1 | 10/2005 | Sjostrom |
| 2005/0182397 A1 | 11/2005 | Ryan |
| 2005/0245952 A1 | 11/2005 | Feller |
| 2005/0245960 A1 | 11/2005 | Grunderman |
| 2005/0250933 A1 | 11/2005 | Binz et al. |
| 2005/0250993 A1 | 11/2005 | Jaeger |
| 2005/0267408 A1 | 12/2005 | Grandt et al. |
| 2005/0277970 A1 | 12/2005 | Norman et al. |
| 2005/0277975 A1 | 12/2005 | Saadat et al. |
| 2005/0288551 A1 | 12/2005 | Callister et al. |
| 2006/0004436 A1 | 1/2006 | Amarant et al. |
| 2006/0009798 A1 | 1/2006 | Callister et al. |
| 2006/0036138 A1 | 2/2006 | Heller et al. |
| 2006/0047185 A1 | 3/2006 | Sherner et al. |
| 2006/0064074 A1 | 3/2006 | Mallaby |
| 2006/0089658 A1 | 4/2006 | Harrington |
| 2006/0189972 A1 | 8/2006 | Grossman |
| 2006/0200042 A1 | 9/2006 | Weikel, Jr. et al. |
| 2006/0206136 A1 | 9/2006 | Sachdeva et al. |
| 2006/0212055 A1 | 9/2006 | Karabey et al. |
| 2006/0229647 A1 | 10/2006 | Spitz et al. |
| 2006/0241344 A1 | 10/2006 | Wilk |
| 2006/0241586 A1 | 10/2006 | Wilk |
| 2006/0241630 A1 | 10/2006 | Brunnet et al. |
| 2006/0293560 A1 | 12/2006 | Nguyen et al. |
| 2007/0010845 A1 | 1/2007 | Gong et al. |
| 2007/0161957 A1 | 7/2007 | Guenther et al. |
| 2007/0225744 A1 | 9/2007 | Nobles |
| 2007/0227544 A1 | 10/2007 | Swann et al. |
| 2007/0232859 A1 | 10/2007 | Secrest et al. |
| 2008/0015621 A1 | 1/2008 | Emanuel |
| 2008/0051758 A1 | 2/2008 | Rioux et al. |
| 2008/0058588 A1 | 3/2008 | Emanuel |
| 2008/0058595 A1 | 3/2008 | Snoke et al. |
| 2008/0065125 A1 | 3/2008 | Olson |
| 2008/0097467 A1 | 4/2008 | Gruber et al. |
| 2008/0097469 A1 | 4/2008 | Gruber et al. |
| 2008/0146872 A1 | 6/2008 | Gruber et al. |
| 2008/0146873 A1 | 6/2008 | Adams et al. |
| 2008/0147012 A1 | 6/2008 | Rome |
| 2008/0154292 A1* | 6/2008 | Huculak et al. ........ A61B 17/32 606/167 |
| 2008/0183192 A1 | 7/2008 | Saal et al. |
| 2008/0208230 A1 | 8/2008 | Chin et al. |
| 2008/0249366 A1 | 10/2008 | Gruber et al. |
| 2008/0249534 A1 | 10/2008 | Gruber et al. |
| 2008/0249553 A1* | 10/2008 | Gruber ............. A61B 17/32002 606/171 |
| 2008/0262302 A1 | 10/2008 | Azarbarzin et al. |
| 2008/0281224 A1 | 11/2008 | Johnson |
| 2008/0319342 A1 | 12/2008 | Shabaz et al. |
| 2009/0005739 A1 | 1/2009 | Hart et al. |
| 2009/0048485 A1 | 2/2009 | Heisler |
| 2009/0054728 A1 | 2/2009 | Trusty |
| 2009/0118699 A1 | 5/2009 | Utley et al. |
| 2009/0137927 A1 | 5/2009 | Miller |
| 2009/0177217 A1 | 7/2009 | Keller |
| 2009/0198149 A1 | 8/2009 | Privitera et al. |
| 2009/0270812 A1 | 10/2009 | Litscher et al. |
| 2009/0270895 A1 | 10/2009 | Churchill et al. |
| 2009/0270898 A1 | 10/2009 | Chin et al. |
| 2010/0063360 A1 | 3/2010 | Harrington et al. |
| 2010/0076343 A1 | 3/2010 | Vetter et al. |
| 2010/0087798 A1 | 4/2010 | Adams et al. |
| 2010/0152533 A1 | 6/2010 | Mark |
| 2010/0152758 A1 | 6/2010 | Mark et al. |
| 2010/0152761 A1 | 6/2010 | Mark |
| 2010/0160818 A1 | 6/2010 | Haberstich et al. |
| 2010/0179480 A1 | 7/2010 | Sugiki et al. |
| 2010/0185153 A1 | 7/2010 | Sugiki et al. |
| 2010/0185222 A1 | 7/2010 | Keller |
| 2010/0198242 A1 | 8/2010 | Heisler |
| 2010/0217299 A1 | 8/2010 | Williams et al. |
| 2010/0222700 A1 | 9/2010 | Hibner |
| 2010/0256662 A1 | 10/2010 | Racenet et al. |
| 2010/0274194 A1 | 10/2010 | Sobelman et al. |
| 2010/0312053 A1 | 12/2010 | Larsen |
| 2011/0034943 A1 | 2/2011 | Churchill et al. |
| 2011/0046624 A1 | 2/2011 | Lin |
| 2011/0077674 A1 | 3/2011 | Sullivan et al. |
| 2011/0118544 A1 | 5/2011 | Adams et al. |
| 2011/0125177 A1 | 5/2011 | Yates et al. |
| 2011/0192883 A1 | 8/2011 | Whitman et al. |
| 2014/0135806 A1 | 5/2014 | Shener-Irmakoglu et al. |

FOREIGN PATENT DOCUMENTS

| | | |
|---|---|---|
| EP | 0141589 | 5/1985 |
| EP | 0366292 | 5/1990 |
| EP | 0449663 | 10/1991 |
| EP | 0531710 | 10/1991 |
| EP | 0539125 | 4/1993 |
| EP | 782427 | 2/1996 |
| EP | 853468 | 5/1996 |
| EP | 0812573 | 12/1997 |
| EP | 1259180 | 9/2001 |
| EP | 1635695 | 1/2005 |
| EP | 1676537 A1 | 7/2006 |
| EP | 0809466 | 11/2006 |
| FR | 2701401 | 8/1994 |
| JP | 2005-116295 | 5/2005 |
| JP | 2005118295 | 5/2005 |
| WO | WO9203099 | 3/1992 |
| WO | 1994007445 | 4/1994 |
| WO | 1994011052 | 5/1994 |
| WO | 195010326 | 4/1995 |
| WO | 1996015741 | 5/1996 |
| WO | 1998018520 | 5/1998 |
| WO | 1998029068 | 7/1998 |
| WO | 1998051244 | 11/1998 |
| WO | WO9849953 | 11/1998 |
| WO | WO 99/11184 | 3/1999 |
| WO | 1995032011 | 11/1999 |
| WO | 1999060960 | 12/1999 |
| WO | 2000000100 | 1/2000 |
| WO | 2000012832 | 3/2000 |
| WO | 2000066031 | 11/2000 |
| WO | 2001008575 | 2/2001 |
| WO | 2003037194 | 5/2003 |
| WO | 2005009504 | 2/2005 |
| WO | 2005048862 | 6/2005 |
| WO | 2005074844 | 8/2005 |
| WO | 2005104966 | 11/2005 |
| WO | 2009111717 | 9/2009 |
| WO | 2010127171 | 11/2010 |
| WO | 2010127174 | 11/2010 |
| WO | 2014/075039 | 5/2014 |
| WO | 2014075039 | 5/2014 |

OTHER PUBLICATIONS

Office action dated Dec. 14, 2018 for Chinese application No. 201610066887.3, in Chinese with English language translation.

Reference AQ "Fishing Reel produced and sold by Shinano of Japan into the U.S. prior to Oct. 26, 2001," as cited in the IDS filed Oct. 17, 2005 in the prosecution file history of U.S. Appl. No. 09/983,810, 7 pages.

International Search Report and Written Opinion dated Jan. 11, 2011, in PCT Application No. PCT/US2010/056416 in 14 pages.

(56) References Cited

OTHER PUBLICATIONS

International Search Report and Written Opinion dated Jul. 6, 2010, in PCT Application No. PCT/US2010/033047 in 13 pages.
International Search Report and Written Opinion dated Jun. 29, 2010, in PCT Application No. PCT/US2010/033050 in 7 pages.
"When mechanical dilation is necessary, a few prerequisites can make a difference", OBG Management, Apr. 2009, vol. 21, No. 4, p. 29-33.
Mark H. Emanuel, "The Intra Uterine Morcellator: A New Hysteroscopic Operating Technique to Remove Intrauterine Polyps and Myomas," Journal of Minimally Invasive Gynecology, vol. 12, p. 62-66 (2005).
International Search Report and Written Opinion in PCT Application No. PCT/US07/79449, dated Jan. 28, 2008.
International Search Report and Written Opinion in PCT Application No. PCT/US07/783982, dated May 20, 2008.
International Search Report and Written Opinion in PCT Application No. PCT/US08/59493, dated Apr. 4, 2008.
International Search Report and Written Opinion in PCT Application No. PCT/US07/783833, dated Jun. 5, 2008.
International Search Report and Written Opinion in PCT Application No. PCT/US07/59504, dated Sep. 4, 2008.
International Search Report and Written Opinion in PCT Application No. PCT/US07/59503, dated Sep. 5, 2008.
Notice of Acceptance and accepted claims for related application AU 2010242907, Applicant Hologic, Inc., dated May 6, 2015 (6 pages).
Office Action from Chinese application No. 201610066887.3, Applicant Hologic, Inc., dated Aug. 31, 2017, including English Translation provided by foreign associate, 19 pages.
Communication under Rule 71(3) EPC for EP Application No. 16182254.9 dated Oct. 20, 2017, Applicant Hologic, Inc., 7 pages.
Second Office Action from Chinese application No. 201610066887.3, Applicant Hologic, Inc., dated Jun. 1, 2018, including English Translation provided by foreign associate, 26 pages.
Chen Airong, Li Xinde, "Metal Cutting Principle and Tool", China Commercial Press, relevant pp. 106-107, published Sep. 30, 2007, 7 pages.

\* cited by examiner

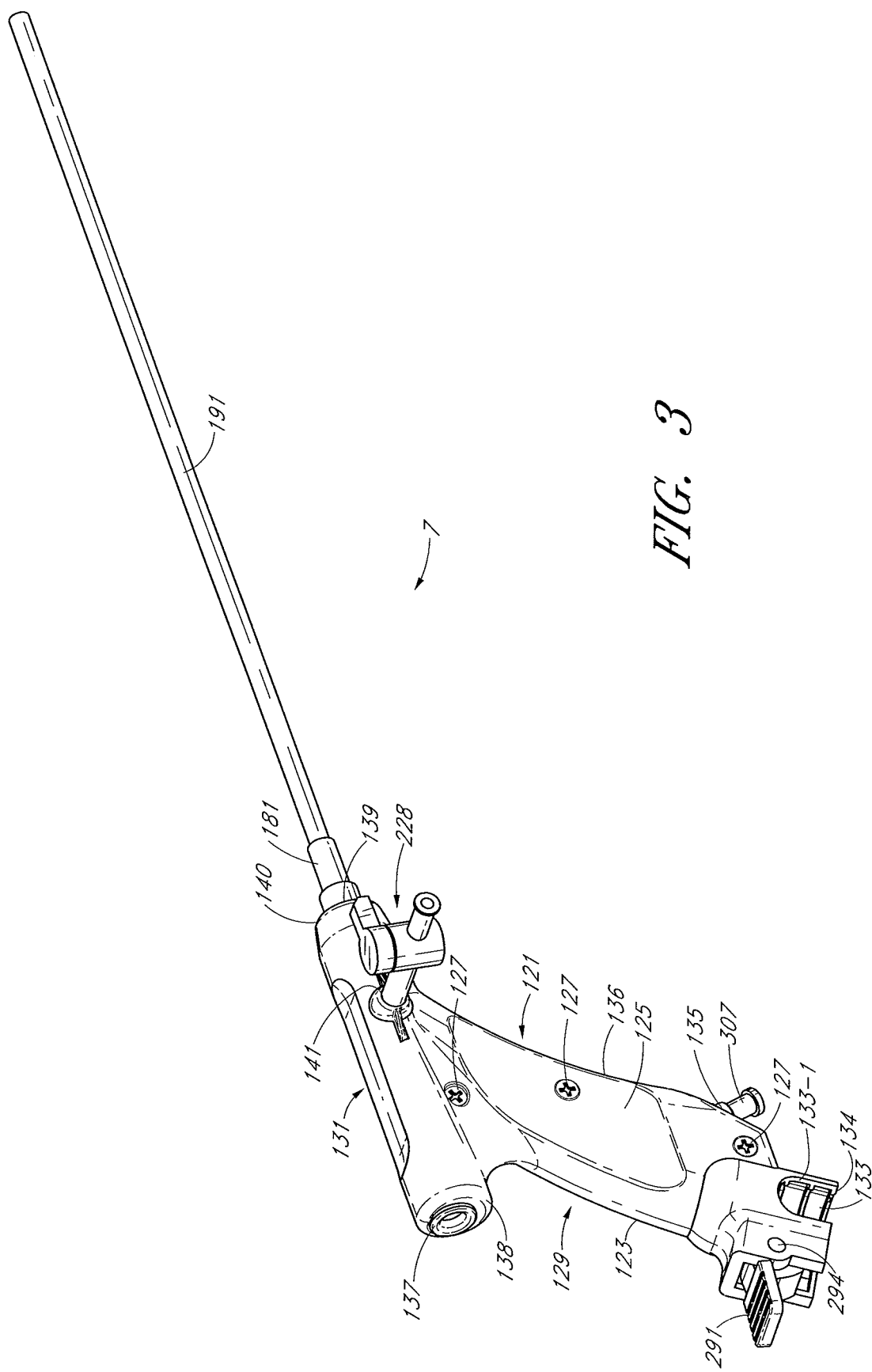

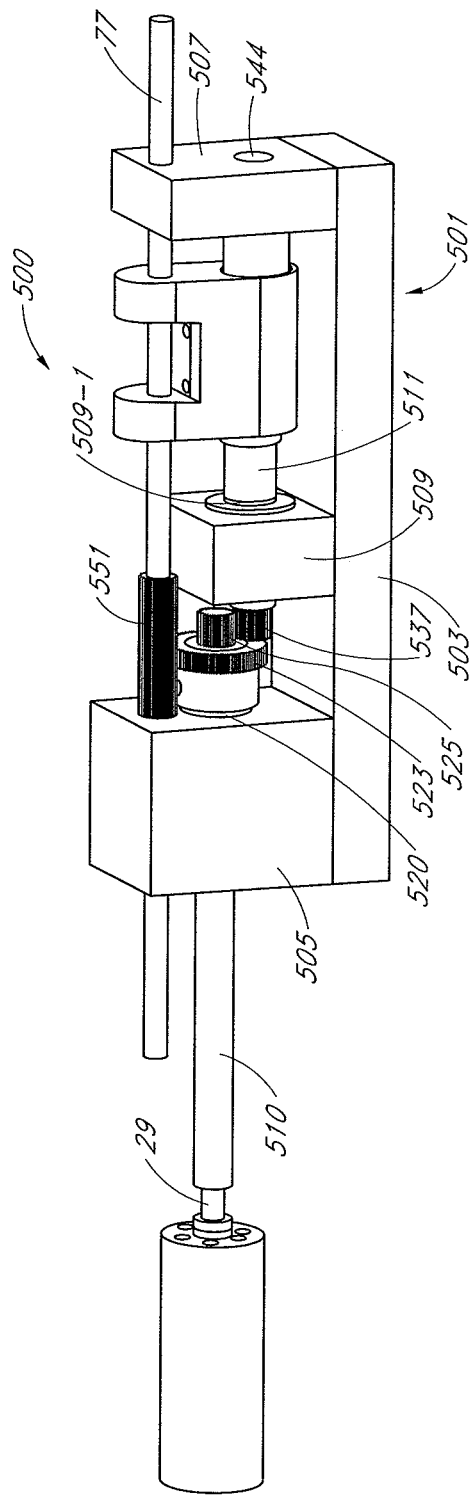
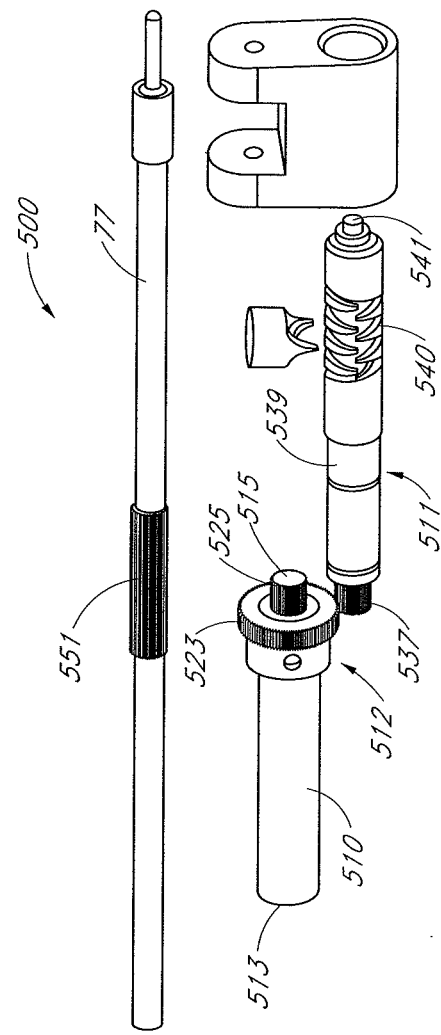
FIG. 15A
FIG. 15B

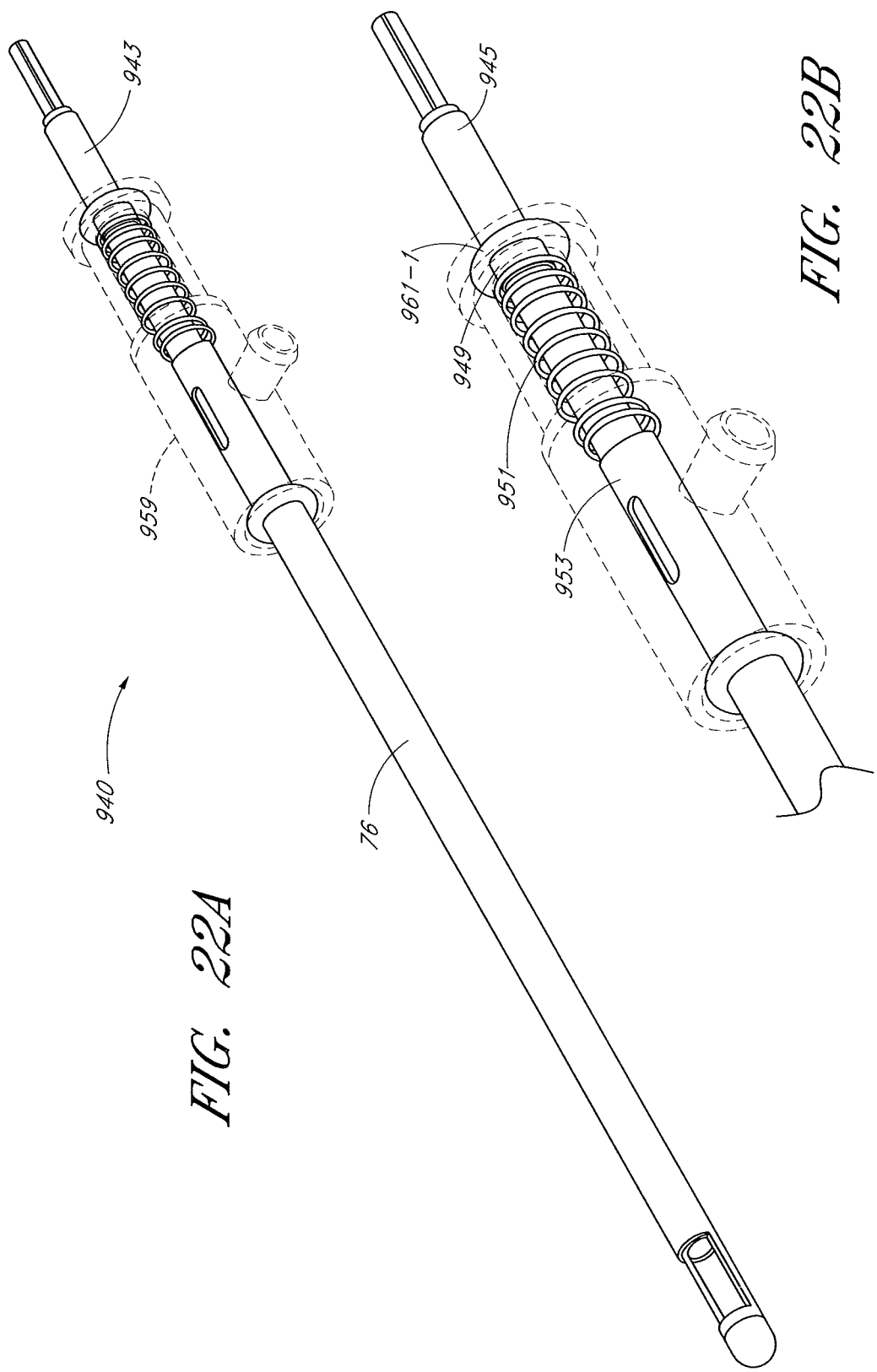

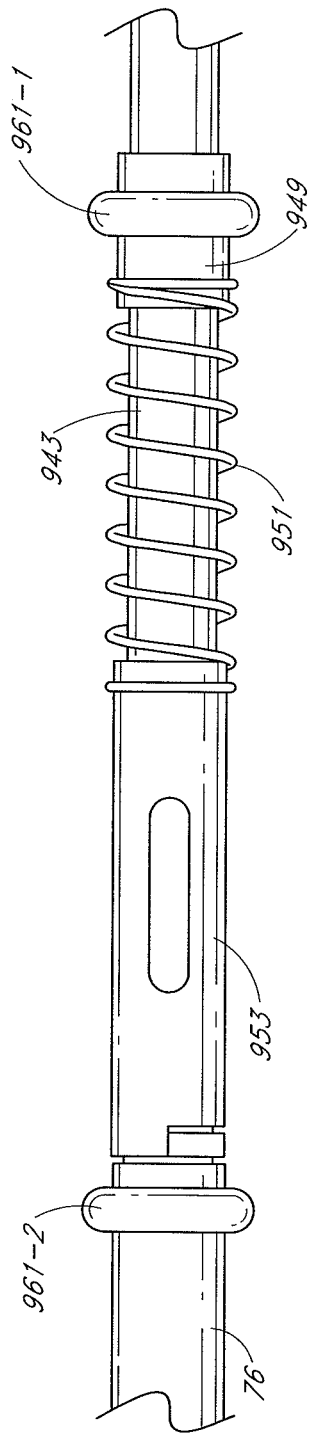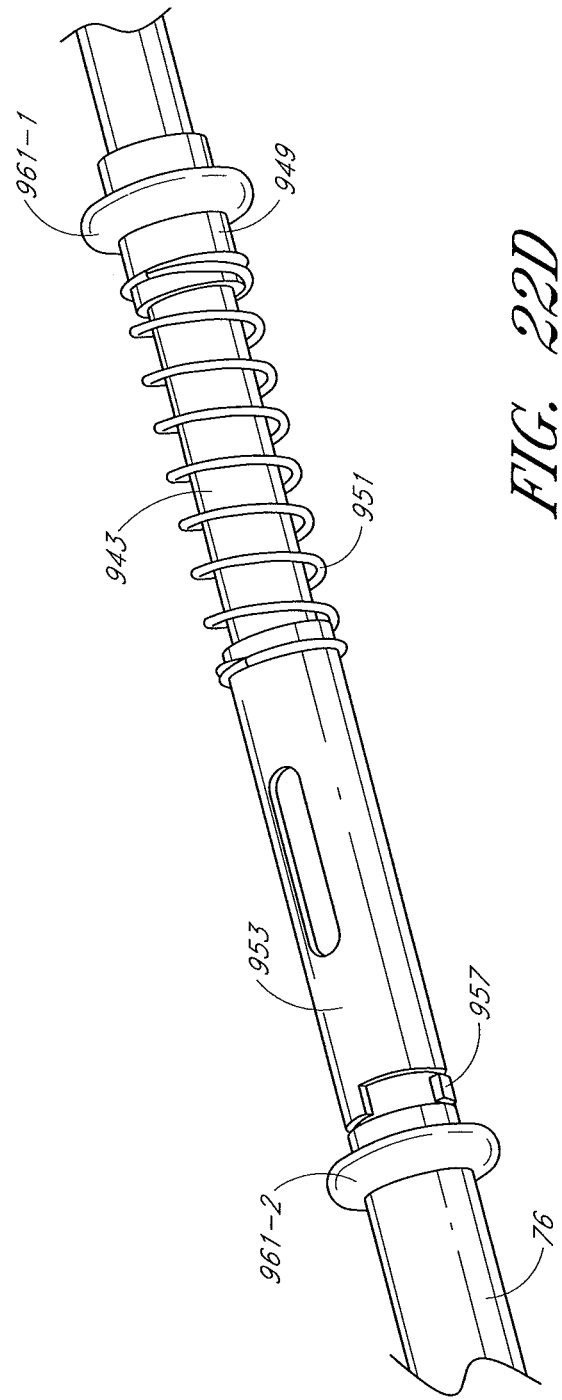

UTERINE FIBROID TISSUE REMOVAL DEVICE

CROSS-REFERENCE TO RELATED APPLICATIONS

The present application is a continuation of U.S. patent application Ser. No. 15/365,502, filed Nov. 30, 2016, now U.S. Pat. No. 10,130,389, which is a continuation of U.S. patent application Ser. No. 14/983,024, filed Dec. 29, 2015, now U.S. Pat. No. 9,539,019, which is a continuation of U.S. patent application Ser. No. 14/680,276, filed Apr. 7, 2015, now U.S. Pat. No. 9,339,288, which is a continuation of U.S. patent application Ser. No. 12/432,686, filed Apr. 29, 2009, now U.S. Pat. No. 9,095,366.

BACKGROUND OF THE INVENTION

The present invention relates generally to methods, systems and devices for the removal of tissue and relates more particularly to methods, systems, and devices well-suited for the removal of uterine fibroids and other abnormal gynecological tissues.

It is believed that uterine fibroids occur in a substantial percentage of the female population, perhaps in at least 20 to 40 percent of all women. Uterine fibroids are well-defined, non-cancerous tumors that are commonly found in the smooth muscle layer of the uterus. In many instances, uterine fibroids can grow to be several centimeters in diameter and may cause symptoms like menorrhagia (prolonged or heavy menstrual bleeding), pelvic pressure or pain, and reproductive dysfunction.

Current treatments for uterine fibroids include pharmacological therapy, hysterectomy, uterine artery embolization, and hysteroscopic resection. Pharmacological therapy typically involves the administration of NSAIDS (non-steroidal anti-inflammatory drugs), estrogen-progesterone combinations, and GnRH (gonadotropin releasing hormone) analogues. However, current pharmacological therapies are largely ineffective and merely palliative. By comparison, a hysterectomy involves the surgical removal of the uterus from a patient. For this reason, a hysterectomy represents a highly effective way of ridding a patient of uterine fibroids. As a result, several hundred thousand hysterectomies are typically performed annually in the United States to treat uterine fibroids. However, despite their widespread use, hysterectomies also possess certain disadvantages, such as a loss of fertility, sexual dysfunction, and the risks commonly associated with a major surgical procedure, such as hemorrhaging, lesions, infections, pain and prolonged recovery. Uterine artery embolization involves inserting a catheter into a femoral artery and then guiding the catheter to a uterine fibroid artery. Small particles are then injected from the catheter into the fibroid artery, blocking its blood supply and causing it to eventually shrink and die. Although this procedure is less invasive than a hysterectomy, it often results in pain-related, post-surgical complications. Moreover, the physicians that are trained to perform uterine artery embolization are typically interventional radiologists, as opposed to physicians trained specifically to take care of gynecological problems, whereas the physicians trained specifically to take care of gynecological problems typically do not possess the skill to perform catheter-based uterine artery embolization.

Hysteroscopic resection typically involves inserting a hysteroscope (i.e., an imaging scope) into the uterus through the vagina, i.e., transcervically, and then cutting away the fibroid from the uterus using a device delivered to the fibroid by the hysteroscope. Hysteroscopic resections typically fall into one of two varieties. In one variety, an electrocautery device in the form of a loop-shaped cutting wire is fixedly mounted on the distal end of the hysteroscope—the combination of the hysteroscope and the electrocautery device typically referred to as a resectoscope. The transmission of electrical current to the uterus with a resectoscope is typically monopolar, and the circuit is completed by a conductive path to the power unit for the device through a conductive pad applied to the patient's skin. In this manner, tissue is removed by contacting the loop with the part of the uterus wall of interest. Examples of such devices are disclosed, for example, in U.S. Pat. No. 5,906,615, inventor Thompson, issued May 25, 1999.

In the other variety of hysteroscopic resection, an electromechanical cutter is inserted through a working channel in the hysteroscope. Tissue is then removed by contacting the cutter, which typically has a rotating cutting instrument, with the part of the uterus wall of interest. Examples of the electromechanical cutter variety of hysteroscopic resection are disclosed in, for example, U.S. Pat. No. 7,226,459, inventors Cesarini et al., issued Jun. 5, 2007; U.S. Pat. No. 6,032,673, inventors Savage et al., issued Mar. 7, 2000; U.S. Pat. No. 5,730,752, inventors Alden et al., issued Mar. 24, 1998; U.S. Patent Application Publication No. US 2006/0047185 A1, inventors Shener et al., published Mar. 2, 2006; and PCT International Publication No. WO 99/11184, published Mar. 11, 1999, all of which are incorporated herein by reference.

In both of the above-described varieties of hysteroscopic resection, prior to fibroid removal, the uterus is typically distended to create a working space within the uterus. (Such a working space typically does not exist naturally in the uterus because the uterus is a flaccid organ. As such, the walls of the uterus are typically in contact with one another when in a relaxed state.) The conventional technique for creating such a working space within the uterus is to administer a fluid to the uterus through the hysteroscope under sufficient pressure to cause the uterus to become distended. Examples of the fluid used conventionally to distend the uterus include gases like carbon dioxide or, more commonly, liquids like water or certain aqueous solutions (e.g., a saline solution or a sugar-based aqueous solution). Where resection is effected using a resectoscope, it is typically necessary that the distending fluid not be current-conducting so that electricity is not conducted to undesired locations. However, because the distending fluid is administered under pressure (which pressure may be as great as 100 mm Hg or greater), there is a risk, especially when tissue is cut, that the distending fluid may be taken up by a blood vessel in the uterus, i.e., intravasation, which uptake may be quite harmful to the patient. Because excess intravasation can lead to death, it is customary to monitor the fluid uptake on a continuous basis using a scale system.

Nevertheless, despite the aforementioned risks of intravasation, with proper monitoring of fluid uptake, hysteroscopic resection is a highly effective and safe technique for removing uterine fibroids. However, one shortcoming with hysteroscopic resection is that it typically requires that anesthesia be administered to the patient. This is because conventional resectoscopes typically have a diameter in excess of 7 mm and because conventional hysteroscopes of the type through which mechanical cutter-type devices are inserted typically have a diameter of about 9 mm. By contrast, the cervix typically cannot be dilated to a diameter greater than about 5.5 mm without causing considerable discomfort to the patient. As a result, due to the need for anesthesia, hysteroscopic resection is typically performed in a hospital operating room and, as a result, bears a large cost due to the setting and the support personnel required.

SUMMARY OF THE INVENTION

The present invention provides a novel method, system and device for tissue removal. The method, system and device as described above may be used, for example, to remove uterine fibroids and other abnormal gynecological tissues.

According to one aspect of the invention, there is provided a tissue removal device, the tissue removal device comprising (a) a housing; (b) an outer tube, the outer tube being fixed to the housing and extending distally therefrom, the outer tube including a resection window; (c) an inner tube disposed within the outer tube, the inner tube being slidable and rotatable relative to the outer tube, the inner tube comprising a distal end; and (d) a drive mechanism for rotating the inner tube relative to the outer tube and, at the same time, for translationally oscillating the inner tube relative to the outer tube so that the distal end of the inner tube rotates while moving back and forth across the resection window, wherein said drive mechanism comprises a drive shaft shaped to include a double helical groove, said drive shaft being translationally stationary.

There is provided in accordance with another aspect of the present invention, a tubular cutting element for the tissue removal device of the present invention. The tubular cutting element is adapted for axial reciprocal movement within an outer tubular sleeve, the cutting element having an elongate tubular body having a proximal end, a distal end, and a cutting tip. The tubular body is formed in a drawing operation and the cutting tip is formed in a milling operation. The cutting tip is attached to the tubular body by soldering, brazing, welding, or other attachment technique.

In accordance with a further aspect of the present invention, there is provided a tubular cutting element for axial reciprocal movement within an outer tubular sleeve. The cutting element comprises an elongate tubular body, having a proximal end, a distal end and a cutting tip. The tubular body has a Rockwell C hardness of no more than about 40 and the cutting tip has a Rockwell C hardness of at least about 50. The cutting tip may have a Rockwell C hardness of at least about 60, or at least about 70.

A coating may be provided in-between the outer tubular sleeve and the inner tubular body. The coating may be applied to either the outer tubular sleeve or the inner tubular body. The coating may comprise a titanium nitride alloy. The coating may comprise a Rockwell C hardness of at least about 50, at least about 60, or at least about 70.

Additional aspects, features and advantages of the present invention will be set forth in part in the description which follows. The embodiments will be described in sufficient detail to enable those skilled in the art to practice the invention, and it is to be understood that other embodiments may be utilized and that structural or process changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIG. 3 is a perspective view of the introducer device shown in FIG. 1;

FIGS. 15(a) and 15(b) are fragmentary perspective and fragmentary partially exploded perspective views, respectively, of another alternate tissue removal device that may be used in the tissue removal system of FIG. 1;

FIGS. 22(a) through 22(e) are various views of another alternate tissue removal device that may be used in the tissue removal system of FIG. 1 (the vacuum housing not being shown in FIGS. 22(c) through 22(e) to reveal components positioned therewithin);

DETAILED DESCRIPTION OF THE PREFERRED EMBODIMENT

The present invention is described below primarily in the context of devices and procedures optimized for performing one or more therapeutic or diagnostic gynecological or urological procedures such as the removal of uterine fibroids or other abnormal uterine tissue. However, the devices and related procedures of the present invention may be used in a wide variety of applications throughout the body, through a variety of access pathways.

For example, the devices of the present invention can be optimized for use via open surgery, less invasive access such as laparoscopic access, or minimally invasive procedures such as via percutaneous access. In addition, the devices of the present invention can be configured for access to a therapeutic or diagnostic site via any of the body's natural openings to accomplish access via the ears, nose, mouth, and via trans-rectal, urethral and vaginal approach.

In addition to the performance of one or more gynecological and urologic procedures described in detail herein, the systems, methods, apparatus and devices of the present invention may be used to perform one or more additional procedures, including but not limited to access and tissue manipulation or removal from any of a variety of organs and tissues such as the bladder, breast, lung, stomach, bowel, esophagus, oral cavity, rectum, nasal sinus, Eustachian tubes, heart, gall bladder, spine, shoulder, knee, hip, brain, arteries, veins, and various ducts. Routes of access include but are not limited to trans-cervical; trans-vaginal-wall; trans-uteral; trans-vesicle; trans-urethral; and other routes.

Figure 1:
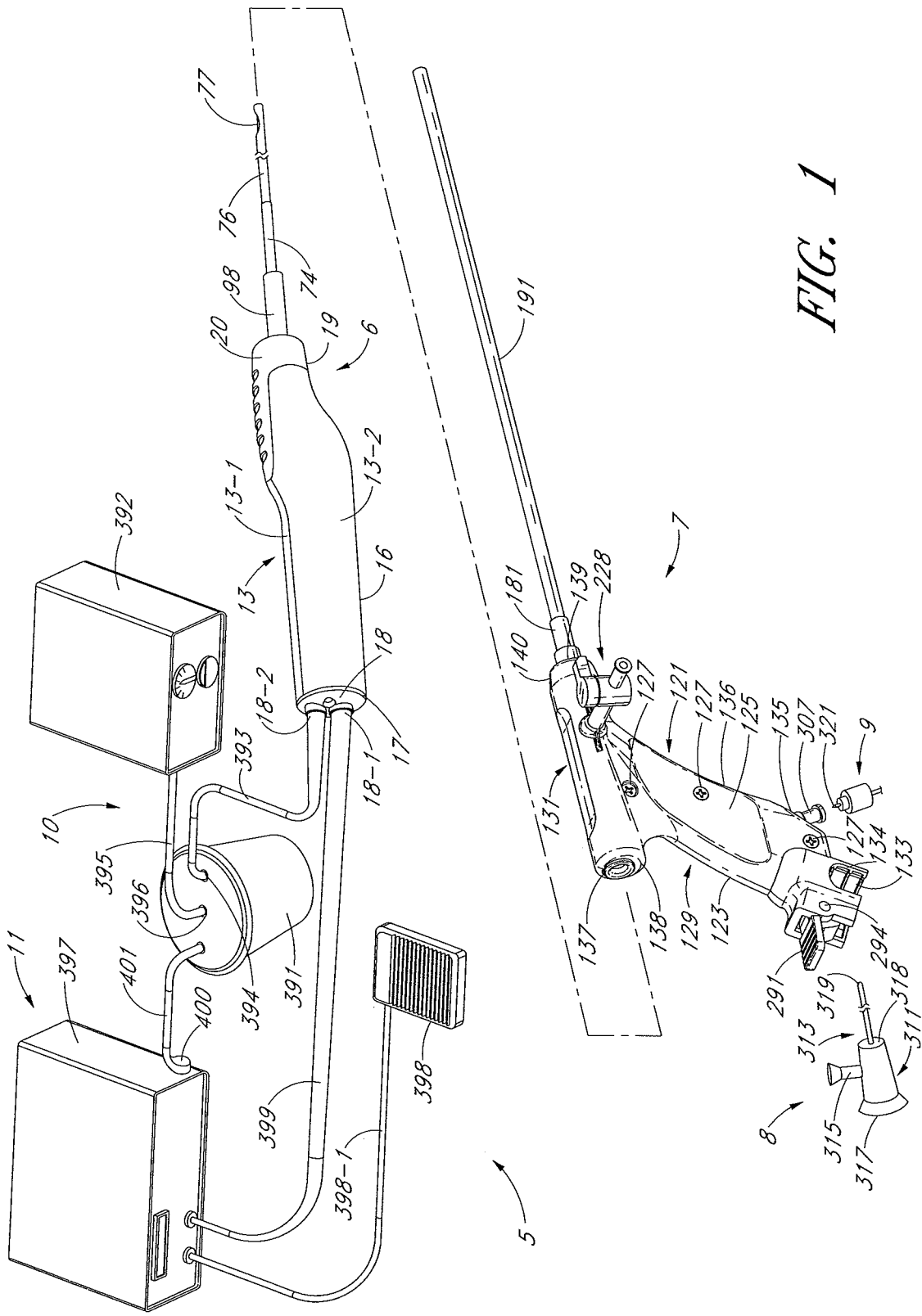
FIG. 1 is a partially exploded perspective view of a first embodiment of a tissue removal system constructed according to the teachings of the present invention.
Figure 2A:
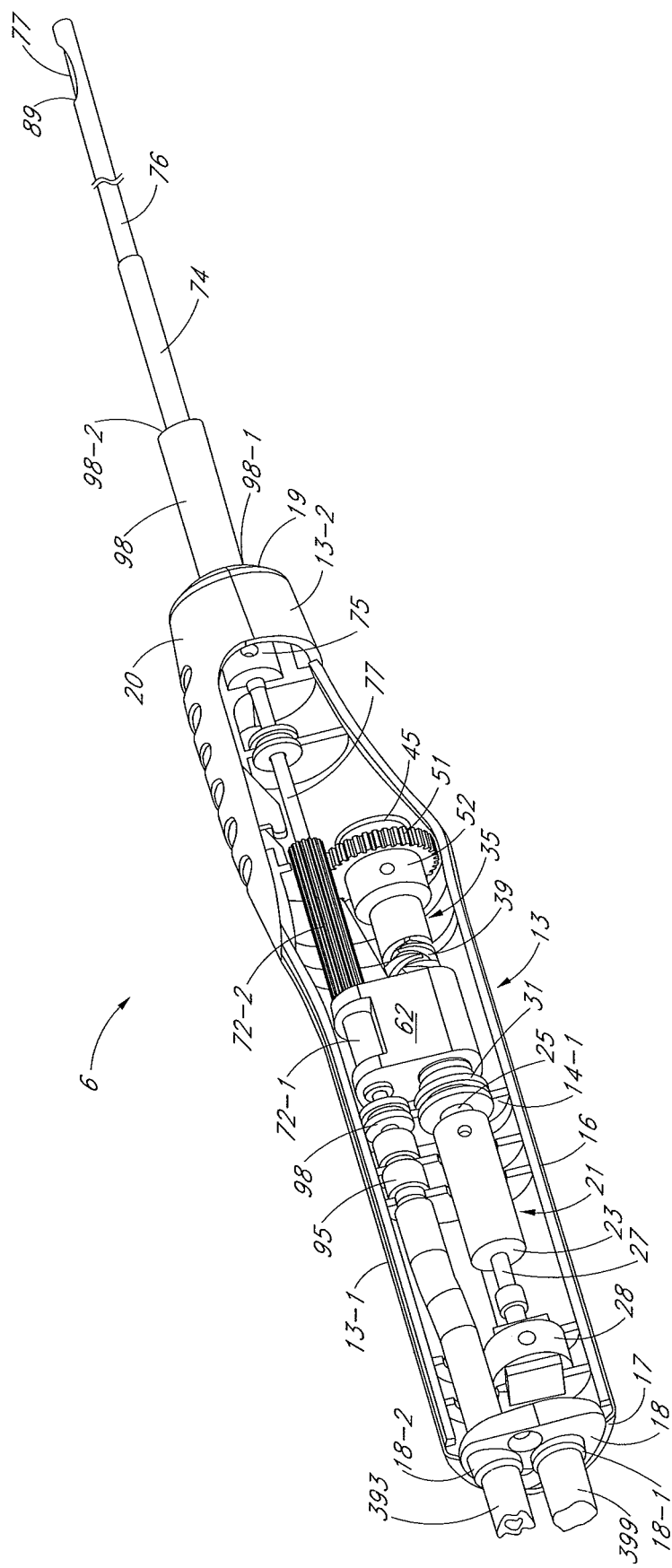
FIGS. 2(a) through 2(d) are various views of the tissue removal device shown in FIG. 1, the tissue removal device being shown in FIGS. 2(a) through 2(c) together with the distal ends of the vacuum tube and the external drive shaft.
Figure 2B:
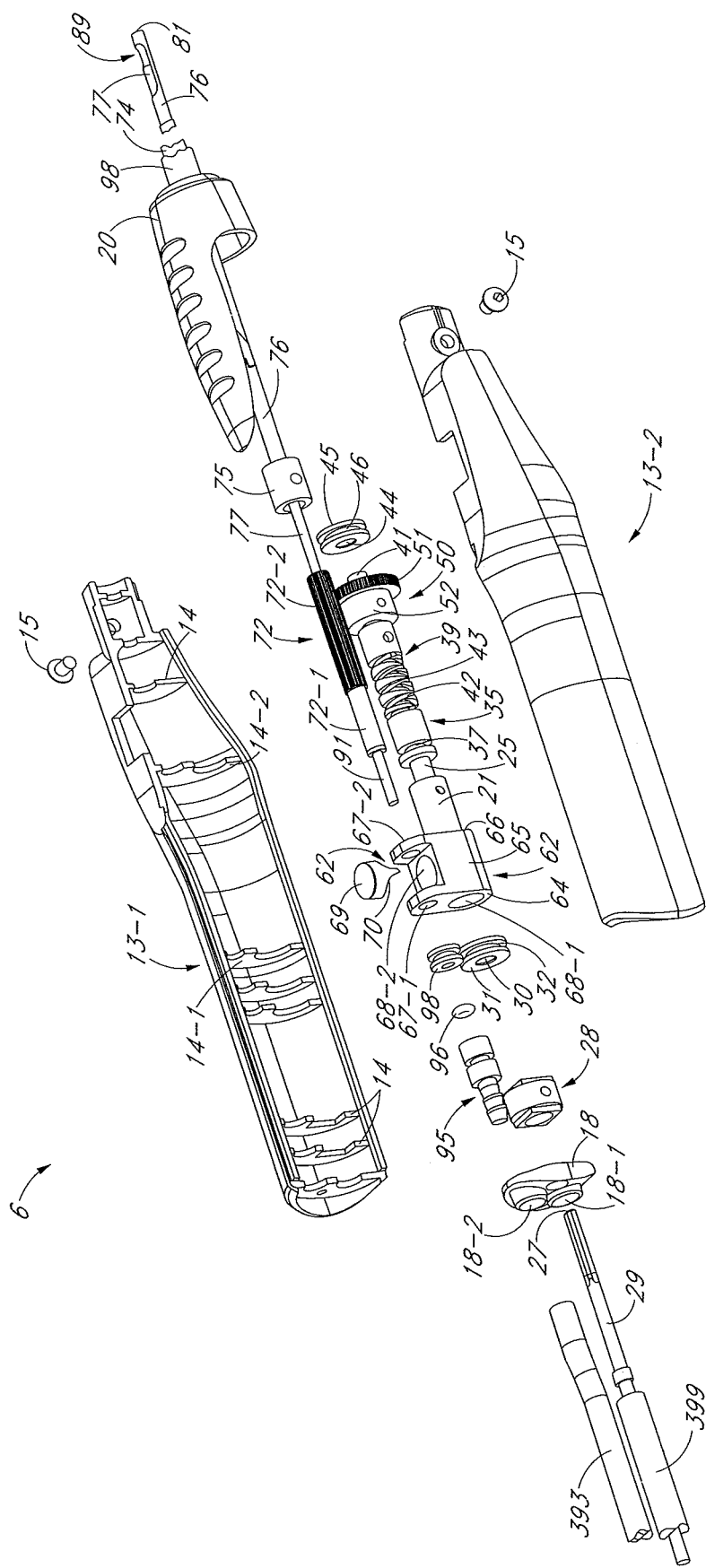
Figure 2C:
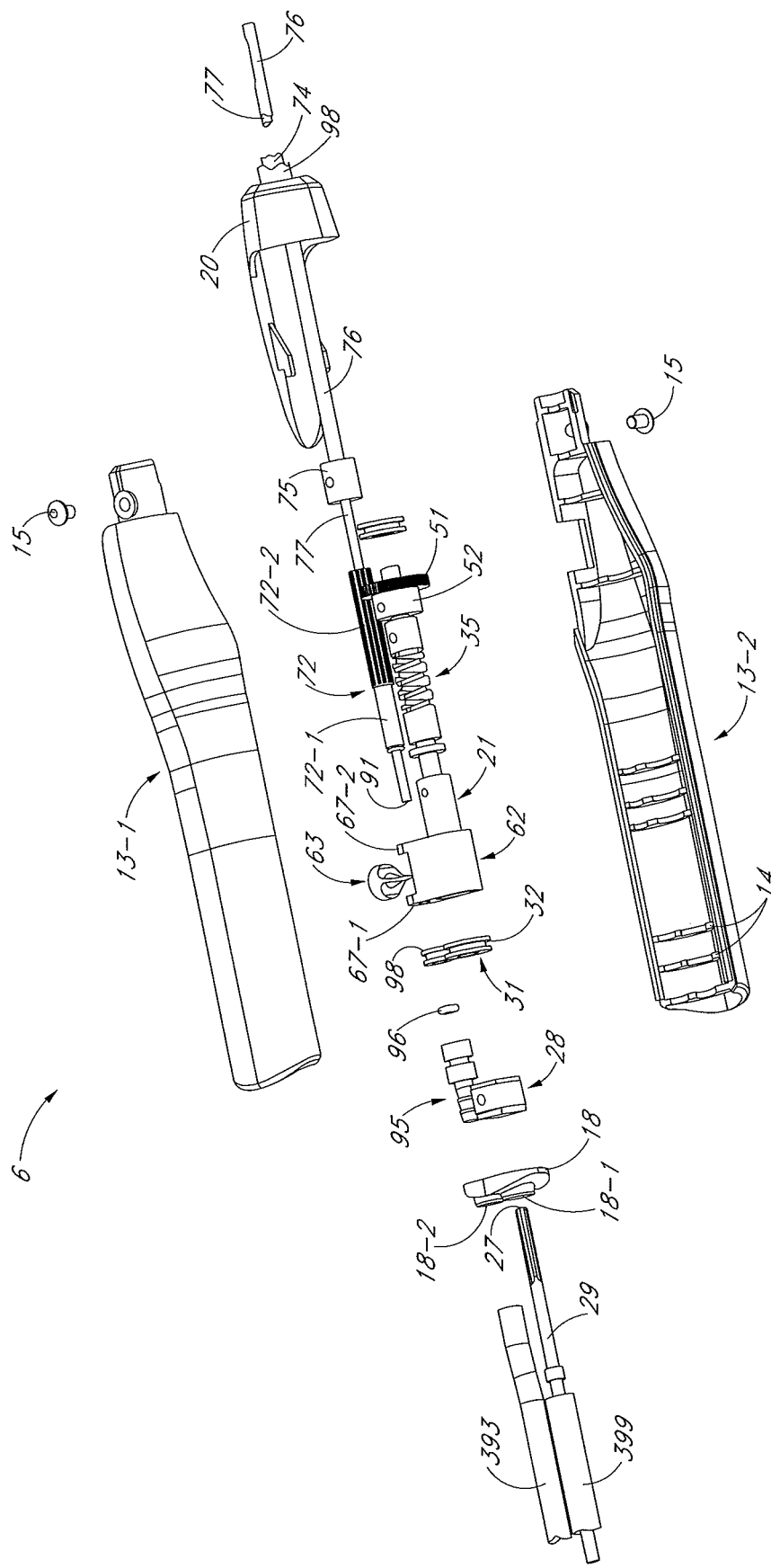
Figure 2D:
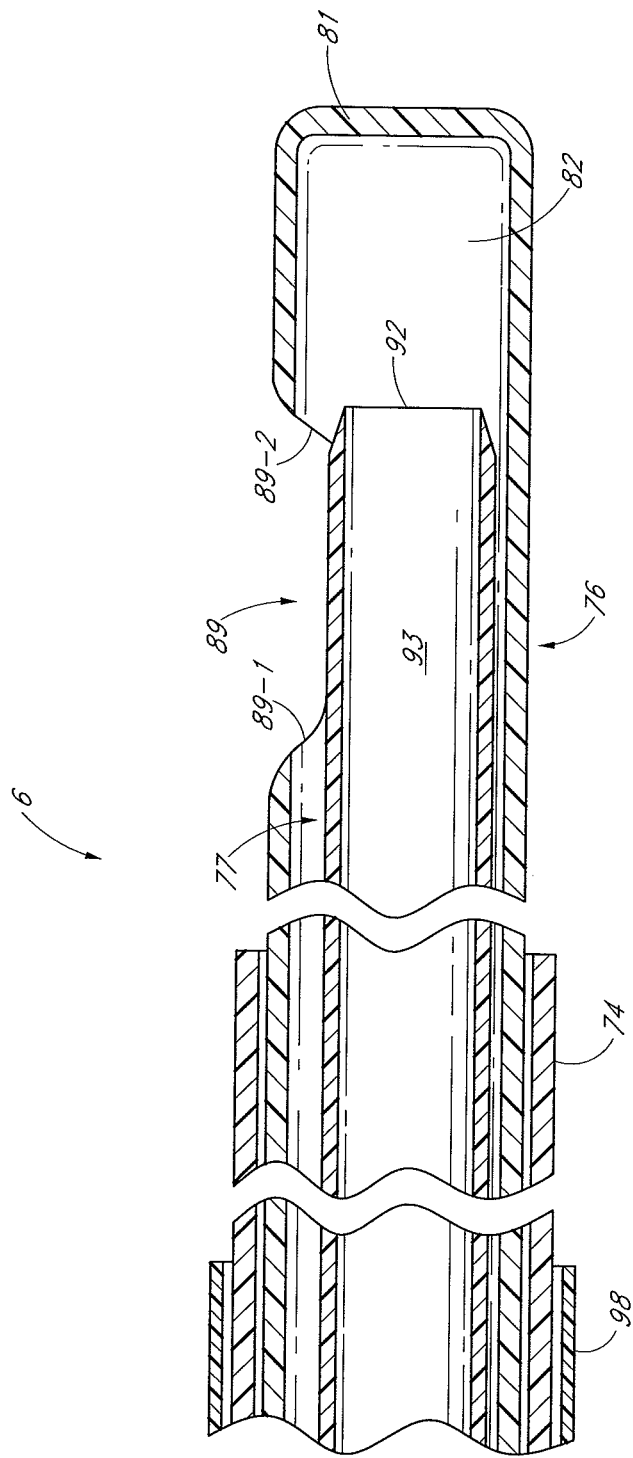
Figure 4A:
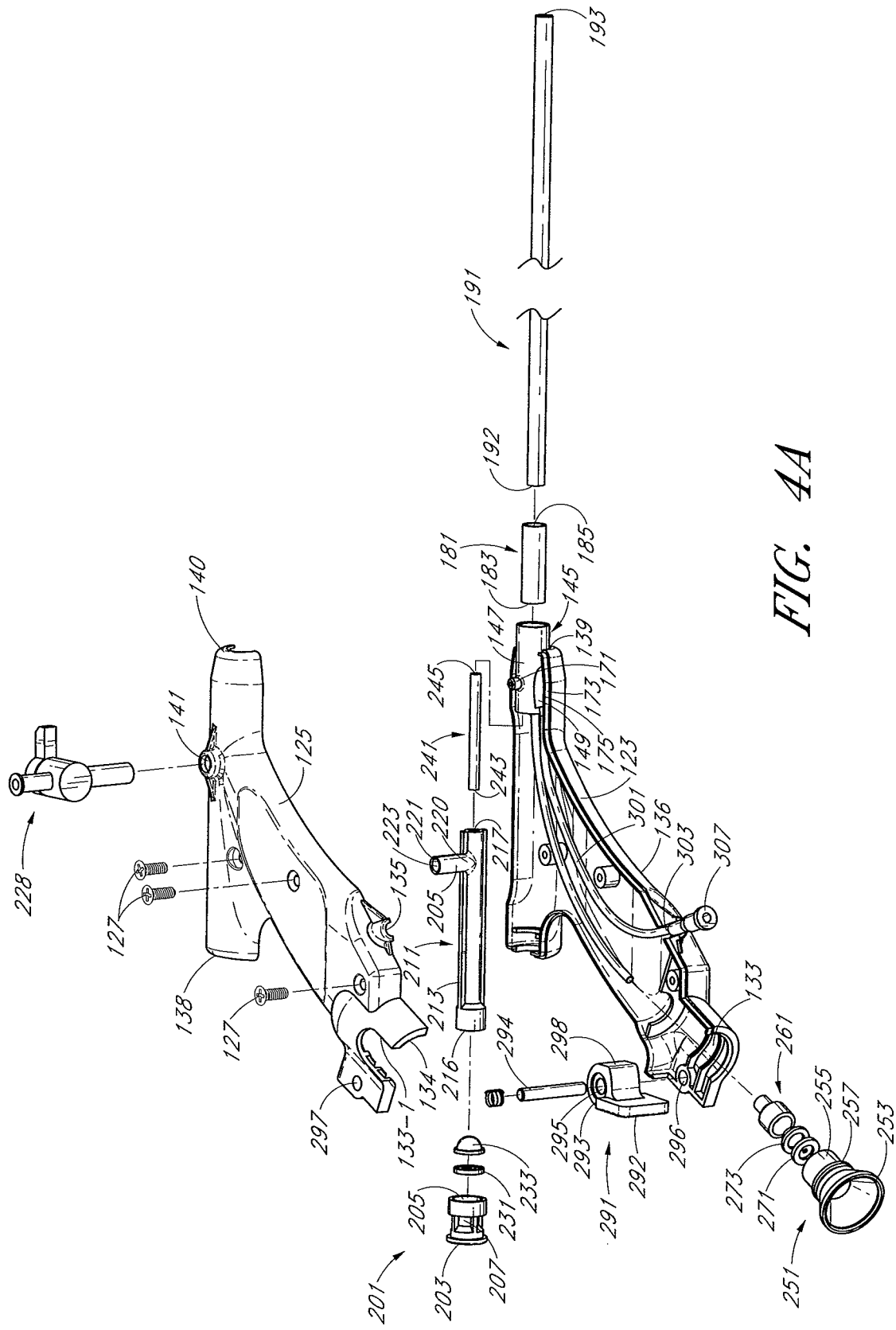
FIGS. 4(a) and 4(b) are exploded perspective views of the introducer device shown in FIG. 1.
Figure 4B:
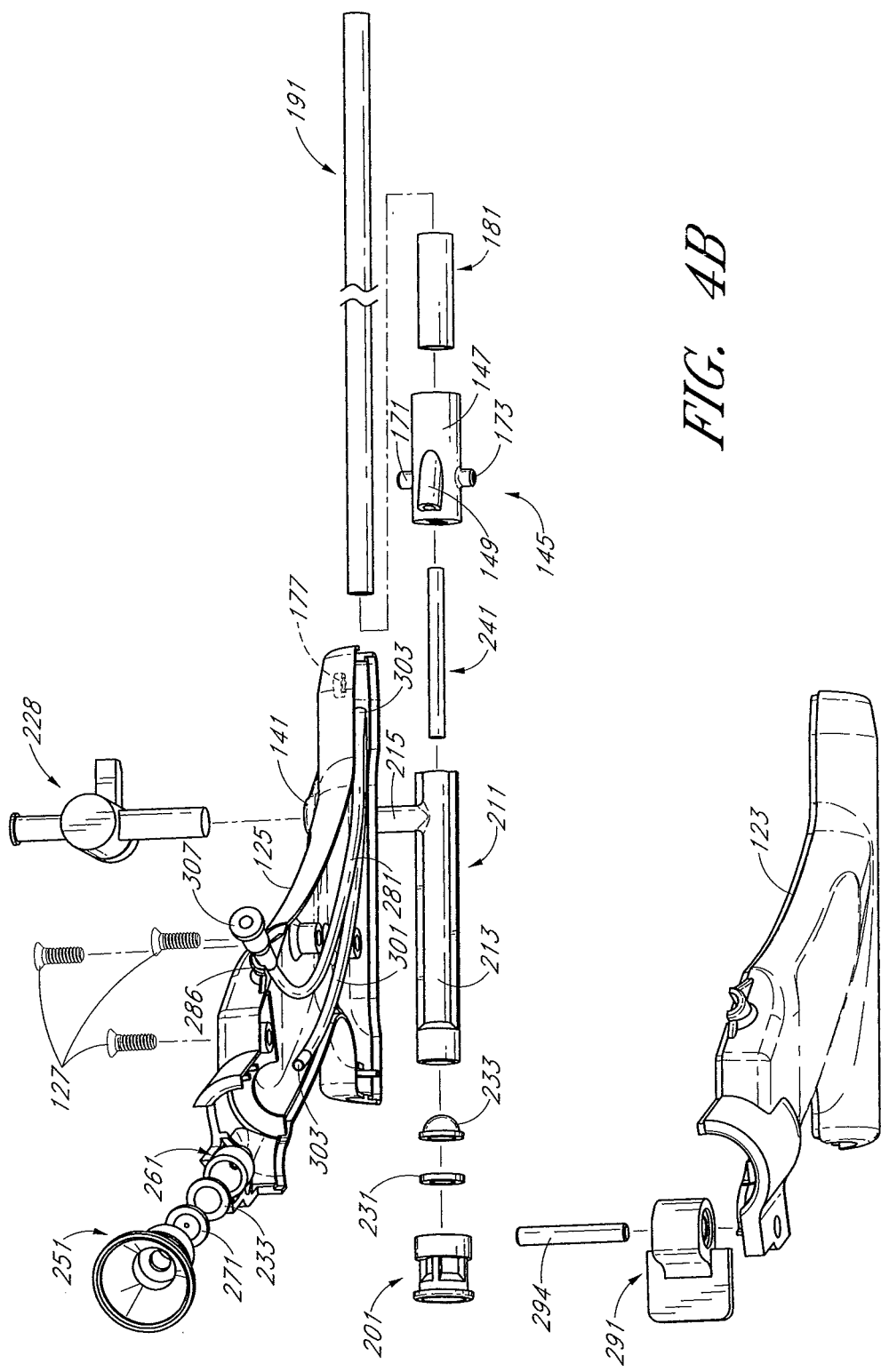
Figure 5:
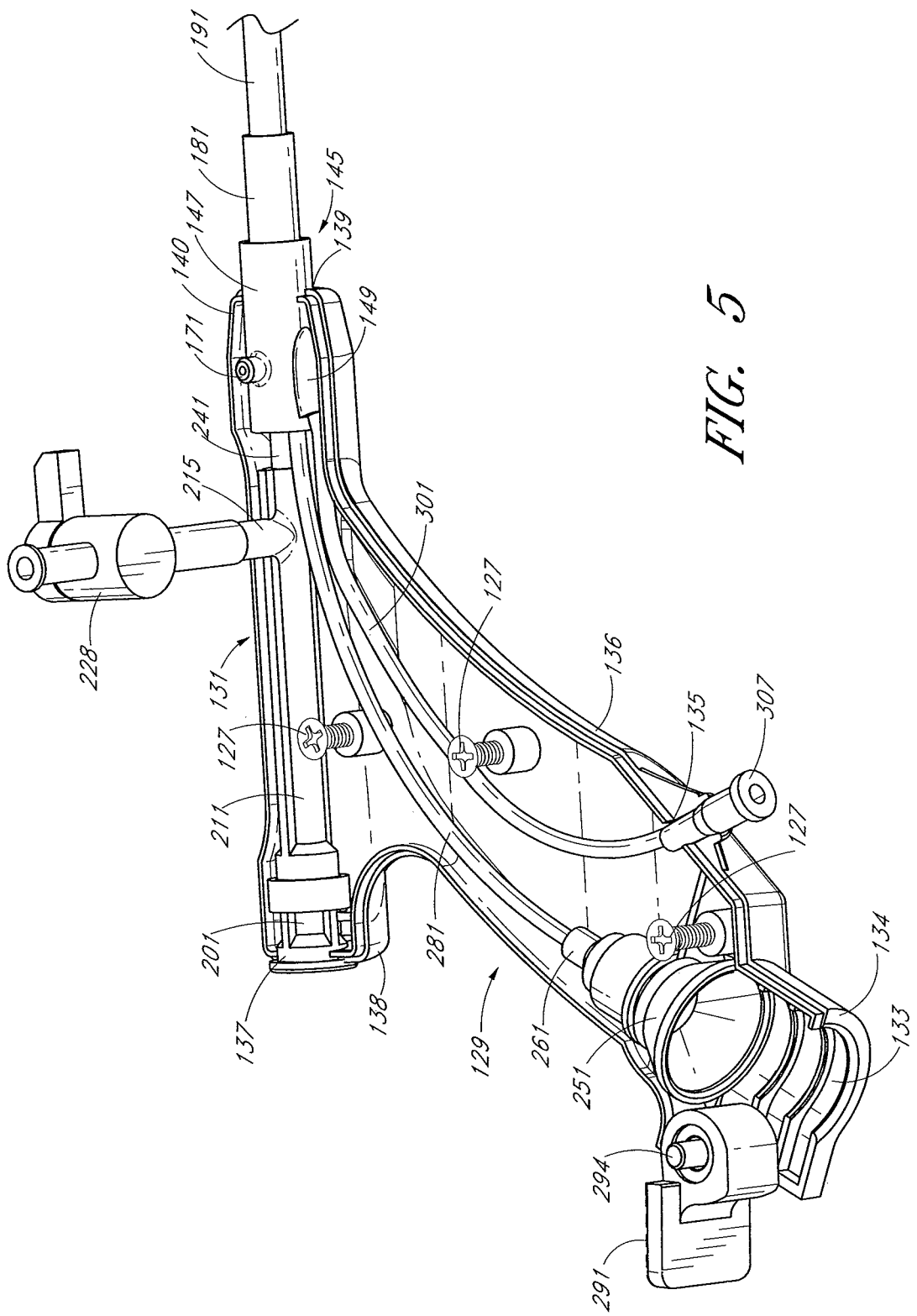
FIG. 5 is a right perspective view of the introducer device shown in FIG. 1, with the right half of the housing removed.
Figure 6:
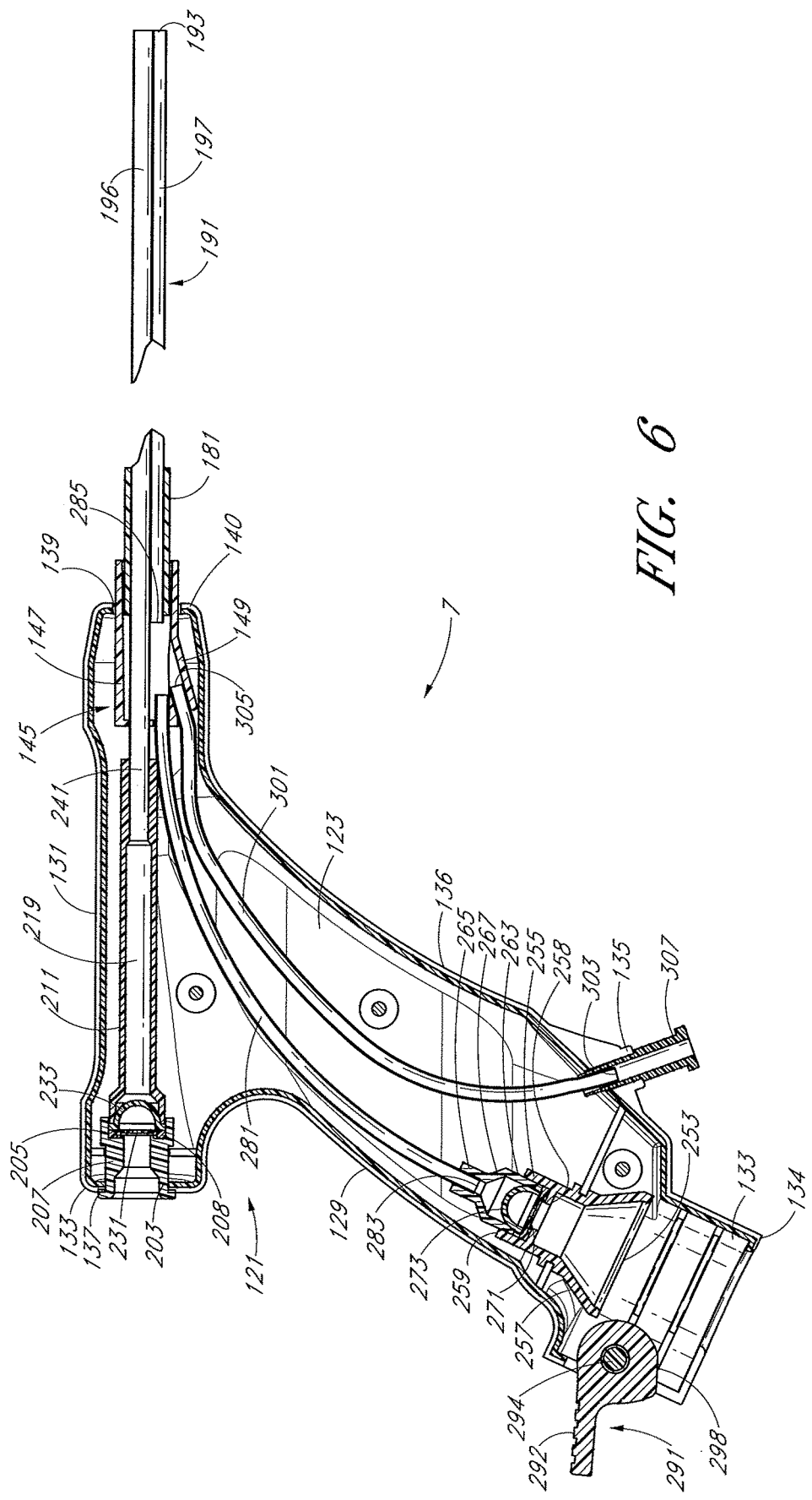
FIG. 6 is a longitudinal section view of the introducer device shown in FIG. 1.
Figure 7:
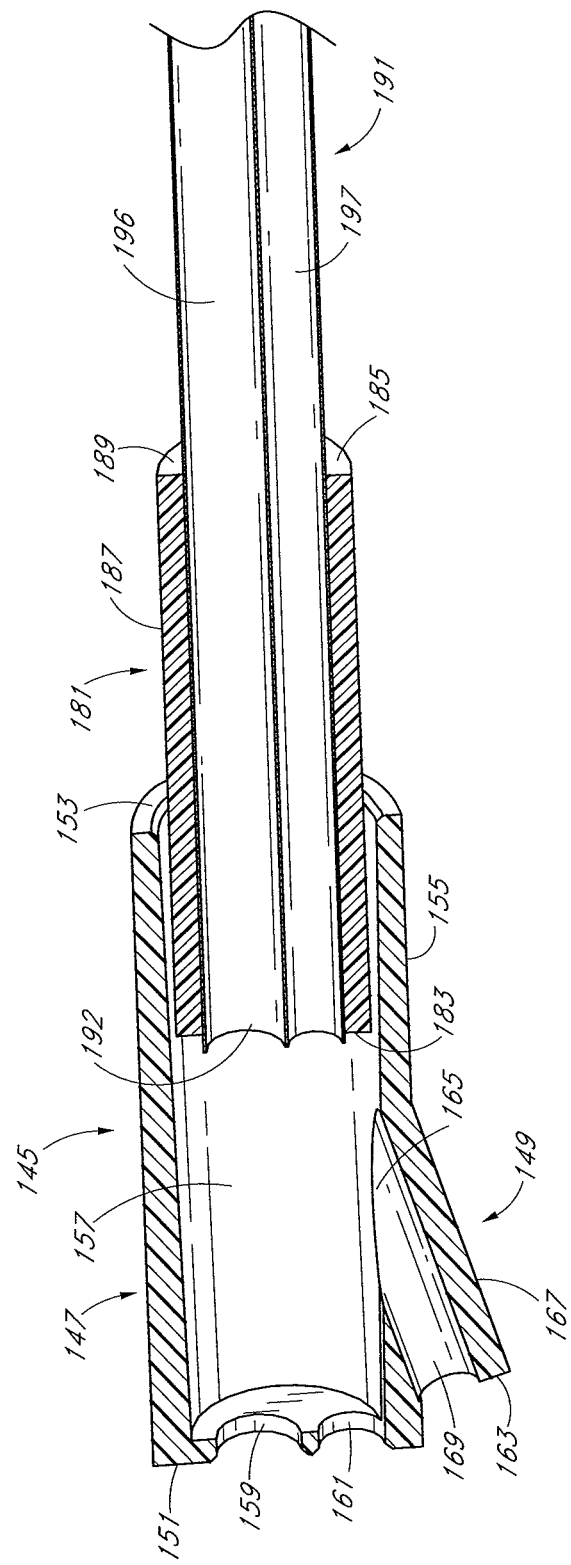
FIG. 7 is an enlarged fragmentary perspective view, shown in section, of the introducer device shown in FIG. 1, with only the manifold, strain relief and sheath being shown.

Referring now to FIG. 1, there is shown a partially exploded perspective view of one embodiment of a tissue removal system, the tissue removal system being constructed according to the teachings of the present invention and being represented generally by reference numeral 5.

System 5 is particularly well-suited for removing uterine fibroids and other abnormal gynecological tissues. However, it should be understood that system 5 is not limited to such a use and may be used in other anatomies that may be apparent to those of ordinary skill in the art.

System 5 may comprise a tissue removal device (or morcellator) 6, an introducer device 7, a flexible hysteroscope 8, a fluid supply 9, a vacuum assembly 10, and a motor drive assembly 11.

Referring now to FIGS. 2(a) through 2(d), tissue removal device 6 may be seen in greater detail. Device 6 may comprise complementary left and right housing halves 13-1 and 13-2, respectively, each of which may be made of a rigid polymer or other suitable material. Halves 13-1 and 13-2 may be joined together, for example, with screws 15 to form an elongated hollow housing 13 comprising a rounded side wall 16, an open proximal end 17, and an open distal end 19. Housing 13 may be bent or otherwise ergonomically shaped to fit comfortably in the hand of a user. A proximal cap 18 may be mounted in proximal end 17, cap 18 being shaped to include a pair of lumens 18-1 and 18-2. Lumen 18-1 may be used to receive, for example, an external drive shaft, and lumen 18-2 may be used to receive, for example, a vacuum tube. A distal cap 20 may be mounted in distal end 19, cap 20 being shaped to include a lumen, which may be used to receive, for example, a pair of coaxial cutting tubes.

A plurality of ribs 14 may be integrally formed and appropriately positioned along the respective interior surfaces of halves 13-1 and 13-2, ribs 14 providing structural reinforcement to housing 13 and being used to align certain of the mechanical components that are positioned within housing 13.

Device 6 may further comprise an internal drive shaft 21 adapted for rotation about its longitudinal axis. Shaft 21, which may be an elongated unitary structure made of a suitably rigid metal or polymer, may be shaped to include a proximal end 23 and a distal end 25. Proximal end 23 of shaft 21 may be coaxially mounted over and fixed to the distal end 27 of an external drive shaft 29, external drive shaft 29 being inserted through a retainer 28 mounted in housing 13. In this manner, the rotation of shaft 21 may be mechanically coupled to the rotation of shaft 29. Distal end 25 of shaft 21 may be inserted through an opening 30 in an annular bushing 31, which bushing 31 may be matingly mounted on a rib 14-1 via a circumferential slot 32 provided in bushing 31.

Device 6 may further comprise a translation drive shaft 35 adapted for rotation about its longitudinal axis. Shaft 35, which may be an elongated unitary structure made of a suitably rigid metal or polymer, may be shaped to include a proximal end 37, an intermediate portion 39, and a distal end 41. Proximal end 37 of shaft 35 may be coaxially mounted over and fixed to the distal end 25 of internal drive shaft 21. In this manner, the rotation of shaft 35 may be mechanically coupled to the rotation of shaft 21. Intermediate portion 39 may be shaped to include a double helical portion comprising a right-handed threaded helical channel 42 and a left-handed threaded helical channel 43. Helical channels 42 and 43 may have identical or different pitches but preferably have identical pitches. Helical channels 42 and 43 may be smoothly blended together at their respective ends to form a continuous groove so that there may be a smooth transition from one helical channel to the other. Distal end 41 of shaft 35 may be appropriately dimensioned to be received within an opening 44 in an annular bushing 45, which bushing 45 may be matingly mounted on a rib 14-2 via a circumferential slot 46 provided in bushing 45. It should be noted that, although shaft 35 is adapted for rotation, shaft 35 is translationally stationary.

Device 6 may further comprise a gear assembly 50 adapted for rotation about its longitudinal axis. Gear assembly 50, which may be an elongated unitary structure made of a suitably rigid metal or polymer, may be shaped to include a proximal spur gear 51 and a distal tube portion 52. Gear assembly 50 may be coaxially mounted over intermediate portion 39 of shaft 35 in an area between the double helical portion and distal end 41, and gear assembly 50 may be fixed to shaft 35 using a pin inserted radially through tube portion 52 and into an opening provided in shaft 35. In this manner, the rotation of spur gear 51 may be mechanically coupled to the rotation of shaft 35.

Device 6 may further comprise an oscillating translation assembly 61. Translation assembly 61, in turn, may comprise a carriage 62 and a channel engagement member 63. Carriage 62, which may be a unitary structure made of a suitably rigid metal or polymer, may be shaped to include a proximal portion 64, an intermediate portion 65, and a distal portion 66. The tops of proximal portion 64 and distal portion 66 may extend beyond the top of intermediate portion 65 and may be shaped to include loops 67-1 and 67-2, respectively, loops 67-1 and 67-2 being aligned with one another. A longitudinal bore 68-1 may be provided near the bottom of carriage 62, bore 68-1 being appropriately dimensioned to coaxially receive intermediate portion 39 of shaft 35 while permitting intermediate portion 39 to rotate freely therewithin. Channel engagement member 63, which may be a unitary structure made of a suitably rigid metal or polymer, may be shaped to include a base 69 and a pawl 70. Base 69 may be disposed in an opening 68-2 that may extend downwardly from the top of intermediate portion 65 into communication with bore 68-1, with pawl 70 traveling within the double helical portion of shaft 35. In this manner, as shaft 35 rotates, pawl 70 may continuously travel back and forth through the double helical portion of shaft 35, thereby causing carriage 62 to oscillate translationally. As can be appreciated, the speed at which carriage 62 oscillates translationally may be varied, for example, by varying the translational length of the double helical portion of shaft 35, the angles of channels 42 and 43, the rotational speed of shaft 29, etc. As will be discussed further below, it may be desirable to operate device 6 so that carriage 62 oscillates translationally at about 2.8 cycles/second.

Device 6 may further comprise a shaft 72 adapted for rotation about its longitudinal axis. Shaft 72, which may be an elongated, unitary, tubular structure made of a suitably rigid metal or polymer, may be shaped to include a proximal portion 72-1 and a distal portion 72-2. Proximal portion 72-1 may be inserted through loops 67-1 and 67-2 of carriage 62 and may freely rotate relative to loops 67-1 and 67-2. Distal portion 72-2 may be in the form of an elongated spur gear. Distal portion 72-2 may be engaged with spur gear 51 of gear assembly 50 so that the rotation of spur gear 51 causes the rotation of shaft 72. Distal portion 72-2 may be elongated so that it may maintain engagement with spur gear 51 even as distal portion 72-2 moves translationally relative to spur gear 51. The speed at which distal portion 72-2 rotates (and, therefore, the speed at which shaft 72 rotates) may be the same as or different than the speed at which spur gear 51 rotates, depending, for example, on the relative diameters of the two gears (the ratio of the rotational speeds of the two gears being inversely proportional to the ratio of the diameters of the two gears). Consequently, by appropriately dimensioning spur gear 51 and distal portion 72-2, one can achieve a desired rotational speed, even where the rotational speed of the external drive shaft is fixed. For example, in the embodiment shown, distal portion 72-2 has a diameter that is one-fourth the diameter of spur gear 51 and, therefore, rotates four times as fast as gear 51. Therefore, if the external drive shaft has a speed of rotation of about 1500 rpm, gear 51 would rotate at 1500 rpm and distal portion 72-2 would rotate at 6000 rpm. As can be appreciated, the rotational speed of distal portion 72-2 does not depend on the interaction of translation assembly 61 with the double helical portion of shaft 35; consequently, distal portion 72-2 may attain higher or lower rotational speeds than would be possible based on the requirements of a desired translational speed. Notwithstanding the above, shaft 72 is translationally coupled to carriage 62. Consequently, as carriage 62 oscillates translationally, so does shaft 72.

Device 6 may further comprise a strain relief member 74, which may be a unitary tubular structure made of a rigid polymer or metal. The proximal end of strain relief member 74 may be fixedly mounted in a retainer 75, which may be mounted at the distal end of housing 13, with the distal end of strain relief 74 extending distally from housing 13 for a short distance, such as, for example, approximately 2 inches.

Device 6 may further comprise a cutting mechanism. In the present embodiment, the cutting mechanism may comprise an outer tubular member 76 and an inner tubular member 77, inner tubular member 77 moving rotationally and, at the same time, oscillating translationally relative to outer tubular member 76 in the manner to be described further below. Outer tubular member 76, which may be a unitary structure made of stainless steel or another similarly suitable material, may be shaped to include an open proximal end, a closed distal end 81, and a lumen 82 extending from open proximal end 79 to a point just prior to closed distal end 81. Member 76 may be coaxially mounted within strain relief member 74, with the proximal end of member 76 disposed within the proximal end of strain relief member 74 and with distal end 81 of member 76 extending distally beyond the distal end of strain relief member 74 for an extended distance, such as, for example, five inches. The proximal end of member 76 may be fixed within retainer 75.

Outer tubular member 76 may be further shaped to include a resection window 89 into which tissue may be captured and drawn, window 89 being located proximate to distal end 81, such as, for example, 0.25 inch from distal end 81. Window 89 may be shaped to include a proximal end 89-1 and a distal end 89-2. Proximal end 89-1 may slope gradually proximally, and distal end 89-2 may slope gradually distally. More specifically, window 89 may have a length of approximately 0.55 inch, proximal end 89-1 may be a radial end having a radius of curvature of, for example, 0.085 inch, and distal end 89-2 may be a radial end having a radius of curvature of, for example, 0.150 inch. Window 89 may extend over a substantial portion of the circumference of tubular member 76, such as, for example, about 60% of the circumference.

Outer tubular member 76 may have an outer diameter less than about 5.5 mm. However, in order to reduce the risk of injury to the patient and in order to obviate the need for anesthesia to be administered to the patient, outer tubular member 76 preferably has an outer diameter less than about 5 mm, more preferably less than 4 mm, even more preferably less than 3 mm, and still even more preferably less than 2 mm. However, should device 6 be used in an operating room setting where general anesthesia is available, the diameter of the outer tubular member 76 could be increased to maximize tissue removal. In such a case, outer tubular member 76 could have a diameter generally less than about 12 mm, preferably less than about 11 mm, and for certain applications less than 10 mm. Depending on the particular clinical application, outer tubular member 76 could be constructed having an outer diameter of no more than about 9 mm, in some applications less than about 8 mm, preferably less than 7 mm, and more preferably less than 6 mm where OD is desirably minimized.

Inner tubular member 77, which may be an elongated unitary structure made of stainless steel or another similarly suitable material, may be shaped to include a proximal end 91, a distal end 92, and a longitudinal lumen 93. Distal end 92 may be shaped to include an external bevel, such as, for example, an external bevel of approximately 20 degrees. An intermediate length of tubular member 77 may be coaxially received within shaft 72 and may be fixedly coupled to shaft 72 for translational and rotational movement therewith. Proximal end 91 of tubular member 77 may be slideably mounted within a vacuum tube connector 95, which may, in turn, be coupled to a vacuum tube 393 inserted through lumen 18-2 of cap 18. An O-ring 96 may be mounted within connector 95 to maintain a good seal with tubular member 77. An annular bushing 98 mounted within housing 13 may be used to receive tubular member 77 and to maintain its alignment.

Tubular members 76 and 77 may be arranged so that, when tubular member 77 is in a fully retracted (i.e., proximal) position, distal end 92 of tubular member 77 may be withdrawn sufficiently to permit tissue to enter window 89 (preferably with distal end 92 of tubular member positioned proximal to window 89), and so that, when tubular member 77 is in a fully advanced (i.e., distal) position, distal end 92 of tubular member 77 may be positioned distally of distal end 89-2 of window 89. In this manner, as tubular member 77 is moved translationally and rotationally past window 89, tissue within window 89 may be sheared. To promote such a shearing of tissue, the outer diameter of inner tubular member 77 may be just slightly less (e.g., about 0.002 inch) than the inner diameter of outer tubular member 76.

It has been shown that the thermal energy created by the contact of the rotating inner tube 77 and outer tube 76 can lead to galling where the two tubular members fuse together. To mitigate that galling risk, the outer surface of inner tube 77 has been covered with a low friction, low abrasion coating (i.e., Titanium Nitride). Alternatively, the coating can be carried by the inner surface of the outer tube 76. The coating may have a Rockwell C hardness of at least about 50, preferably at least about 60 and in some devices at least about 70.

Device 6 may further comprise an indicator sleeve 98. Sleeve 98, which may be an elongated tubular member made of a material that is easily distinguishable visually from strain relief member 74, may be coaxially mounted over strain relief member 74 and fixedly mounted thereto, with a proximal end 98-1 of sleeve 98 lying flush against the distal end of housing 13. An example of a material suitable for use as sleeve 98 may be a white or colored length of shrink-wrap material. Sleeve 98 may be dimensioned so that, when device 6 is inserted into introducer device 7, distal end 98-2 of sleeve 98 is visible to a user until distal end 81 of device 6 is advanced beyond the distal end of introducer 7. In other words, distal end 98-2 may be used to indicate when distal end 81 of device 6 lies flush with the distal end of introducer 7. In this manner, a user may safely control the position of the distal end of device 6 and, therefore, keep it within introducer 7 when inserting device 6 into a patient, thereby reducing the risks for lacerations and perforations during introduction of device 6.

Referring now to FIGS. 3 through 7, introducer 7 may comprise a housing 121. Housing 121, in turn, may comprise a left handle half 123 and a right handle half 125. Left handle half 123 and right handle half 125, which may be molded or otherwise fabricated from a rigid polymer or other suitable material, may be joined by a plurality of screws 127. Instead of being joined by screws 127, left handle half 123 and right handle half 125 may be joined using a suitable adhesive, crush pins, or may be welded together ultrasonically or otherwise. Left handle half 123 and right handle half 125 jointly define a hollow, gun-shaped structure comprising a handle portion 129 and a barrel portion 131. Handle portion 129 may be shaped to include an opening 133 provided at its bottom end 134 and an opening 135 provided along its distal face 136 near bottom end 134. A slot 133-1 may be provided in right handle half 125, slot 133-1 extending from opening 133 towards barrel portion 131 for a short distance. Barrel portion 131 may be shaped to include an opening 137 provided at its proximal end 138 and an opening 139 provided at its distal end 140. In addition, barrel portion 131 may be shaped to include a transverse opening 141 provided in right handle half 125 at a location intermediate to proximal end 138 and distal end 140.

The interior surfaces of left handle half 123 and right handle half 125 may shaped to include complementary sets of ribs (not shown). Such ribs may provide structural reinforcement to left handle half 123 and right handle half 125 and may help to maintain the correct positioning and alignment of the components positioned within housing 121.

Introducer 7 may further comprise a manifold 145. Manifold 145, which may be molded or otherwise fabricated from a rigid polymer or other suitable material, may be a unitary, branched structure shaped to include a main tubular member 147 and a side tubular member 149. Main member 147 may comprise a proximal end 151, an open distal end 153, a side wall 155, and a longitudinal lumen 157. Proximal end 151 of main member 147 may be shaped to include a top opening 159 of comparatively greater diameter and a bottom opening 161 of comparatively smaller diameter. Side member 149 may comprise an open proximal end 163, an open distal end 165, a side wall 167, and a longitudinal lumen 169. Lumen 169 of side member 149 may be in fluid communication with lumen 157 of main member 147 through open distal end 165.

Manifold 145 may be coupled to housing 121 using a pair of pins 171 and 173 that may extend from side wall 155 and that may be received within hollow embossments 175 and 177, respectively, provided on the interior faces of left handle half 123 and right handle half 125, respectively. With manifold 145 thus coupled to housing 121, proximal end 151 of manifold 145 may be positioned in barrel portion 131, with side wall 155 tightly fitting within opening 139 and with distal end 153 of manifold 145 extending distally a short distance beyond distal end 140.

Introducer 7 may further comprise a strain relief member 181. Strain relief member 181, which may be molded or otherwise fabricated from a rigid polymer or other suitable material, may be a unitary tubular structure shaped to include an open proximal end 183, an open distal end 185, a side wall 187, and a longitudinal lumen 189. Strain relief member 181 may be partially inserted into lumen 157 of manifold 145 and may be tightly fitted within lumen 157 and fixedly secured thereto using a suitable adhesive or the like, with proximal end 183 of strain relief member 181 being positioned just distal to open distal end 165 of side member 149 and with distal end 185 of strain relief member 181 extending distally a short distance beyond distal end 153 of main member 147.

Figure 8:
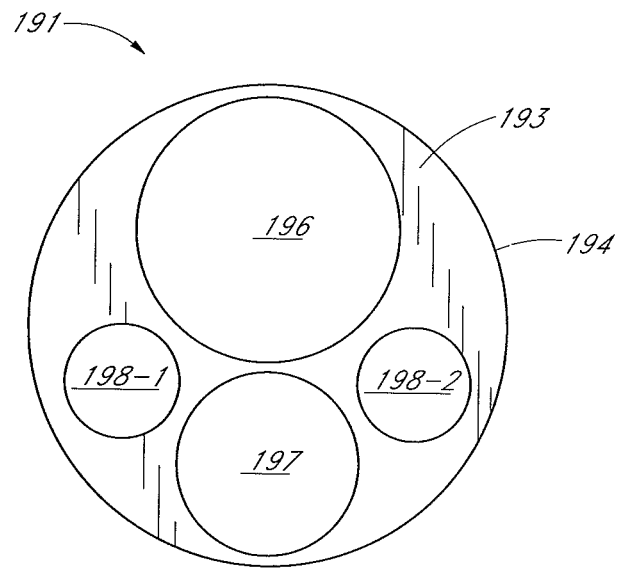
FIG. 8 is an enlarged distal end view of the multi-lumen sheath of the introducer device shown in FIG. 1.

Introducer 7 may further comprise a sheath 191, which is also shown separately in FIG. 8. Sheath 191, which may be extruded or otherwise fabricated from a suitable polymer, such as nylon 12, may be a rigid, unitary structure shaped to include a proximal end 192, a distal end 193, and a side wall 194. Sheath 191 may be further shaped to include a plurality of longitudinal lumens of fixed shape and size, such lumens including a top lumen 196, a bottom lumen 197, and a pair of side lumens 198-1 and 198-2. As will be discussed further below, top lumen 196 may be used as an instrument lumen, bottom lumen 197 may be used as a visualization lumen, and side lumens 198-1 and 198-2 may be used as inflow fluid supply lumens. (Openings (not shown) may be provided in side wall 194 proximate to distal end 193, such side openings fluidly communicating with side lumens 198-1 and 198-2, for example, to dispense some of the inflow fluid supply conducted distally through side lumens 198-1 and 198-2.) Proximal end 192 of sheath 191 may be partially inserted into lumen 189 of strain relief member 181 and may be tightly fitted within lumen 189 and fixedly secured thereto using a suitable adhesive or the like, with proximal end 192 of sheath 191 flush with proximal end 183 of strain relief member 181 and with distal end 193 of sheath 191 extending distally beyond distal end 185 of strain relief member 181 for several inches.

Sheath 191, which is preferably the only component of introducer 7 that is to be inserted into a patient, may be dimensioned to have an outer diameter of about 5.5 mm, with lumen 196 having a diameter of about 3 mm, lumen 197 having a diameter of about 2 mm, and lumens 198-1 and 198-2 each having a diameter of about 1.33 mm. It can be further stated the ratio of the outer diameter to the working channel is an exemplary metric of introducer efficiency. It can be seen that the optimal ratio would be about 1.0, preferably no more than about 2.1 and more preferably no more than about 1.9. In the case provided herein, the ratio of these diameters is about 1.83 while predicate systems have ratios of 2.25. By thus dimensioning sheath 191, if sheath 191 is inserted through the cervix of a patient, the risk of injury to the patient and the need for anesthesia to be administered to the patient may be minimized. However, it should be understood that the above dimensions for sheath 191 are merely exemplary and may be varied depending upon how introducer 7 is to be used.

Introducer 7 may further comprise an instrument guide assembly mounted within housing 121 for providing a continuous channel aligned with lumen 196 into which tissue removal device 6 may be inserted. The instrument guide assembly may comprise a guide body 201. Body 201, which may be molded or otherwise fabricated from a rigid polymer or other suitable material, may be a unitary tubular structure shaped to include a proximal portion 203, a distal portion 205 and an intermediate portion 207. Intermediate portion 207 may be reduced in inner diameter and in outer diameter relative to proximal portion 203 and distal portion 205 so that an annular seat 208 is formed within body 201 at the juncture of intermediate portion 207 and distal portion 205. The interior surface of body 201 may taper inwardly from proximal portion 203 to intermediate portion 207 to facilitate insertion of device 6 into intermediate portion 207 and to delimit the extent to which device 6 may be inserted into body 201.

Body 201 may be tightly fitted within opening 137 of housing 121 and fixedly secured thereto using a suitable adhesive or the like, with distal portion 205 and intermediate portion 207 of body 201 being positioned within barrel portion 131 of housing 121 and with proximal portion 203 of body 201 extending through opening 137 and continuing proximally for a short distance beyond proximal end 138 of housing 121.

The instrument guide assembly may further comprise a sleeve 211. Sleeve 211, which may be molded or otherwise fabricated from a rigid polymer or other suitable material, may be a unitary, branched structure shaped to include a main tubular member 213 and a side tubular member 215. Main member 213 may comprise an open proximal end 216, an open distal end 217, and a longitudinal lumen 219. Proximal end 216 of main member 213 may be shaped to be tightly fitted within distal portion 205 of body 201 and may be bonded thereto using a suitable adhesive. Side member 215 may comprise an open proximal end 220, an open distal end 221 and a longitudinal lumen 223. Lumen 223 of side member 215 may be in fluid communication with lumen 219 of main member 213 through open proximal end 220. Distal end 221 of side member 215 may extend through opening 141 provided in right handle half 125 of housing 121 and may be coupled to a valve 228. Valve 228 may be an actively-controlled valve, such as a stopcock valve, or a passively-controlled valve, such as a spring-activated ball valve. Valve 228 may be connected at its output end to a length of tubing (not shown), as well as to a fluid receptacle (not shown), for conducting, as well as collecting, for example, outflow fluid passing through valve 228, for example, when device 6 is not present within introducer 7.

Figure 9:
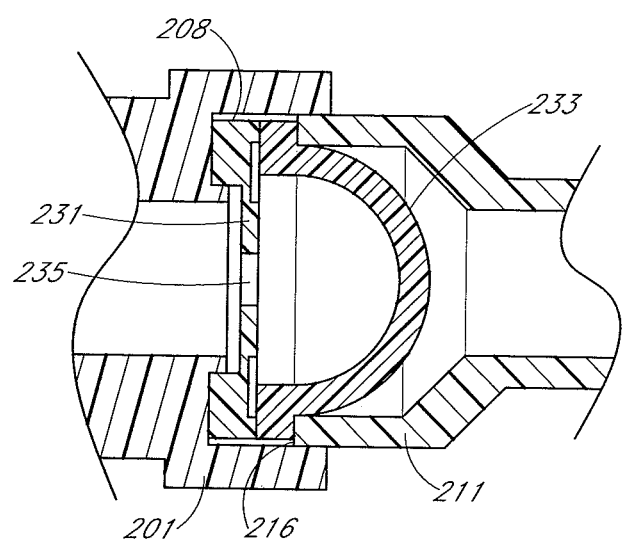
FIG. 9 is an enlarged fragmentary view of the instrument guide assembly of the introducer device shown in FIG. 1.

The instrument guide assembly may further comprise the combination of a seal 231 and a valve 233. Seal 231 and valve 233 may be elastomeric members securely positioned between seat 208 of body 201 and proximal end 216 of sleeve 211 (see FIG. 9). Seal 231, which may be located proximally relative to valve 233, may include a central opening 235. Opening 235 may be appropriately dimensioned so that, when device 6 is inserted therethrough, fluid may not readily pass proximally through seal 231 around the outside of device 6. Valve 233, which may be shaped to include a dome having a cross-slit at its top, may be designed so that, in the absence of device 6 being inserted therethrough, fluid may not readily pass proximally therethrough.

The instrument guide assembly may further comprise a tube 241. Tube 241, which may be a rigid hypotube made of stainless steel or the like, may comprise a proximal end 243 and a distal end 245. Proximal end 243 may be fixedly mounted within lumen 219 of sleeve 211 using a suitable adhesive or the like. Distal end 245 of tube 241 may be tightly fitted within lumen 196 of sheath 191 and may be secured therewithin using a suitable adhesive or the like.

Introducer 7 may further comprise a visualization guide assembly mounted within housing 121 for providing a continuous channel aligned with lumen 197 into which hysteroscope 8 may be inserted. The visualization guide assembly may comprise a guide body 251. Body 251, which may be molded or otherwise fabricated from a rigid polymer or other suitable material, may be a unitary tubular structure shaped to include a proximal portion 253 of comparatively greater diameter, a distal portion 255 of comparatively smaller diameter, and an intermediate portion 257 tapering in diameter from proximal portion 253 to distal portion 255. Body 251 may be disposed within handle portion 129 of housing 121, with proximal portion 253 spaced inwardly a short distance from opening 133 and with distal portion 255 facing towards barrel portion 131. Proximal portion 253 may be tightly fitted between and fixedly secured to left handle half 123 and right handle half 125 of housing 121 using adhesive or other suitable means. As will be discussed further below, proximal portion 253 may be appropriately dimensioned to receive the proximal portion of hysteroscope 8, with intermediate portion 257 of body 251 being appropriately dimensioned to serve as a stop to limit the extent to which hysteroscope 8 may be inserted into body 251. An annular seat 258 may be provided within distal portion 255 and may be spaced proximally relative to distal end 259 of distal portion 255.

The visualization guide assembly may further comprise a guide connector 261. Guide connector 261, which may be molded or otherwise fabricated from a rigid polymer or other suitable material, may be a unitary tubular structure shaped to include a proximal portion 263 of comparatively greater diameter, a distal portion 265 of comparatively smaller diameter, and an intermediate portion 267 tapering in diameter from proximal portion 263 to distal portion 265. Proximal portion 263 may be shaped to be tightly fitted within distal portion 255 of body 251 and may be bonded thereto using a suitable adhesive.

The visualization guide assembly may further comprise the combination of a seal 271 and a valve 273. Seal 271 and valve 273 may be elastomeric members securely positioned between seat 258 of body 251 and proximal portion 263 of connector 261. Seal 271, which may be located proximally relative to valve 273, may include a central opening appropriately dimensioned so that, when hysteroscope 8 is inserted therethrough, fluid may not readily pass proximally through seal 271 around the outside of hysteroscope 8. Valve 273, which may be shaped to include a dome having a cross-slit at its top, may be designed so that, in the absence of hysteroscope 8 being inserted therethrough, fluid may not readily pass proximally therethrough.

The visualization guide assembly may further comprise a tube 281. Tube 281, which may be a flexible unitary member fabricated from a suitable polymer or other material, may comprise a proximal end 283, a distal end 285, and a lumen 286. Proximal end 283 may be fixedly mounted within distal portion 265 of connector 261 using a suitable adhesive or the like. Distal end 285 of tube 281 may be tightly fitted within lumen 197 of sheath 191 and may be secured therewithin using a suitable adhesive or the like. Lumen 286 may be appropriately dimensioned so that the distal portion of hysteroscope 8 may be inserted thereinto and, in this manner, guided by tube 281 to lumen 197.

Introducer 7 may further comprise a mechanism for reversibly coupling hysteroscope 8 to the visualization guide assembly. This mechanism may comprise a cam lock 291. Lock 291, which may be fabricated from a rigid polymer or other suitable material, may be a unitary structure shaped to comprise a lever 292 and a fulcrum 293. The fulcrum 293 may be pivotally mounted on housing 121 using a pivot pin 294 inserted through a transverse opening 295 in fulcrum 293 and securely received at its opposite ends in openings 296 and 297 provided in left handle half 123 and right handle half 125, respectively. Fulcrum 293 may comprise a face 298 adapted to frictionally engage the proximal portion of hysteroscope 8 when lever 292 is pivoted towards handle portion 129.

Introducer 7 may further comprise a tube 301. Tube 301, which may be fabricated from a suitable polymer or other material, may be a flexible unitary structure shaped to include a proximal end 303 and a distal end 305. Proximal end 303 may be secured to the distal end of a luer fitting 307 securely mounted within opening 135 of housing 121. Distal end 305 may be positioned within lumen 169 of manifold 145 and may be secured in place using an adhesive or other suitable means. As will be discussed further below, luer fitting 307 may be connected to the output of fluid supply 9. In this manner, fluid dispensed through fitting 307 and into tube 301 may be conducted by tube 301 to manifold 145. Thereafter, the fluid in manifold 145 may flow distally through lumens 198-1 and 198-2 of sheath 191.

Referring back now to FIG. 1, hysteroscope 8, which may be, for example, a conventional flexible hysteroscope, may comprise a proximal portion 311 and a distal portion 313. Proximal portion 311, which may be comparatively rigid, compact in length, and wide in diameter, may comprise an input port 315, an output port 317, and a distal end 318. Distal portion 313, which may be comparatively flexible, elongated in length, and narrow in diameter, may comprise a distal end 319. Hysteroscope 8 may be appropriately dimensioned so that distal end 318 of proximal portion 311 may be received in body 251, with distal portion 313 extending distally through seal 271, valve 273, connector 261, tube 281 and lumen 197 and with distal end 319 positioned at or a short distance beyond distal end 193 of sheath 191. Although not present in the embodiment shown, proximal portion 311 of hysteroscope 8 may be provided with notches or other physical features that may be used to mate with or otherwise engage cam lock 291. Distal end 319 of hysteroscope 8 may be constructed to permit the viewing of objects, such as at 0, 15 or 30 degree angles, relative to the longitudinal axis of distal portion 313. In this manner, by placing hysteroscope 8 in a particular angular orientation, hysteroscope 8 may be used to view the operation of the distal end of device 6. Such an angular orientation may be ensured by orienting hysteroscope 8 so that input port 315 is aligned with and extends through slot 133-1.

Fluid supply 9 may comprise a fluid-containing syringe, a peristaltic pump or another suitable fluid-dispensing device having an output end 321 that may be coupled to luer fitting 307. Fluid supply 9 may comprise automated means (not shown) for dispensing inflow fluid therefrom at a desired rate.

Vacuum assembly 10 may include a specimen collection container 391 and a vacuum source 392. The distal end of an evacuation tube 393 may be connected to the proximal end of vacuum tube connector 95, and the proximal end of evacuation tube 393 may be coupled to a first port 394 of container 391. The distal end of a tube 395 may be coupled to a second port 396 of container 391, and the proximal end of tube 395 may be coupled to vacuum source 392. In this manner, vacuum source 392 may be used to apply suction to device 6, and any withdrawn tissue, liquids or similar matter suctioned through device 6 may be collected in container 391.

Motor drive assembly 11, which may be coupled to a source of electricity, such as an AC wall outlet, using a power cord (not shown), may include a housing 397, in which there may be disposed electronics (not shown) and a motor (not shown). A foot pedal 398 may be coupled to the motor drive assembly by a cable 398-1 and may be used as a power switch to selectively activate or de-activate the motor. The proximal end of shaft 29 may be mechanically coupled for rotation to the motor, and the distal end of shaft 29 may be inserted through opening 18-1 in mounting block 18 and coupled to internal shaft 21 in the manner discussed above. A protective sheath 399 may cover much of the length of shaft 29. Motor drive assembly 11 may further include a vacuum sensor 400, which may be coupled to container 391 by a tube 401, so that the pressure within container 391 may be monitored. In this manner, a sudden increase in vacuum pressure may indicate that a clog has occurred. The presence of a clog may be indicated via an alarm (not shown) located on housing 397. The detection of a clog is often a clear indication that the further operation of device 6 may only aggravate the clogging situation and that a cessation of tissue removal may be necessary. Motor drive assembly 11 may be configured to synchronize actuation of the motor with actuation of vacuum source 392. In this manner, turning on the motor will turn on vacuum source 392 at the same time. Correspondingly, vacuum source 392 may be deactivated whenever the motor is turned off.

In use, distal end 319 of hysteroscope 8 may be inserted first through the visualization guide channel of introducer 7, next through manifold 145, and then through lumen 197 of sheath 191. With hysteroscope 8 thus inserted into introducer 7, cam lock 291 may be used to secure proximal portion 311 of hysteroscope 8 to introducer 7. Input end 315 and output end 317 of hysteroscope 8 may then be coupled to a light source and to a camera, respectively. Alternatively, the camera may be omitted, and output end 317 may be observed directly with the unaided eye. Fluid supply 9 may then be coupled to luer fitting 307 of introducer 7. Distal end 193 of sheath 191 may then be inserted transcervically, i.e., through the vagina and the cervix, into the uterus of the patient. Prior to introducing distal end 193 of sheath 191 into the patient, the cervix may be gradually dilated in the conventional manner using obturators of increasing diameter. The uterus may then be washed of blood and other debris that may be present by dispensing fluid from fluid supply 9 into introducer 7, which fluid may then exit introducer 7 distally through lumens 198-1 and 198-2. Valve 228 may be opened during this washing procedure so that fluid and any debris present in the uterus may exit the uterus proximally through lumen 196 of sheath 191 and, thereafter, may exit introducer 7 by passing proximally through tube 241, into main member 213 of sleeve 211, through side member 215 of sleeve 211, and through valve 228. When the washing procedure is complete, valve 228 may be closed while fluid may continue to be dispensed into the uterus through lumens 198-1 and 198-2, thereby causing the uterus to become distended by the fluid. When the uterus becomes sufficiently distended by such fluid, valve 228 may be opened while fluid may continue to be dispensed into the uterus. In this manner, the uterus may be maintained at a desired degree of distension while fluid is continuously circulated through the uterus. With the uterus thus distended with fluid, hysteroscope 8 may be used to examine the interior of the uterus.

If abnormalities are detected that one wishes to remove, tissue removal device 6 may be loaded into introducer 7, i.e., by inserting the distal ends of outer tubular member 76 and inner tubular member 77 distally through the instrument channel guide of introducer 7 and then through channel 196 of sheath 191, with housing 13 remaining external to the patient. Device 6 may then be manipulated so that window 89 of outer tubular member 76 may be positioned in proximity to the fibroid or other targeted tissue. Next, vacuum source 392 may be operated so as to cause suction to be applied to inner tubular member 77, thereby drawing tissue into outer tubular member 76 through window 89. In addition, the motor of motor drive assembly 11 may be actuated, thereby causing inner tubular member 77 simultaneously to rotate and to oscillate back and forth translationally within outer tubular member 76, resulting in the tissue drawn through window 89 to be cut. The cut tissue may then be suctioned from the patient through inner tubular member 77 by means of the aforementioned suction and, thereafter, collected in container 391. Once the fibroids or other targeted tissues have thus been removed from the patient, vacuum source 392 and the motor may be turned off, device 6 may be withdrawn from introducer 7, and introducer 7 may be withdrawn from the patient. Device 6 may be designed to be a single use device. If so, device 6 may then be disconnected from evacuation tube 393 and flexible motor shaft 398-2 and disposed of properly.

It should be noted that, although the above-discussion contemplates using introducer 7 to introduce device 6 into the uterus, one may insert device 6 transcervically into the uterus without the use of introducer 7. In such a situation, fluid may be administered transcervically to the uterus by a fluid dispensing device in order to distend the uterus, and, thereafter, observation of the uterus may be accomplished, for example, by ultrasonic imaging using an ultrasonic probe inserted transcervically into the uterus. Such an ultrasonic probe may be separate from device 6 or may be integrated into device 6. Alternatively, imaging of the uterus may be performed by MRI imaging.

Although one may vary one or more of the speed of rotational movement of inner tubular member 77, the frequency of oscillating translational movement of inner tubular member 77, the advance ratio of inner tubular member 77 (i.e., the ratio of the speed at which tubular member 77 oscillates translationally to the speed at which tubular member 77 rotates), and the magnitude of suction provided by vacuum source 392, particularly good results have been achieved under the following conditions: speed of rotation of tubular member 77—at least 1100 rpm, more preferably at least 5000 rpm, even more preferably approximately 6000 rpm; frequency of oscillating translational movement of tubular member 77—at least 1.5 cycles/second, more preferably about 2.5 to 4 cycles/second, even more preferably about 2.8 cycles/second; advance ratio of preferably less than 0.25, more preferably less than 0.15; and vacuum pressures in the range of 200 to 650 mmHg. Preferably, the above parameters are selected to achieve a rate of tissue removal of at least 1.5 gm/min while outer tubular member 76 has an outer diameter of no greater than about 3.0 mm.

As can be appreciated, as suction is applied to inner tubular member 77, some of the distension fluid located in the uterus may incidentally be withdrawn from the uterus through inner tubular member 77. This loss of distension fluid from the uterus may be undesirable if it interferes with maintenance of the uterus in an adequately distended state. Preferably, system 5 is constructed and operated so that, with a vacuum in excess of 300 mmHg, a volume of no more than about 300 cc/min of fluid is removed. This may involve, for example, applying suction only at specific times, for example, only when the motor for moving inner tubular member 77 is actuated or by closing resection window 89 with inner tubular member 77 each time the motor control is stopped.

In general, morcellators may be built in accordance with the present invention to have a lower outside diameter or crossing profile than current commercial products such as the Smith & Nephew Hysteroscopic Morcellator, but at the same time accomplish a higher tissue resection rate. In addition, morcellators in accordance with the present invention may be operated at a significantly higher vacuum while managing total fluid flow within acceptable limits.

For example, the cross sectional area of the aspiration lumen in morcellators in accordance with the present invention will typically be no more than about 12.0 square millimeters, and often no more than about 10.0 square millimeters. In certain embodiments, a cross sectional area of the aspiration lumen will be no more than about 8.0 millimeters squared, and, for certain applications, the area will be no more than about 7.5 square millimeters.

The tissue resection rate is generally at least about 1.5 gm/min, and often at least about 1.8 gm/min. In certain embodiments, the tissue resection rate is at least about 2.0 gm/min, and, in one embodiment, 2.2 or more gm/min.

Morcellators in accordance with the present invention may be constructed to have a fluid usage of no more than about 350 ml/min. In certain embodiments, fluid usage of no more than about 300 ml/min or no more than about 275 ml/min may be constructed.

Applied vacuum to the morcellators of the present invention will generally be in the range of from about 200 to about 650 mm Hg. The morcellator will typically be run at a vacuum of at least about 350 mm Hg, and, often at least about 500 mm Hg.

In one embodiment of the present invention, the cross sectional area of the aspiration lumen was about 7.1 mm$^2$, and yielded a tissue resection rate of about 1.4 gm/min, under vacuum of approximately 600 mm Hg.

In general, procedures accomplished in accordance with the present invention will require no more than about 10 minutes, and preferably, no more than about 8 or 9 minutes of active morcellation. During that time, total fluid (e.g. saline) introduced into the uterus will generally be no greater than about 12 liters, and, preferably no greater than about 10 liters or 8 liters. Distension fluid will preferably be maintained at a low enough pressure and short enough time to keep the total saline intravasation below 2.5 liters.

In a typical procedure in accordance with the present invention, utilizing a morcellator having an outside diameter of 3 mm, the fluid flow rate for aspiration of saline through the morcellator is approximately 260 ml/min (e.g. within the range of from about 240 to about 280 ml/min). Thus, in a ten minute procedure, approximately 2.6 liters of saline is aspirated through the morcellator. In that same procedure, the tissue resection rate is typically in excess of about 2 gm/min.

In a comparative experiment, a device manufactured in accordance with the present invention was compared to the performance of a reciprocating hysteroscopic morcellator from Smith and Nephew. Over a series of experiments with the predicate device, the vacuum was maintained on average in the 200 to 270 mm Hg range, morcellator speed was approximately 1100 rpm, tissue resection rate was approximately 1.4 gm/min, the fluid flow rate through the morcellator was approximately 247 ml/min, and the outside diameter of the morcellator was 4.0 mm.

The device constructed in accordance with the present invention was operated at a vacuum of 600 mm Hg, a speed of about 6000 rpm, to produce a resection rate of approximately 2.2 gm/min and an aspiration flow rate of about 266 ml/min through the morcellator. The outside diameter of the device was 3 mm.

The morcellator in accordance with the present invention thus produced a significantly higher resection rate, through a smaller outside diameter morcellator, at a roughly comparable flow rate of aspirated saline. In order to increase the resection rate of the predicate device, the vacuum must be significantly increased. For example, when the vacuum pressure in the predicate system was increased to about 670 mm Hg, the tissue cutting improved to 3.5 gm/min but fluid flow rate jumped to 540 ml/min.

One challenge with increased fluid flow rate which is responsive to increased vacuum is that the replacement fluid must be infused into the procedure site at an equal rate. In order to infuse fluid at a sufficient rate to allow the predicate device to function at a higher vacuum, the diameter of the already larger predicate morcellator must be increased. Applicants have determined that the use of the morcellator disclosed herein, with an outside diameter of no more than about 3 mm, in combination with the optic system, allows the dilatation of the cervix be limited to no more than about 5.5 mm. Increasing the diameter of the morcellator to accommodate the higher infusion rate as well as the already larger outside diameter of the predicate system is believed to cross the pain threshold and appears to impose the need or desirability for conducting the procedure under a general anesthetic. Applicants believe it to be a significant benefit for many patients to be able to avoid general anesthesia.

Figure 10A:
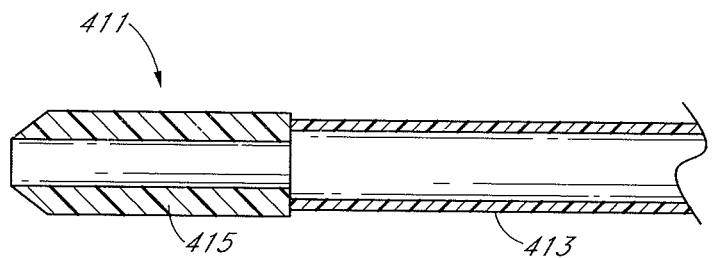
FIGS. 10(a) and 10(b) are fragmentary longitudinal section views of alternate inner tubular members that may be used in the tissue removal device shown in FIG. 1.
Figure 10B:
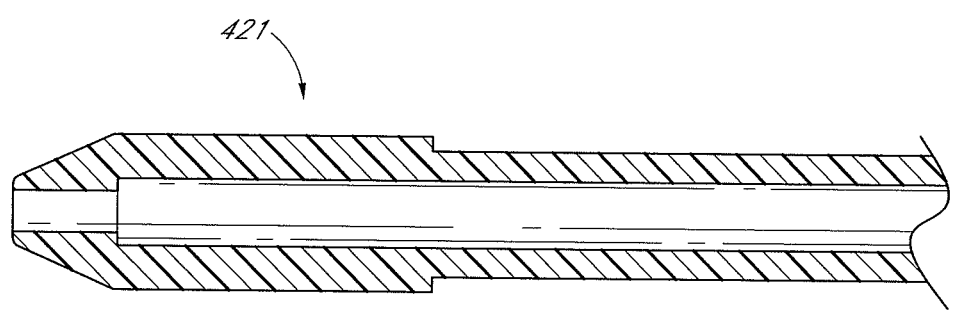

Referring now to FIGS. 10(a) and 10(b), there are shown fragmentary longitudinal section views of certain alternate inner tubular members that may be used in tissue removal device 6. A first such alternate inner tubular member is shown in FIG. 10(a) and is represented generally by reference numeral 411. Inner tubular member 411 may be similar in certain respects to inner tubular member 77; however, one notable difference between the two tubular members is that, whereas inner tubular member 77 may be a unitary structure made from a single piece of material, inner tubular member 411 may be formed by joining together two separate pieces of material. More specifically, inner tubular member 411 may comprise a first piece in the form of a proximal stem 413 and a second piece in the form of a distal tip 415, with distal tip 415 preferably having a length greater than the length of resection window 89 and more preferably having a length of less than about 2 inches and in one construction, about 1 inch. Proximal stem 413 and distal tip 415 may be made of the same material or may be made of different materials. Comparatively hard stainless steel materials, such as 400-series stainless steels (e.g., 440C stainless steel) where hardness exceeds Rockwell C values of about 50, are preferred for distal tip 415 as these materials enable a much sharper edge to distal tip 415 to be created. On the other hand, less hard stainless steel materials, such as 300-series stainless steels (e.g., 304 stainless steel), may be preferred for proximal stem 413 as these materials may be comparatively inexpensively formed into long tubular structures, for example, by extrusion whereas harder stainless steel materials must be machined to form tubular structures. The Rockwell C hardness of these proximal tube materials is less than about 40. Proximal stem 413 and distal tip 415 may be joined together by welding or other suitable techniques. Any of a variety of cutter edge and window configurations may be used, depending upon the desired performance, including any of those disclosed in U.S. patent application Ser. No.

12/098,250, filed Apr. 4, 2008 to Gruber, et al., the disclosure of which is hereby incorporated by reference in its entirety herein.

Another notable difference between tubular member 411 and tubular member 77 is that, whereas tubular member 77 may have a uniform inner diameter over its length, the inner diameter of distal tip 415 may be reduced as compared to the inner diameter of proximal stem 413 (e.g., 0.082 inch vs. 0.085 inch). Applicants believe that this increase in inner diameter from distal tip 415 to proximal stem 413 may result in a reduction in the incidence of clogging in tubular member 411 as the cut specimen, which has an outer diameter similar to distal tip 415, moves from distal tip 415 into proximal stem 413, which has a greater diameter than the cut specimen. This clearance within proximal stem 413 facilitates the proximal movement of the specimen through tubular member 411.

A second alternate inner tubular member is shown in FIG. 10(*b*) and is represented generally by reference numeral 421. Tubular member 421 may be similar in certain respects to tubular member 411, the principal difference between the two tubular members being that tubular member 421 may be a unitary structure made from a single piece of material, which may be, for example, a 17-7-series stainless steel. To form tubular member 421 from a tubular structure having a uniform inner diameter, one may first swage or roll the distal end of the tubular structure to reduce the inner diameter of the distal end and then may increase the inner diameter of the remainder of the structure by mechanically honing, expanding, or chemically etching.

Figure 11:
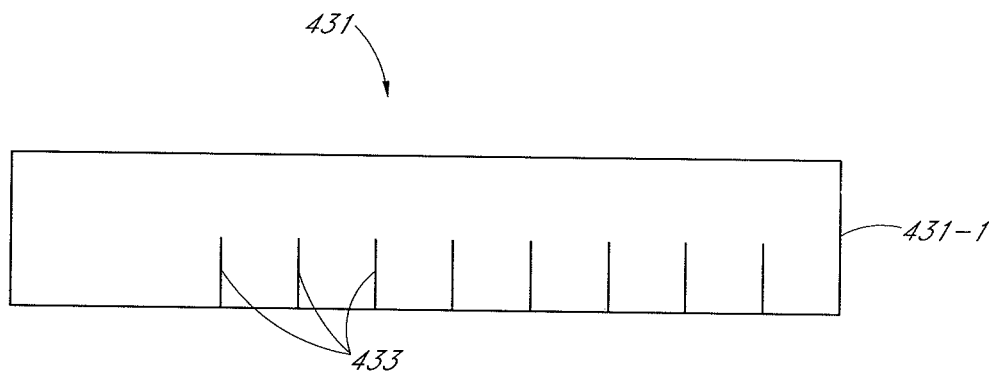
FIG. 11 is a side view of an alternate indicator sleeve that may be used in the tissue removal device shown in FIG. 1.

Referring now to FIG. 11, there is shown a side view of an alternate indicator sleeve 431 that may be used in tissue removal device 6. Indicator sleeve 431 may be similar in most respects to indicator sleeve 98, the principal difference between the two indicator sleeves being that sleeve 431 may be provided with labeled or unlabeled gradations 433 along its length to indicate the distance between each gradation and a distal end 431-1 of sleeve 431. Because sleeve 431 is preferably dimensioned and positioned so that distal end 431-1 of sleeve 431 indicates when distal end 92 of device 6 is aligned with the distal end of introducer 7, gradations 433 indicate the relative distance between distal end 92 of device 6 and the distal end of introducer 7. Gradations 433 may comprise, for example, numerical markings, symbols, hash marks, rings, or the like.

Figure 12:
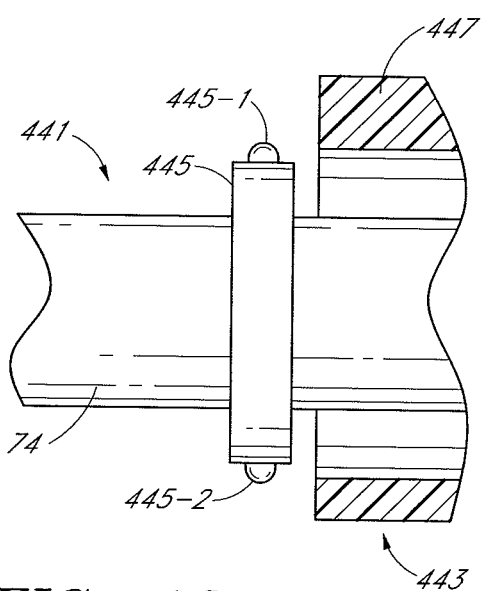
FIG. 12 is a fragmentary side view, partly in section, of an alternate combination of a tissue removal device and an introducer that may be used in the tissue removal system shown in FIG. 1.

Referring now to FIG. 12, there is shown a fragmentary side view, partly in section, of an alternate combination of a tissue removal device and an introducer that may be used in tissue removal system 5, the subject tissue removal device being represented generally by reference numeral 441 and the subject introducer being represented generally by reference numeral 443.

Device 441 and introducer 443 may be similar in most respects to device 6 and introducer 7, respectively, the principal differences being that device 441 may include, instead of sleeve 98, a position indicator ring 445 fixedly mounted on strain relief member 74, and introducer 443 may include, instead of proximal portion 203 of body 201, a proximal portion 447 appropriately shaped to provide just enough interference with bumps 445-1 and 445-2 on ring 445 so that a user may be given a tactile indication that ring 445 is being inserted into proximal portion 447.

Figure 13A:
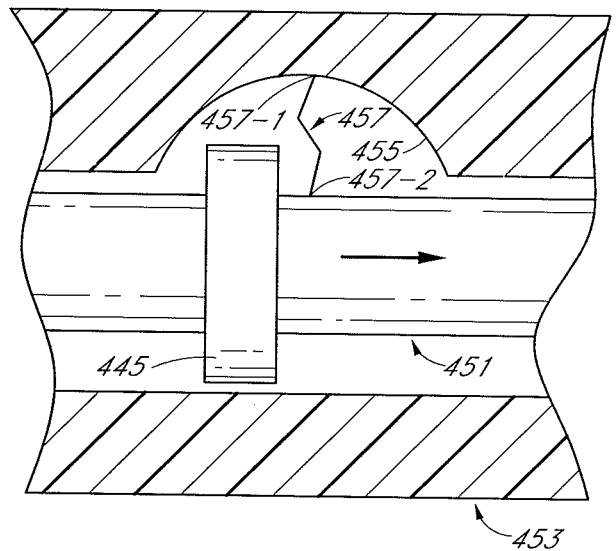
FIGS. 13(a) and 13(b) are fragmentary side views, partly in section, of a further alternate combination of a tissue removal device and an introducer that may be used in the tissue removal system shown in FIG. 1.
Figure 13B:
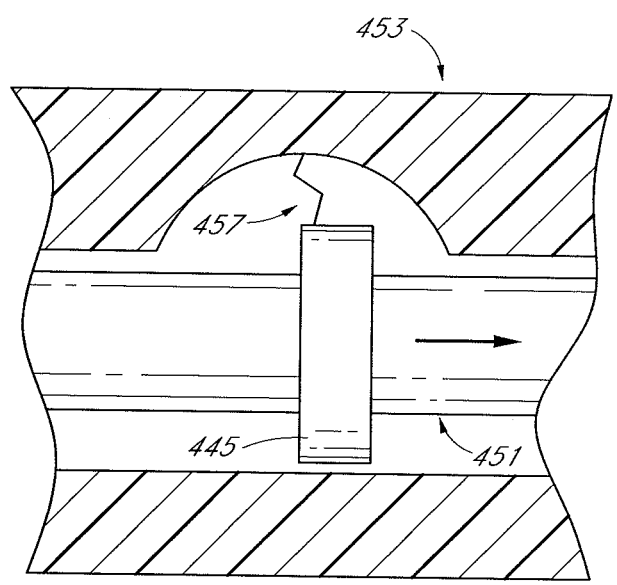

Referring now to FIGS. 13(*a*) and 13(*b*), there are shown fragmentary side views, partly in section, of another alternate combination of a tissue removal device and an introducer that may be used in tissue removal system 5, the subject tissue removal device being represented generally by reference numeral 451 and the subject introducer being represented generally by reference numeral 453.

Device 451 may be identical to device 441. Introducer 453 may be similar in most respects to introducer 7, the principal difference between the two introducers being that introducer 453 may be shaped to include a sound chamber 455 and may additionally include a spring clip or band 457. Clip 457 may have a fixed end 457-1 that is mounted within sound chamber 455 and a free end 457-2 that is constructed so as to be deflected by ring 445 when ring 445 is moved distally past clip 457. The deflection of clip 457 by ring 445 causes clip 457 to oscillate and to generate an audible signal.

Figure 14:
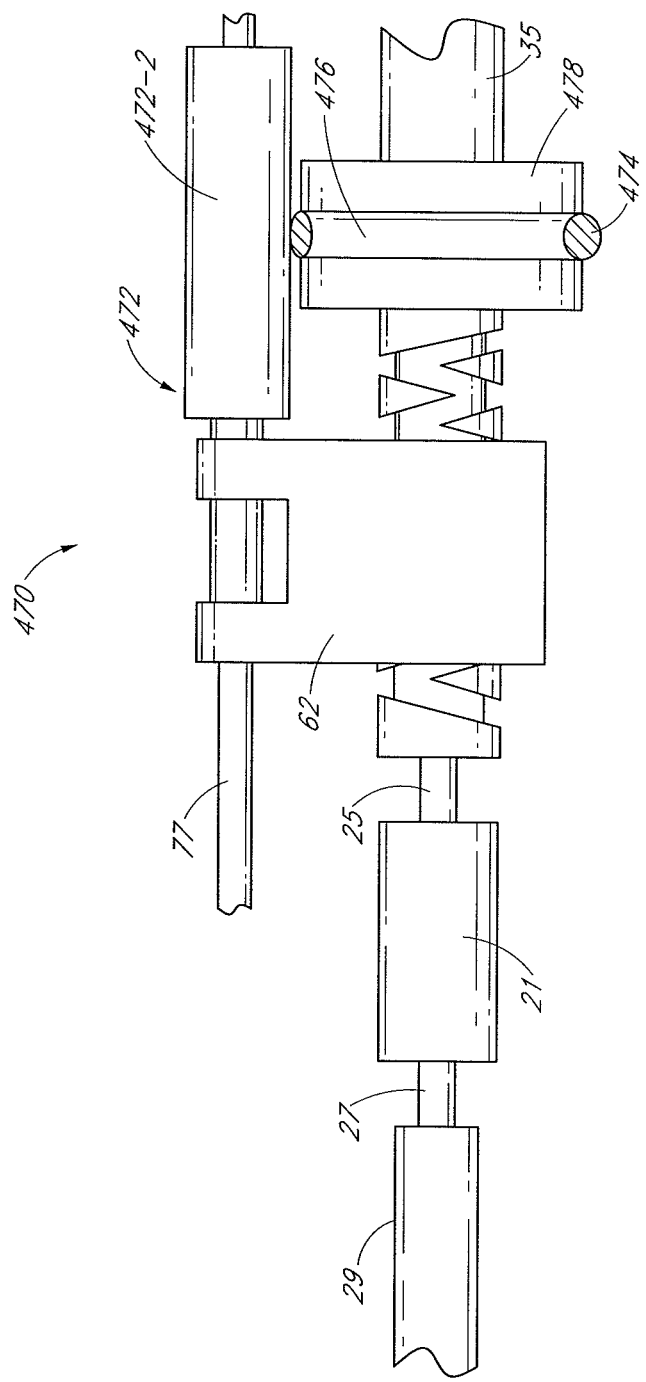
FIG. 14 is a fragmentary side view, partly in section, of an alternate tissue removal device that may be used in the tissue removal system of FIG. 1.

Referring now to FIG. 14, there is shown a fragmentary side view, partly in section, of an alternate tissue removal device that may be used in tissue removal system 5, said tissue removal device being represented generally by reference numeral 470. Certain aspects of device 470 not important to an understanding of the invention are neither shown nor described herein.

Device 470 may be similar in most respects to device 6, the principal differences between the two devices being that, whereas device 6 may comprise a rotational mechanism comprising a spur gear 51 engaged with a gear-shaped distal portion 72-2 of a shaft 72, device 470 instead may comprise a rotational mechanism comprising a shaft 472 comprising a tubular elastomeric distal portion 472-2 engaged for rotation with an elastomeric O-ring 474 fixedly mounted within a groove 476 of a cylindrical member 478 fixedly coupled to translation drive shaft 35.

Referring now to FIGS. 15(*a*) and 15(*b*), there are shown fragmentary perspective and exploded perspective views, respectively, of another alternate tissue removal device that may be used in tissue removal system 5, said tissue removal device being represented generally by reference numeral 500. Certain aspects of device 500 not important to an understanding of the invention are neither shown nor described herein.

Device 500 may be similar in many respects to device 6, one difference between the respective tissue removal devices being that device 500 may comprise a mounting bracket 501. Bracket 501, which may be a unitary structure made of a rigid metal or polymer, may be shaped to include a base portion 503, a proximal block 505 extending upwardly from the proximal end of base portion 503, a distal block 507 extending upwardly from the distal end of base portion 503, and an intermediate block 509 extending upwardly from an intermediate portion of base portion 503.

Another difference between device 500 and device 6 is that, whereas device 6 may comprise an internal drive shaft 21, a translation drive shaft 35, and a gear assembly 50, device 500 may instead comprise an internal drive shaft 510, a translation drive shaft 511, and a gear assembly 512. Internal drive shaft 510, which may be an elongated unitary structure made of a suitably rigid metal or polymer, may be shaped to include a proximal end 513 and a distal end 515. Proximal end 513 of shaft 510 may be coaxially mounted over and fixed to the distal end of external drive shaft 29. In this manner, the rotation of shaft 510 may be mechanically coupled to the rotation of shaft 29. An intermediate portion of shaft 510 may be received within a longitudinal bore 520 provided in block 505 of bracket 501. Gear assembly 512 may be fixedly mounted on distal end 515 of shaft 510 so as to rotate with shaft 510. Gear assembly 512 may include a larger diameter proximal spur gear 523 and a smaller diameter distal spur gear 525. Translation drive shaft 511, which may be an elongated unitary structure made of a suitably rigid metal or polymer, may be shaped to include a proximal end 537, an intermediate portion 539, and a distal end 541. Proximal end 537 of shaft 511 may be in the shape of a spur gear, which may be engaged with distal gear 525. In this manner, the rotation of shaft 511 may be mechanically coupled to the rotation of shaft 510, with the speed of rotation of shaft 511 being dependent on the speed of rotation of shaft 510 and the relative sizes of gear 525 and proximal end 537. Intermediate portion 539 may extend through a longitudinal bore 509-1 provided in block 509 of bracket 501. Intermediate portion 539 may be shaped to include a double helical portion 540 similar to the double helical portion of shaft 35. Distal end 541 of shaft 511 may be appropriately dimensioned to be received within an opening 544 provided in block 507 of bracket 501. It should be noted that, although shaft 511 is adapted for rotation, shaft 511 is translationally stationary.

Another difference between device 500 and device 6 is that, whereas device 6 may comprise a shaft 72 mechanically coupled to inner tubular member 77 so as to rotate and to oscillate translationally therewith, device 500 may instead comprise an elongated shaft 551 mechanically coupled to inner tubular member 77 so as to rotate and to oscillate translationally therewith. Shaft 551, which may be a unitary tubular structure made of a rigid metal or polymer, may be shaped to include a spur gear engaged with proximal gear 523. The gear may be elongated so that it may maintain engagement with proximal gear 523 even as the gear moves translationally relative to proximal gear 523. The speed at which shaft 551 rotates may be the same as or different than the speed at which gear 523 rotates, depending, for example, on the relative diameters of the two gears (the ratio of the rotational speeds of the two gears being inversely proportional to the ratio of the diameters of the two gears). Consequently, by appropriately dimensioning the gears, one can achieve a desired rotational speed, even where the rotational speed of the external drive shaft is fixed. For example, in the embodiment shown, the gear of shaft 551 may have a diameter that is one-third the diameter of gear 523 and, therefore, rotates three times as fast as gear 523. At the same time, proximal end 537 of shaft 511 may have a diameter that is four-thirds the diameter of gear 525 and, therefore, rotates three-quarters as fast as gear 525. Therefore, if the external drive shaft has a speed of rotation of about 2000 rpm, shaft 551 (and inner tubular member 77) would rotate at about 6000 rpm and shaft 511 would rotate at about 1500 rpm, which, with an appropriate shaping of the double helix portion of shaft 511, could be used to achieve an oscillating translational speed for inner tubular member 77 of about 2.8 cycles/second.

Figure 16:
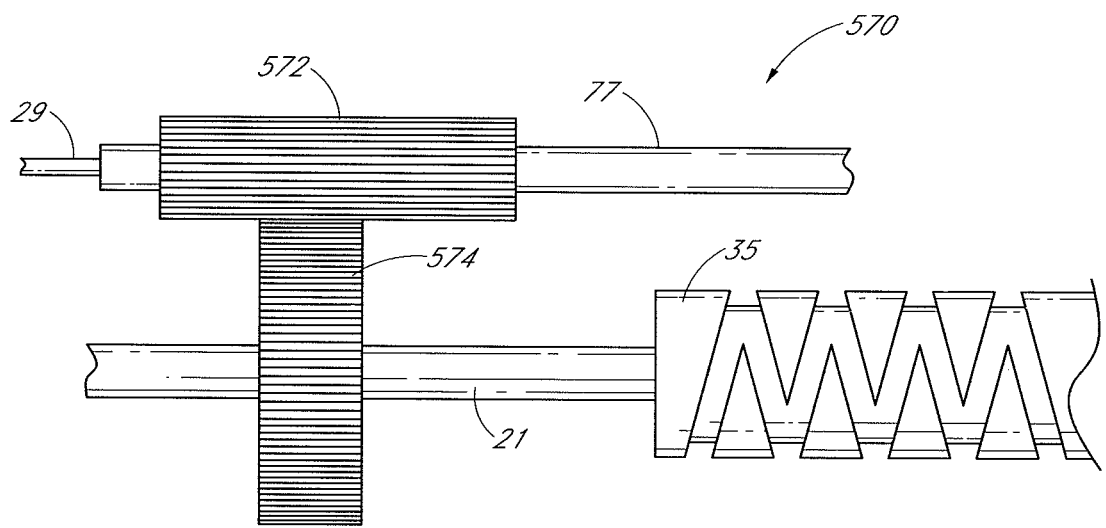
FIG. 16 is a fragmentary side view of another alternate tissue removal device that may be used in the tissue removal system of FIG. 1.

Referring now to FIG. 16, there is shown a fragmentary side view of an alternate tissue removal device that may be used in tissue removal system 5, said tissue removal device being represented generally by reference numeral 570. Certain aspects of device 570 not important to an understanding of the invention are neither shown nor described herein.

Device 570 may be similar in many respects to device 6. One difference between the two devices may be that, whereas device 6 may fix inner drive shaft 21 to external drive shaft 29 for rotation therewith and may couple the rotation of inner tubular member 77 to inner drive shaft 21 through the engagement of shaft 72 and gear 51, device 570 may instead fix inner tubular member 77 to external drive shaft 29 for rotation therewith and may couple the rotation of inner drive shaft 21 to inner tubular member 77 through the engagement of a pair of spur gears 572 and 574. Gear 572 may be coaxially inserted over and fixed to inner tubular member 77, and gear 574 may be coaxially inserted over and fixed to inner drive shaft 21. Gears 572 and 574 may be sized to be, for example, in a 1:4 ratio, respectively, so that, if external drive shaft 29 rotates at about 6000 rpm, inner tubular member 77 also rotates at about 6000 rpm whereas inner drive shaft 21 rotates at about 1500 rpm.

Figure 17:
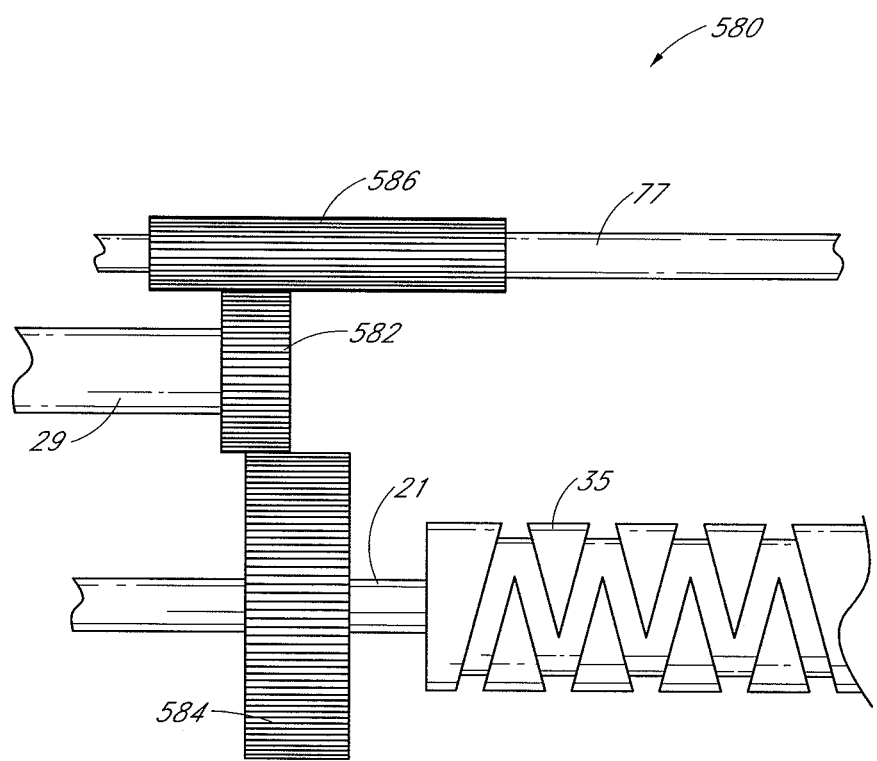
FIG. 17 is a fragmentary side view of another alternate tissue removal device that may be used in the tissue removal system of FIG. 1.

Referring now to FIG. 17, there is shown a fragmentary side view of an alternate tissue removal device that may be used in tissue removal system 5, said tissue removal device being represented generally by reference numeral 580. Certain aspects of device 580 not important to an understanding of the invention are neither shown nor described herein.

Device 580 may be similar in many respects to device 6. One difference between the two devices may be that, whereas device 6 may fix inner drive shaft 21 to external drive shaft 29 for rotation therewith and may couple the rotation of inner tubular member 77 to inner drive shaft 21 through the engagement of shaft 72 and gear 51, device 580 instead may couple the rotation of inner drive shaft 21 to external drive shaft 29 through the engagement of a pair of spur gears 582 and 584 and may couple the rotation of inner tubular member 77 to external drive shaft 29 through the engagement of a spur gear 586 with gear 582. Gear 582 may be coaxially inserted over and fixed to external drive shaft 29, gear 584 may be coaxially inserted over and fixed to inner drive shaft 21, and gear 586 may be coaxially inserted over and fixed to inner tubular member 77. Gears 582 and 584 may be sized to be, for example, in a 1:2 ratio, respectively, and gears 582 and 586 may be sized to be, for example, in a 2:1 ratio, respectively. In this manner, if external drive shaft 29 rotates at about 3000 rpm, inner tubular member 77 rotates at about 6000 rpm and inner drive shaft 21 rotates at about 1500 rpm.

Figure 18:
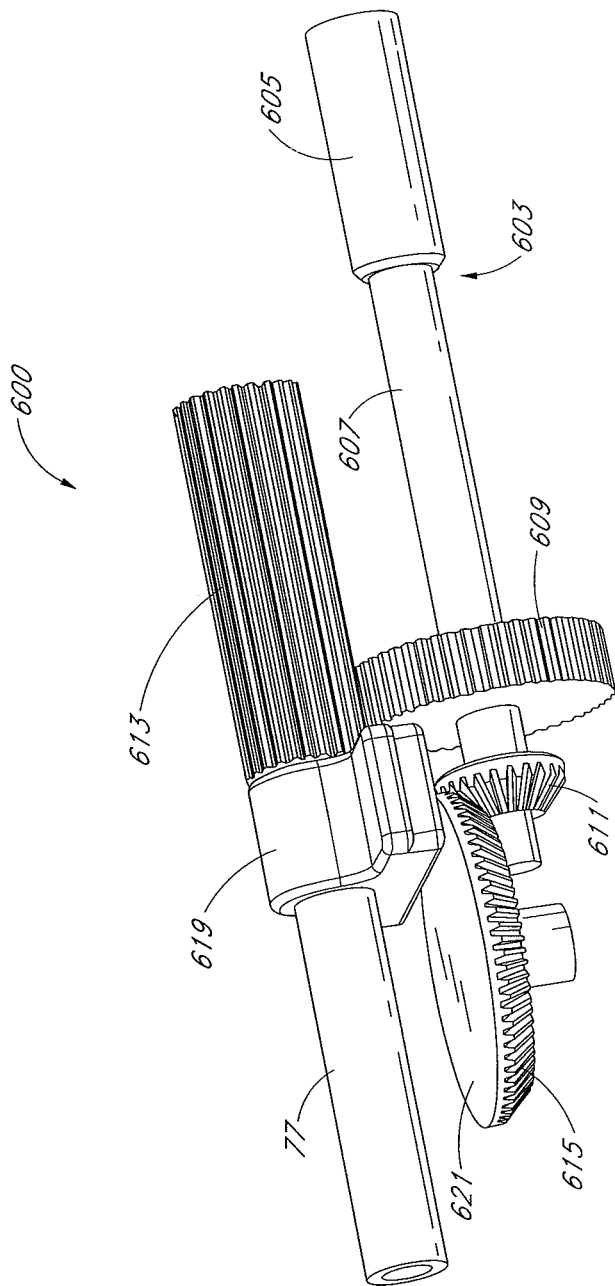
FIG. 18 is a fragmentary perspective view of another alternate tissue removal device that may be used in the tissue removal system of FIG. 1.

Referring now to FIG. 18, there is shown a fragmentary perspective view of an alternate tissue removal device that may be used in tissue removal system 5, said tissue removal device being represented generally by reference numeral 600. Certain aspects of device 600 not important to an understanding of the invention are neither shown nor described herein.

Device 600 may be similar in many respects to device 6. One difference between the two devices may be their respective mechanisms for rotating and translationally reciprocating inner tubular member 77. More specifically, device 600 may comprise an internal drive shaft 603 fixed to an external drive shaft (not shown) so as to rotate therewith. Internal drive shaft 603 may comprise a proximal portion 605 and a distal portion 607. A spur gear 609 and a bevel gear 611 may be coaxially mounted over distal portion 607 and fixed thereto for rotation therewith, with bevel gear 611 being positioned distally relative to spur gear 609. A spur gear 613 may be coaxially mounted over inner tubular member 77 and fixed thereto for rotation therewith, gear 613 being engaged with gear 609 so that the rotation of internal drive shaft 603 causes the rotation of inner tubular member 77. (The speed of rotation of inner tubular member 77, as compared to that of drive shaft 603, may be controlled by the relative diameters of gears 609 and 613). A bevel gear 615, positioned distally relative to internal drive shaft 603, may be engaged with bevel gear 611. A saddle 619 may be coaxially mounted over inner tubular member 77, saddle 619 being fixed to inner tubular member 77 for translational movement therewith but permitting tubular member 77 to freely rotate therewithin. Saddle 619 and bevel gear 615 may be coupled to one another by a pin (not shown) extending upwardly from the top surface 621 of gear 615 and a slot (not shown) provided on the bottom surface of saddle 619, the slot in saddle 619 receiving the pin on bevel gear 615. The slot in saddle 619 may be oriented perpendicularly to the longitudinal axis of inner tubular member 77 and may be appropriately dimensioned so that the pin on bevel gear 615 travels back and forth within the slot in saddle 619 as bevel gear 615 rotates. In this manner, the rotation of bevel gear 615 may cause the translational oscillation of inner tubular member 77.

Figure 19:
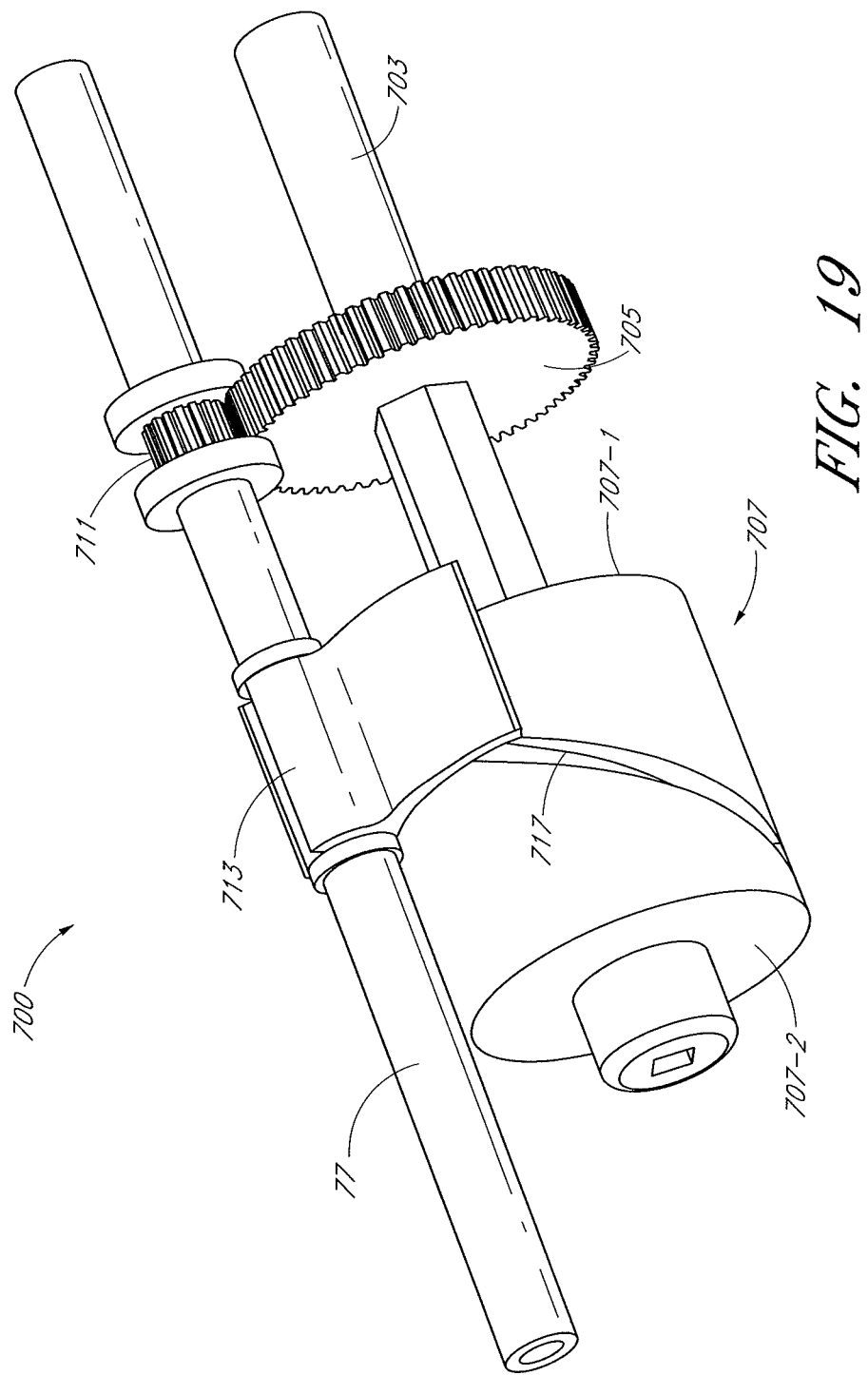
FIG. 19 is a fragmentary perspective view of another alternate tissue removal device that may be used in the tissue removal system of FIG. 1.

Referring now to FIG. 19, there is shown a fragmentary perspective view of an alternate tissue removal device that may be used in tissue removal system 5, said tissue removal device being represented generally by reference numeral 700. Certain aspects of device 700 not important to an understanding of the invention are neither shown nor described herein.

Device 700 may be similar in many respects to device 6. One difference between the two devices may be their respective mechanisms for rotating and translationally reciprocating inner tubular member 77. More specifically, device 700 may comprise an internal drive shaft 703 fixed to an external drive shaft (not shown) so as to rotate therewith. A spur gear 705 and a translation cam 707 may be coaxially mounted over drive shaft 703 and fixed thereto for rotation therewith, with translation cam 707 being positioned distally relative to spur gear 705. A spur gear 711 may be coaxially mounted over inner tubular member 77 and fixed thereto for rotation therewith, gear 711 being engaged with gear 705 so that the rotation of internal drive shaft 703 causes the rotation of inner tubular member 77. (The speed of rotation of inner tubular member 77, as compared to that of drive shaft 703, may be controlled by the relative diameters of gears 705 and 711). A saddle 713 may be coaxially mounted over inner tubular member 77, saddle 713 being fixed to inner tubular member 77 for translational movement therewith but permitting tubular member 77 to freely rotate therewithin. Saddle 713 and translation cam 707 may be coupled to one another by a pin (not shown) extending downwardly from saddle 713 and a looped groove 717 provided in cam 707, groove 717 receiving the pin on saddle 713. Groove 717 in cam 707 may be shaped to extend from about the proximal end 707-1 of cam 707 to about the distal end 707-2 of cam 707 and back to about the proximal end 707-1 of cam 707 over the course of one rotation of cam 707. In this manner, as cam 707 rotates and the pin travels back and forth within groove 717, inner tubular member 77 may be translationally oscillated correspondingly.

Figure 20:
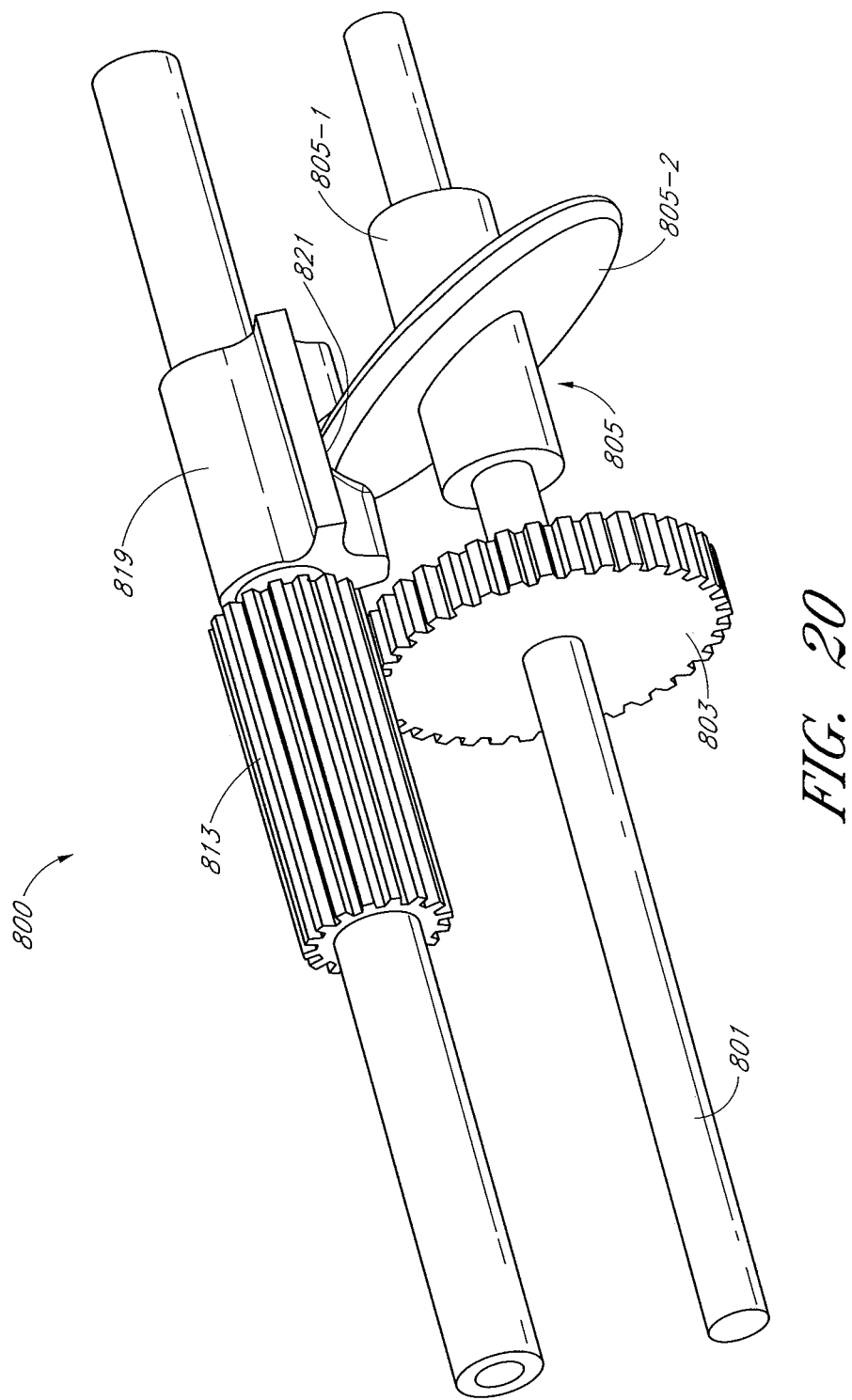
FIG. 20 is a fragmentary perspective view of another alternate tissue removal device that may be used in the tissue removal system of FIG. 1.

Referring now to FIG. 20, there is shown a fragmentary perspective view of an alternate tissue removal device that may be used in tissue removal system 5, said tissue removal device being represented generally by reference numeral 800. Certain aspects of device 800 not important to an understanding of the invention are neither shown nor described herein.

Device 800 may be similar in many respects to device 6. One difference between the two devices may be their respective mechanisms for rotating and translationally reciprocating inner tubular member 77. More specifically, device 800 may comprise an internal drive shaft 801 fixed to an external drive shaft (not shown) so as to rotate therewith. A spur gear 803 may be coaxially mounted over drive shaft 801 and fixed thereto for rotation therewith. In addition, a translation cam 805 may be coaxially mounted over drive shaft 801 and fixed thereto for rotation therewith. Translation cam 805 may comprise a tubular portion 805-1 and a disc portion 805-2, disc portion 805-2 being fixedly mounted on tubular portion 805-1 at a non-perpendicular angle relative to the longitudinal axis of tubular portion 805-2. A spur gear 813 may be coaxially mounted over inner tubular member 77 and fixed thereto for rotation therewith, gear 813 being engaged with gear 803 so that the rotation of internal drive shaft 801 causes the rotation of inner tubular member 77. (The speed of rotation of inner tubular member 77, as compared to that of drive shaft 801, may be controlled by the relative diameters of gears 803 and 813). A saddle 819 may be coaxially mounted over inner tubular member 77, saddle 819 being fixed to inner tubular member 77 for translational movement therewith but permitting tubular member 77 to freely rotate therewithin. Saddle 819 may be shaped to include a recess 821, which may receive the top of disc portion 805-2. In this manner, as drive shaft 801 rotates, causing disc portion 805-2 to "wobble" back and forth, saddle 819, and thus inner tubular member 77, may be translationally oscillated correspondingly.

Figure 21:
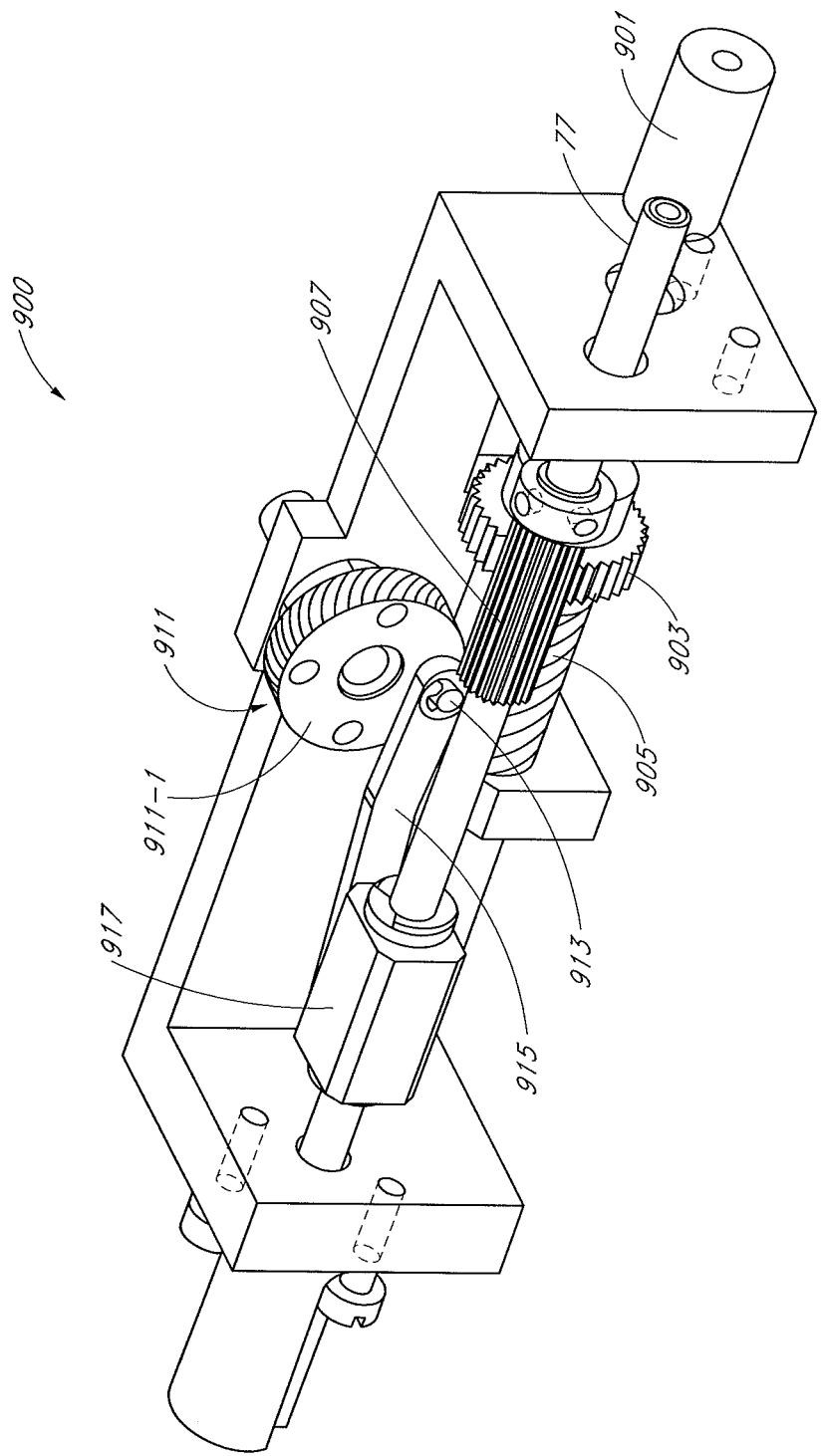
FIG. 21 is a fragmentary perspective view of another alternate tissue removal device that may be used in the tissue removal system of FIG. 1.
Figure 22E:
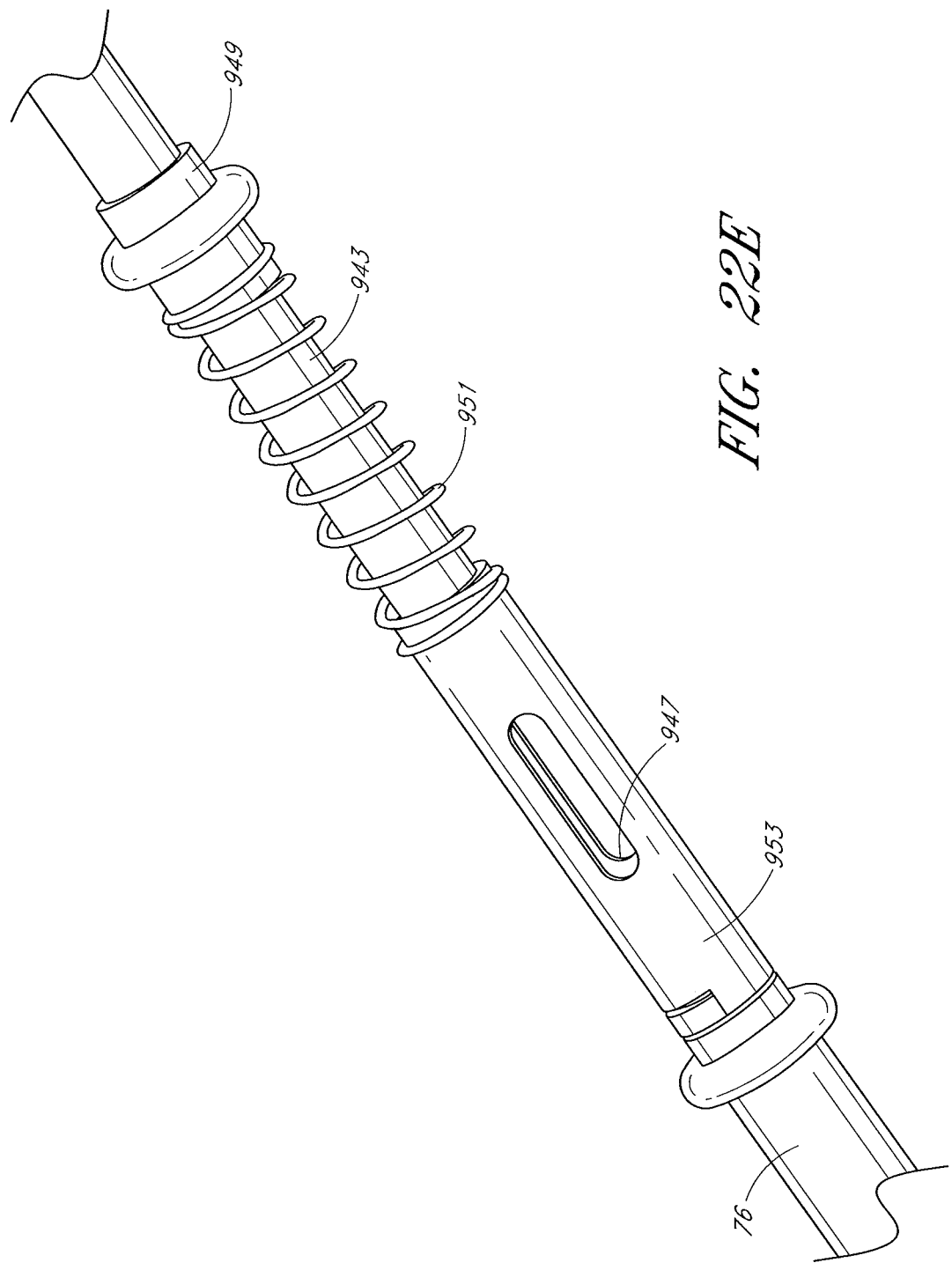

Referring now to FIG. 21, there is shown a fragmentary perspective view of an alternate tissue removal device that may be used in tissue removal system 5, said tissue removal device being represented generally by reference numeral 900. Certain aspects of device 900 not important to an understanding of the invention are neither shown nor described herein.

Device 900 may be similar in many respects to device 6. One difference between the two devices may be their respective mechanisms for rotating and translationally reciprocating inner tubular member 77. More specifically, device 900 may comprise an internal drive shaft 901 fixed to an external drive shaft (not shown) so as to rotate therewith. A spur gear 903 and a worm gear 905 may be coaxially mounted over drive shaft 901 and fixed thereto for rotation therewith. A spur gear 907 may be coaxially mounted over inner tubular member 77 and fixed thereto for rotation therewith, gear 907 being engaged with gear 903 so that the rotation of internal drive shaft 901 causes the rotation of inner tubular member 77. (The speed of rotation of inner tubular member 77, as compared to that of drive shaft 901, may be controlled by the relative diameters of gears 903 and 907). A worm gear 911 may be engaged with worm gear 905 so that worm gear 911 rotates as worm gear 905 rotates. A pin 913 may be mounted near the periphery of a front face 911-1 of worm gear 911. A reciprocation arm 915 may have a first end secured to pin 913 and a second end secured to a block 917 translationally coupled to inner tubular member 77. In this manner, as worm gear 911 rotates and the position of pin 913 on worm gear 911 changes, arm 915 moves block 917 and inner tubular member 77 back and forth translationally.

As can be appreciated, one would like to minimize the amount of distension fluid that flows from the uterus of the patient through the tissue removal device when the tissue removal device is left in the patient but the cutting motor for the tissue removal device has temporarily been turned off, e.g., during those periods when the operator of the tissue removal device stops cutting to examine the patient. Such a loss of distension fluid is undesirable for at least the reason that the lost distension fluid will need to be replenished in order to keep the uterus distended. In device 6, this problem may be addressed through electronics by sensing when the motor for device 6 is about to be turned off and, in those instances, by positioning inner tubular member 77 translationally relative to outer tubular member 76 so that resection window 89 is closed. An alternate approach to this problem is exemplified by tissue removal device 940, which is shown in FIGS. 22(a) through 22(e). Certain aspects of device 940 not important to an understanding of the invention are neither shown nor described herein.

Device 940 is similar in certain respects to device 6. However, one difference between the respective devices is that device 940 may comprise an inner tubular member 943 having a closed proximal end 945 and a side window 947. A spring mount 949 may be coaxially mounted over inner tubular member 943 and fixed thereto for rotation therewith. The proximal end of a spring 951 may be fixed to spring mount 949, and the distal end of spring 951 may be fixed to a valve member 953 coaxially mounted over inner tubular member 943, valve member 953 being capable of rotating relative to inner tubular member 943. Valve member 953 may include a side window 955. Side window 955 may be alignable with side window 943 depending on the respective rotational positions of inner tubular member 943 and valve member 953. A stop 957 may be formed on inner tubular member 943, stop 957 being detachably engageable with valve member 953 to couple the rotation of valve member 953 with inner tubular member 943. A vacuum housing 959 may be coaxially mounted over valve member 953, valve member 953 being freely rotatable within vacuum housing 959. Outer tubular member 76 may be fixedly mounted on vacuum housing 959. A pair of O-rings 961-1 and 961-2 may be provided to function as seals.

Prior to the cutting motor of device 940 being actuated, side window 955 of valve member 953 and side window 947 of inner tubular member 943 are 90 degrees out of register with one another. However, once the cutting motor of device 940 is actuated, inner tubular member 943 begins to rotate. This causes spring 951 to try to unwind, thereby causing valve member 953 to rotate so that side window 955 of valve member 953 is aligned with side window 947 of inner tubular member 943. With valve member 953 thus rotationally aligned with inner tubular member 943, stop 957 prevents further rotation of valve member 953 relative to inner tubular member 943. When the cutting motor of device 940 is then turned off, spring 951 causes valve member 953 to be rotated back to its original orientation relative to inner tubular member 943.

Figure 23:
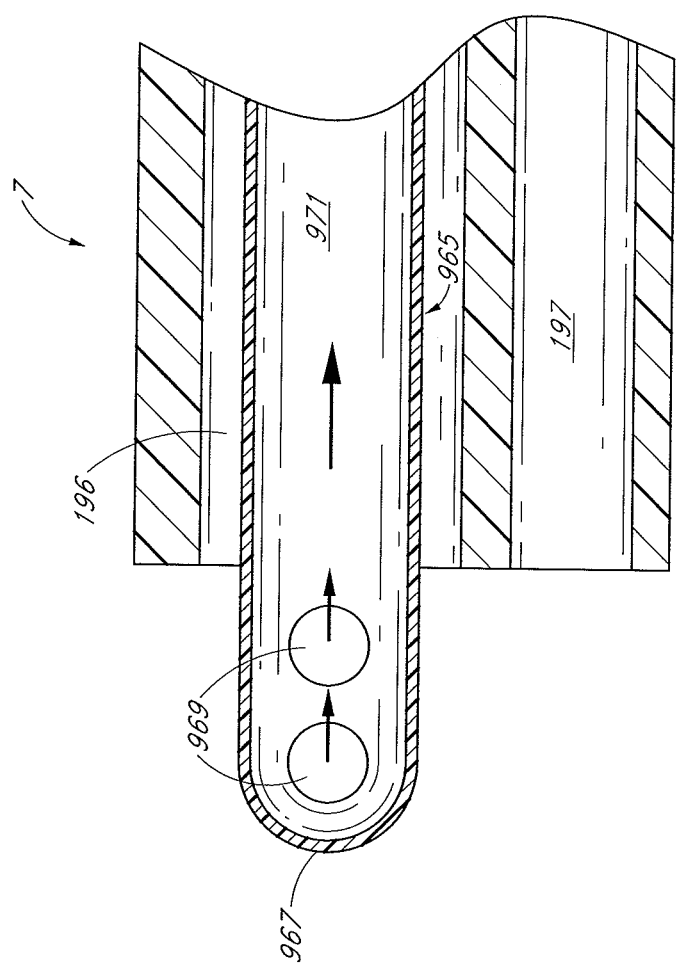
FIG. 23 is a fragmentary section view of an obturator of the present invention inserted into the introducer shown in FIG. 1.

As noted above, introducer 7 preferably comprises valve 233, which is designed to keep fluid from escaping from the patient when device 6 is not inserted into introducer 7. However, there may be situations in which it is desirable to simultaneously have fluid flowing into and out of the patient without having device 6 inserted into introducer 7. Therefore, referring now to FIG. 23, there is shown a fragmentary section view of an obturator 965 positioned within a channel of introducer 7. Obturator 965 may be shaped to include a blunt distal end 967 and a plurality of openings 969 leading to a longitudinally-extending channel 971. Obturator 965 may be positioned in instrument channel 196, as shown, or may be positioned in fluid input channel 198-1 or fluid input channel 198-2 to provide bidirectional fluid flow (for example, with fluid inflow exiting channels 198-1 or 198-2 in the space between channels 198-1 or 198-2 and obturator 965 and with fluid outflow entering obturator 965 through openings 969). The fluid outflow entering channel 971 through openings 969 may exit obturator 965 through the proximal end (not shown) of obturator 965.

Figure 24:
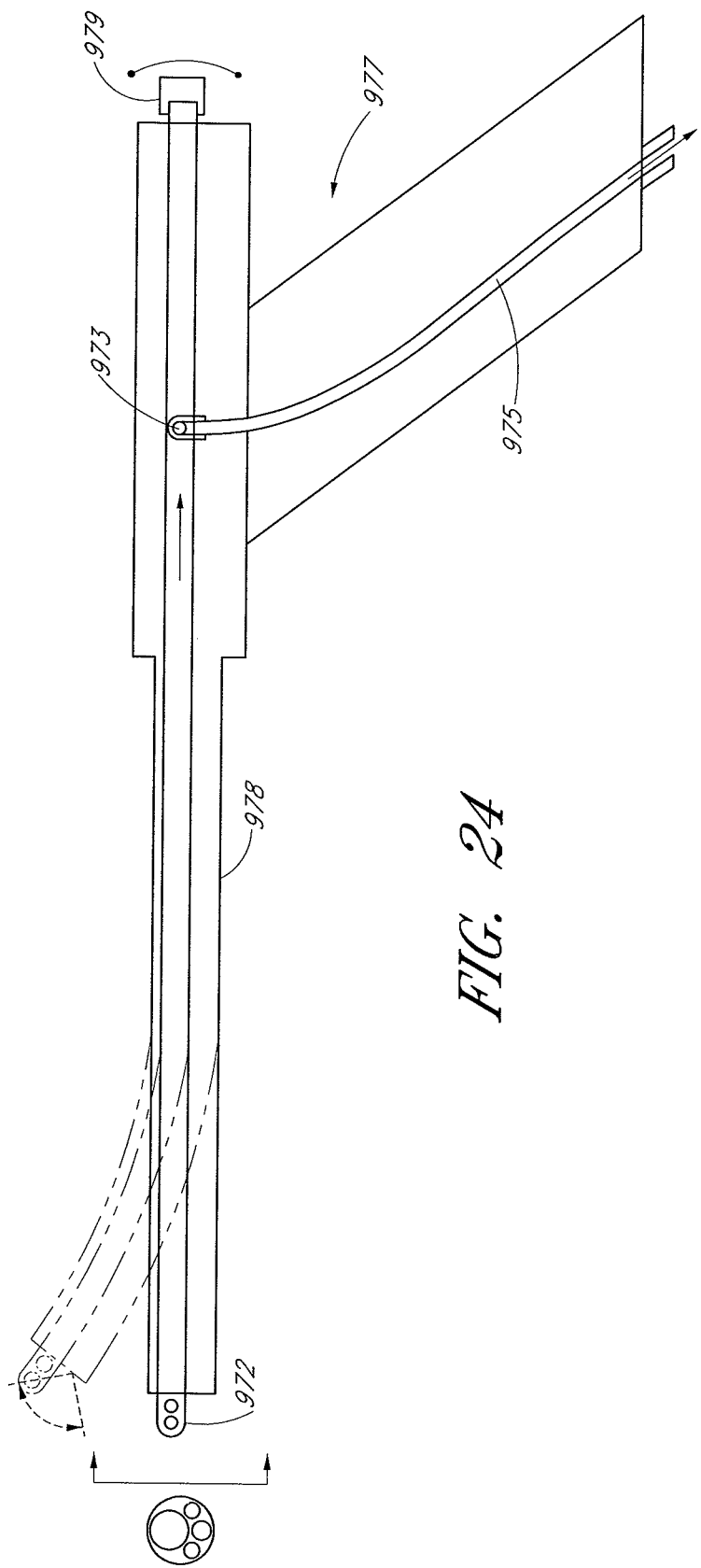
FIG. 24 is a side view of an alternate combination of an obturator and an introducer constructed according to the present invention.

An alternate obturator 972 is shown in FIG. 24, obturator 972 having a side opening 973 at an intermediate location along its length, side opening 973 being aligned with an outflow fluid channel 975 provided in an alternate introducer 977. If desired, obturator 972 may be made of a resilient member having a bend and introducer 977 may be provided with a sheath 978 made of a flexible material. In this manner, obturator 972 may be used to provide a bend to sheath 978, which, by rotating the proximal end 979 of obturator 972, may be used to steer the distal end of sheath 978.

Figure 25A:
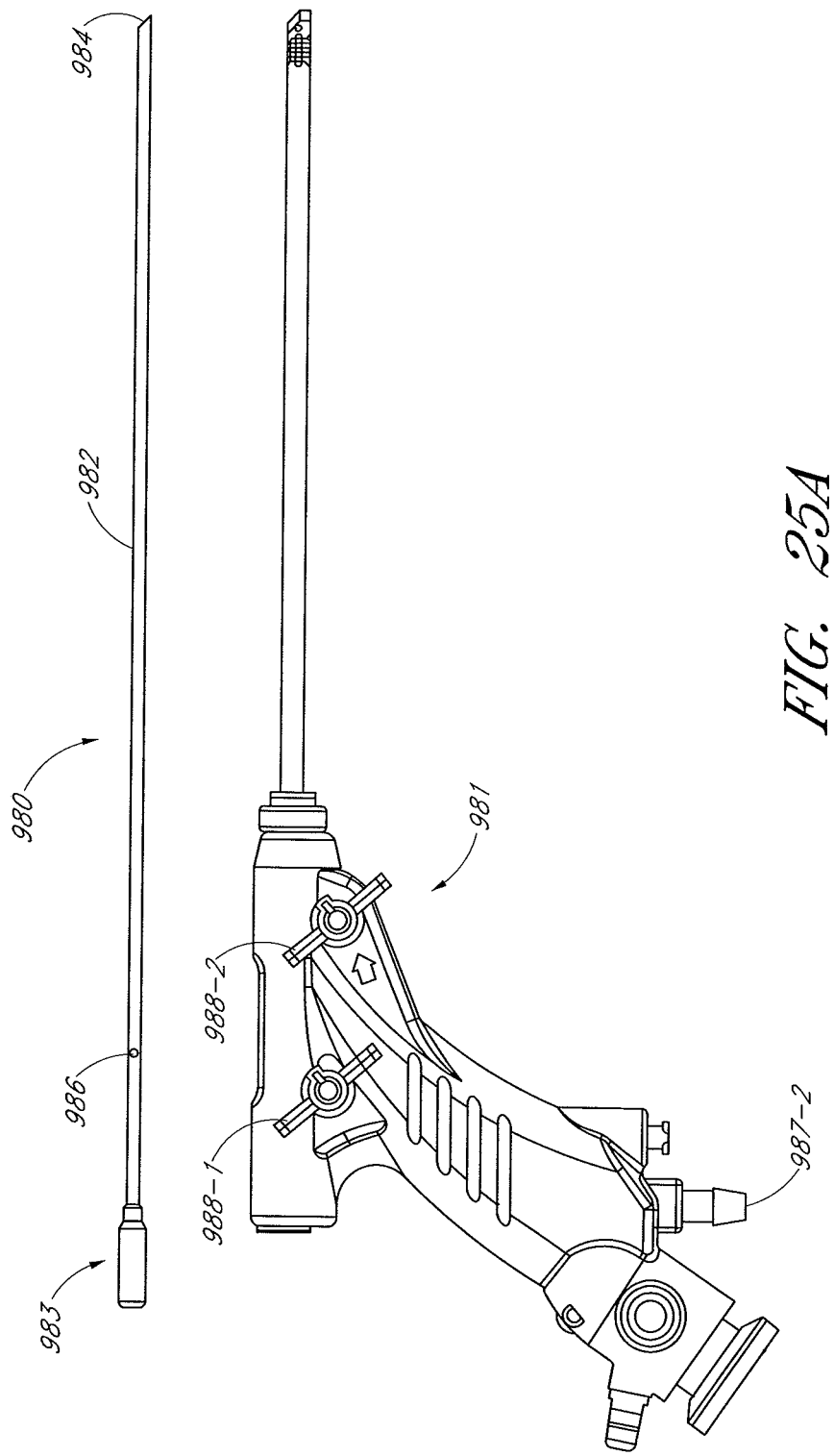
FIGS. 25(a) and 25(b) are unassembled side and assembled section views, respectively, of another combination of an obturator and an introducer constructed according to the present invention.
Figure 25B:
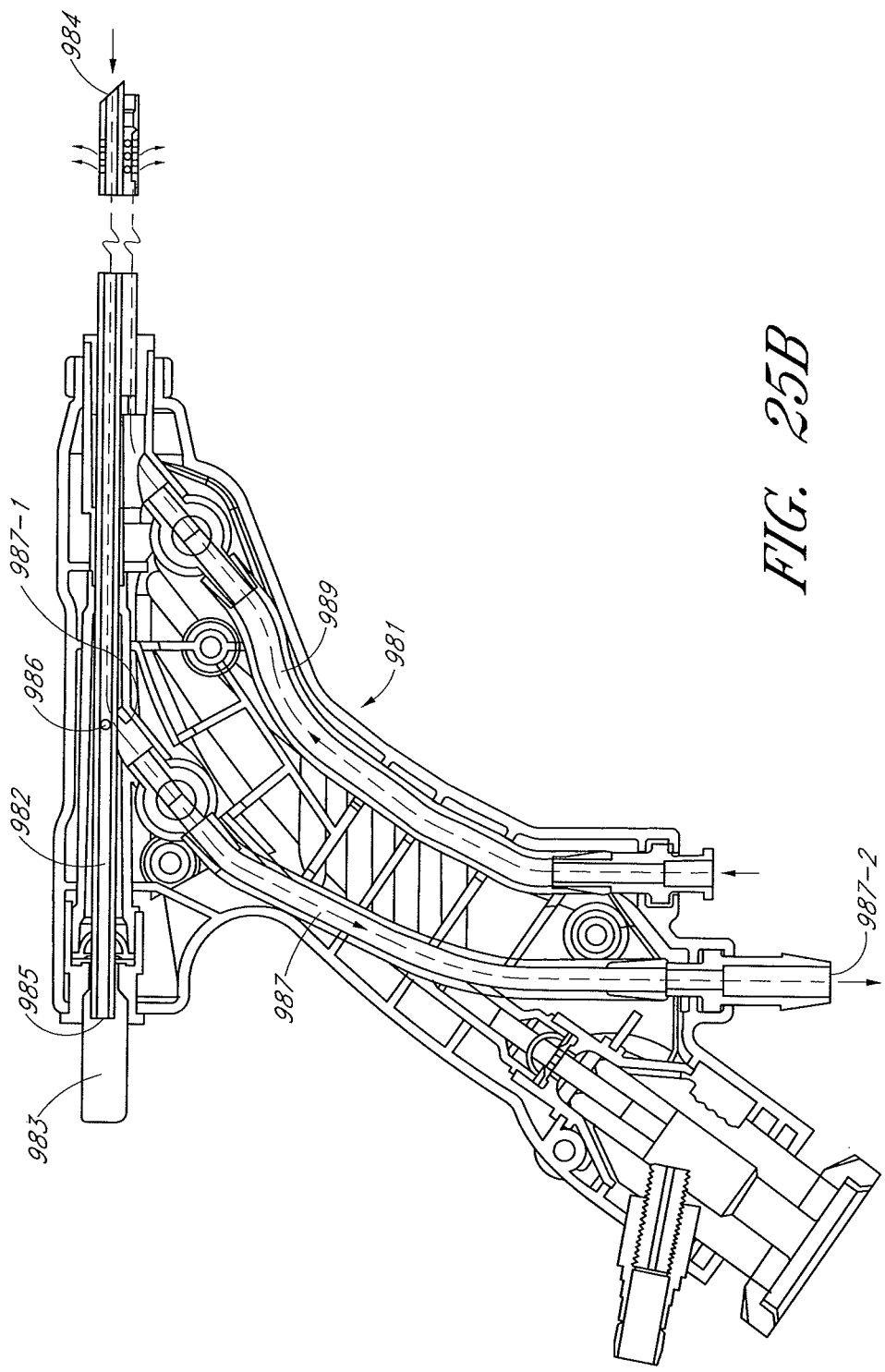

Referring now to FIGS. 25(*a*) and 25(*b*), there is shown an alternate combination of an obturator and an introducer according to the present invention, the obturator being represented generally by reference numeral 980 and the introducer being represented generally by reference numeral 981.

Obturator 980, which may be similar in many respects to obturator 965, may comprise a distal member 982 and a proximal member 983. Distal member 982 may be tubular and may comprise an open distal end 984, a closed proximal end 985, and a side opening 986, with proximal member 983 being mounted over proximal end 985 of distal member 982.

Introducer 981 may be similar in many respects to introducer 7, one difference between the respective introducers being that introducer 981 may additionally comprise a fluid outflow channel 987. Channel 987 may comprise a distal end 987-1 that may be aligned with side opening 986 of obturator 980 when obturator 980 is installed in introducer 981. In this manner, outflow fluid may flow from obturator 980 to channel 987 and may exit introducer 981 through a proximal end 987-2 of channel 987. Introducer 981 may additionally comprise a valve 988-1 and a valve 989-2. Valve 988-1, which may be a stopcock valve, may be used to control the flow of fluid through channel 987. Valve 988-2, which may be a stopcock valve, may be used to control the flow of fluid through inflow channel 989.

Figure 26A:
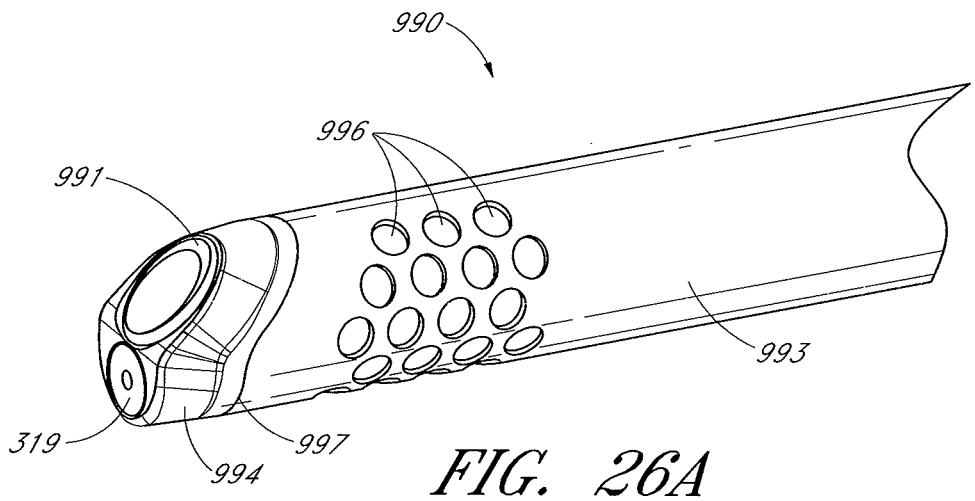
FIGS. 26(a) through 26(c) are fragmentary perspective views of another alternate introducer device to the introducer device shown in FIG. 1, with the alternate introducer device being shown in partially exploded states in FIGS. 26(b) and 26(c)
Figure 26B:
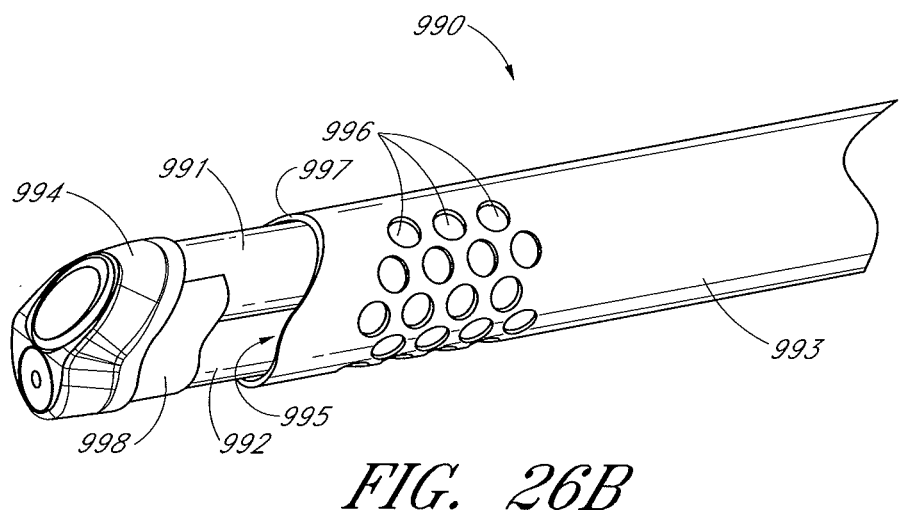
Figure 26C:
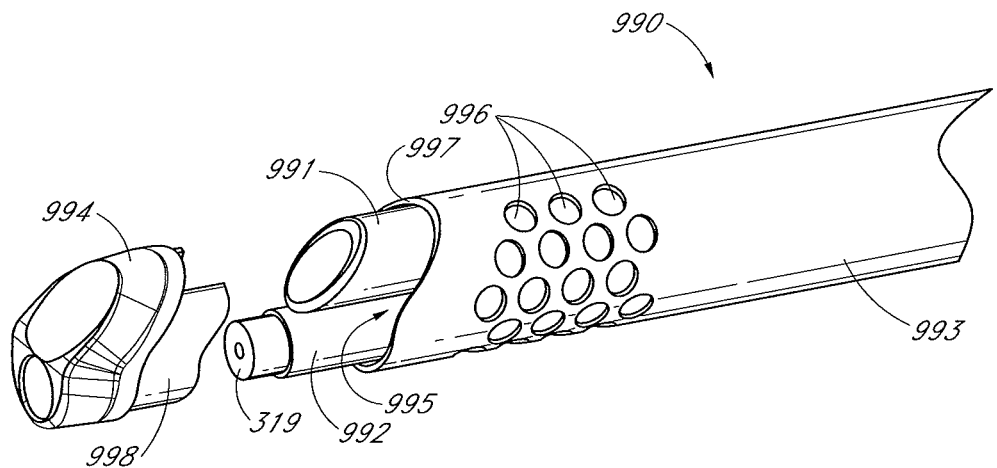

Referring now to FIGS. 26(*a*) through 26(*c*), there are shown various views of an alternate introducer device to introducer device 7, the alternate introducer device being represented generally by reference numeral 990.

Introducer device 990 may be similar in many respects to introducer device 7. One difference between introducer device 990 and introducer device 7 may be that, whereas introducer device 7 may comprise a sheath 191 having a top lumen 196, a bottom lumen 197 and a pair of side lumens 198-1 and 198-2, introducer device 990 may comprise a top tubular member 991, a bottom tubular member 992, a sleeve 993, and a distal cap 994. Top tubular member 991 may be used, for example, as an instrument channel to receive, for example, tissue removal device 6 or obturator 965. Bottom tubular member 992 may be used, as is shown, for example, to receive distal end 319 of hysteroscope 8. Sleeve 993, which may be made of stainless steel or the like, may be appropriately dimensioned to coaxially receive top tubular member 991 and bottom tubular member 992 and may be shaped to define a pair of fluid channels 995 on opposite sides of tubular members 991 and 992 in the spaces between the inner surface of sleeve 993 and the outer surfaces of tubular members 991 and 992. A plurality of transverse openings 996 may be provided in sleeve 993 near the distal end 997 thereof, openings 996 providing side access to fluid channels 995. In this manner, fluid inflow to the patient may be provided by having the fluid pass distally through channels 995 and then exit radially through openings 996. Fluid outflow from the patient may travel proximally through cap 994 and then proximally through top tubular member 991 (for example, by passing through an instrument positioned in top tubular member 991). It is believed that the fluid flow pattern provided by introducer device 990 may be particularly effective in removing blood and other undesired fluids from a patient. Cap 994 may include a retainer 998, which may receive the distal ends of tubular members 991 and 992 and which may be inserted into and fixed to the distal end 997 of sleeve 993.

Figure 27:
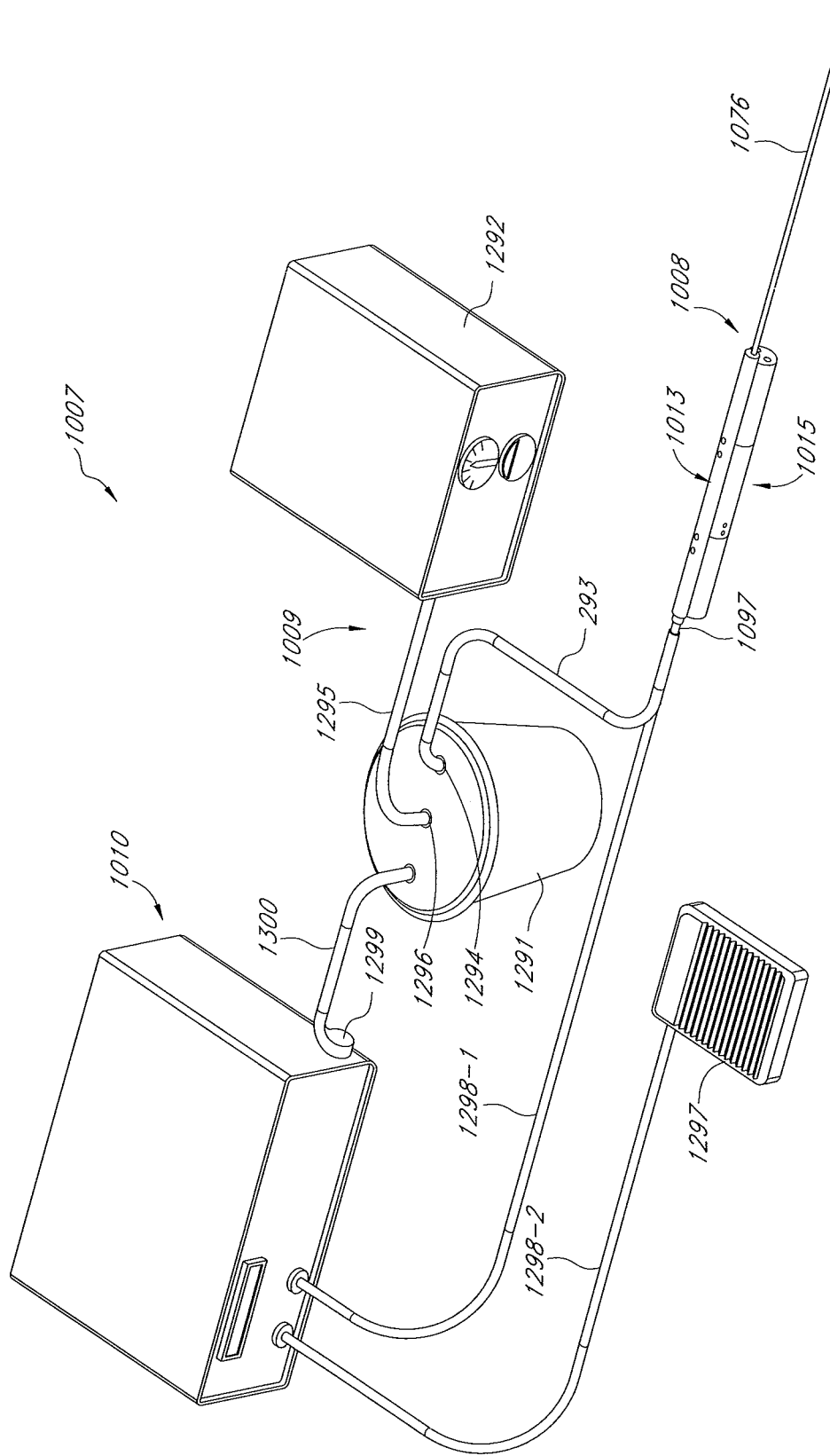
FIG. 27 is a perspective view of a second embodiment of a tissue removal system constructed according to the teachings of the present invention.
Figure 28A:
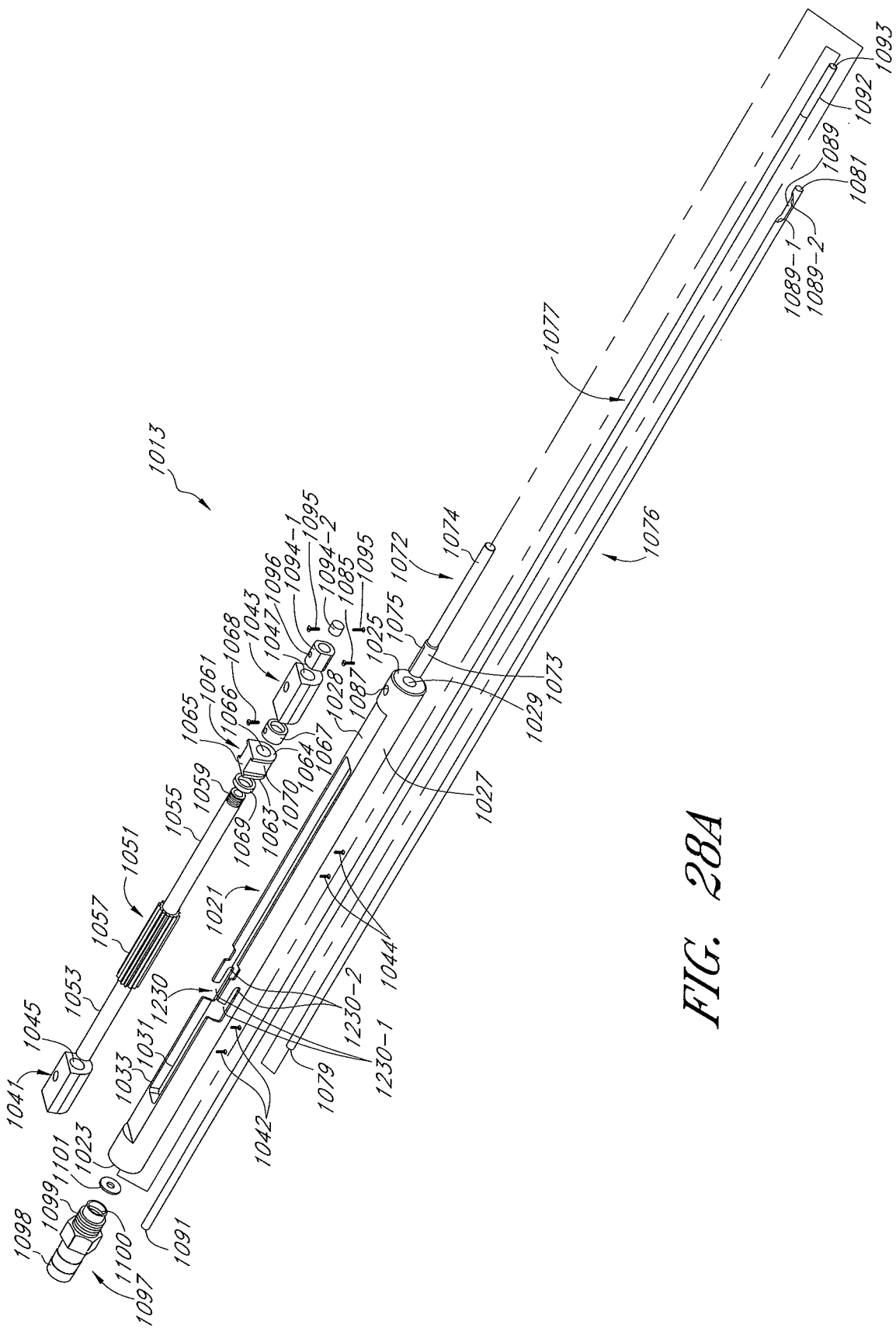
FIGS. 28(a) through 28(d) are bottom exploded perspective, top exploded perspective, bottom partially exploded, and fragmentary, partly in section, side views, respectively, of the morcellator assembly shown in FIG. 27.
Figure 28B:
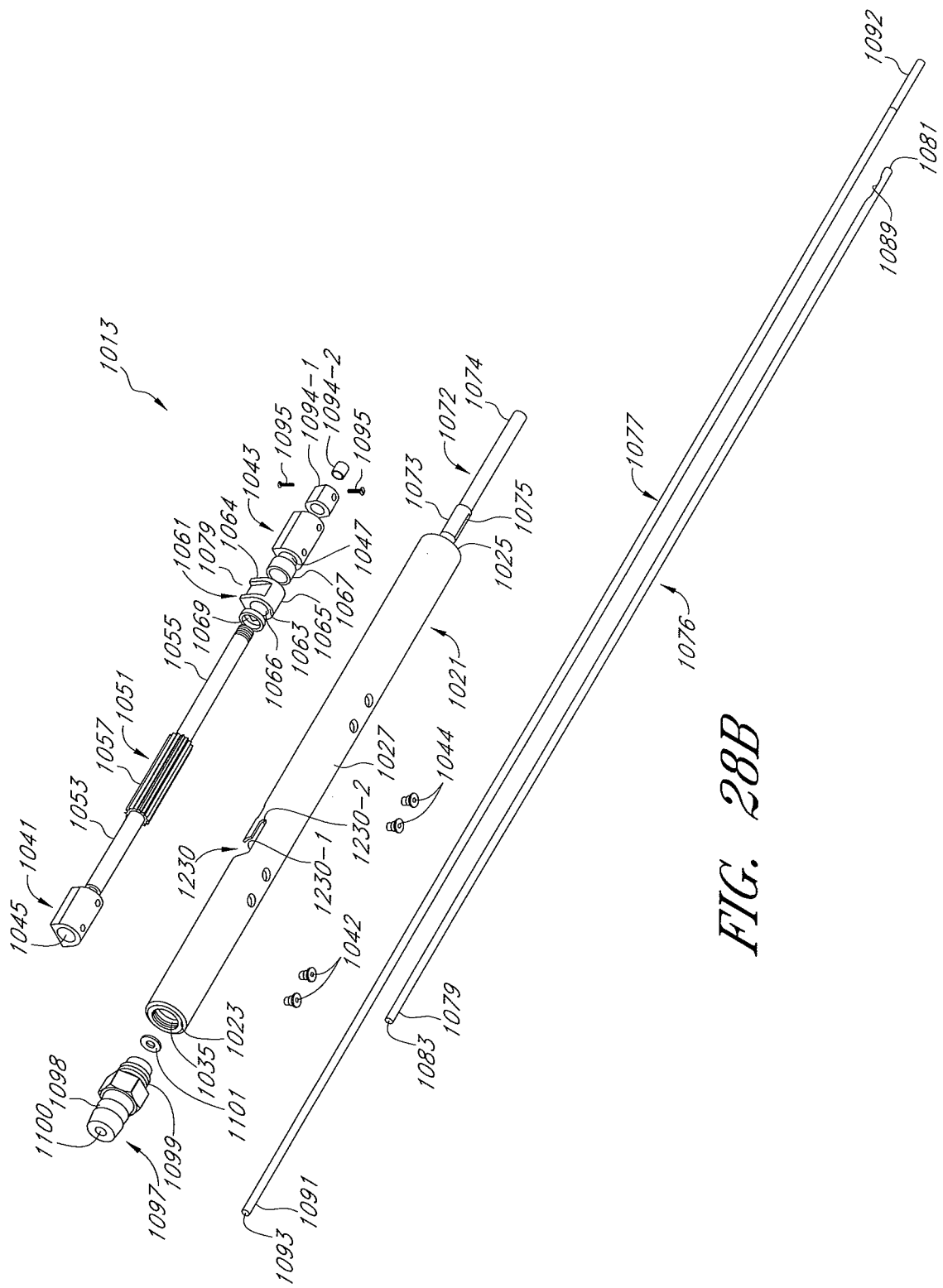
Figure 28C:
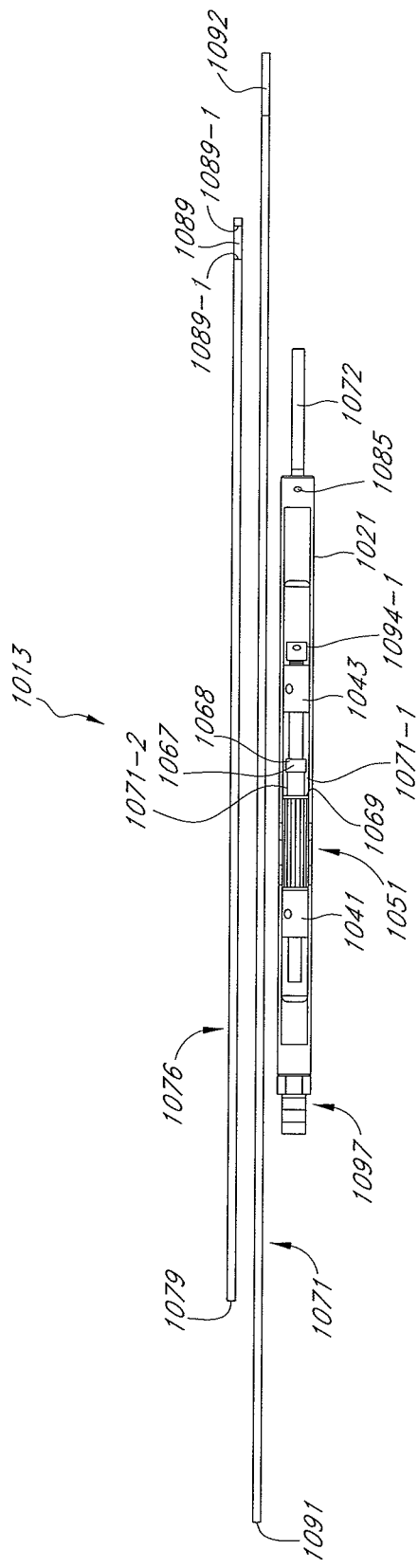
Figure 28D:
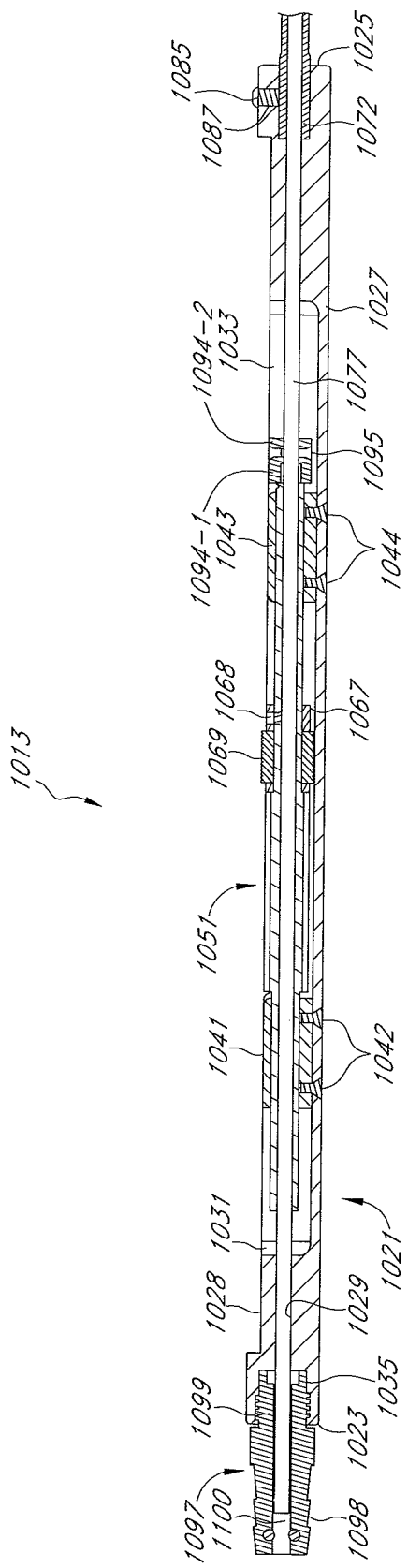

Referring now to FIG. 27, there is shown a partially exploded perspective view of a second embodiment of a tissue removal system, the tissue removal system being constructed according to the teachings of the present invention and being represented generally by reference numeral 1007.

System 1007 may comprise a tissue removal device 1008, a vacuum assembly 1009, and a motor drive assembly 1010. Although not shown in the present embodiment, system 1007 may also include an introducer device, a flexible hysteroscope, and a fluid supply similar to those of system 5 described above.

Tissue removal device 1008 may comprise a morcellator assembly 1013 and a drive assembly 1015, morcellator assembly 1013 being removably mounted on drive assembly 1015 in the manner described further below.

Referring now to FIGS. 28(*a*) through 28(*d*), morcellator assembly 1013 may be seen in greater detail. Morcellator assembly 1013 may comprise a housing 1021. Housing 1021, which may be an elongated unitary structure made of a rigid polymer or metal, may be a generally tubular member shaped to include a proximal end 1023, a distal end 1025, and a side wall 1027. Side wall 1027 may be generally cylindrical, with a portion 1028 of its bottom surface being beveled. A longitudinal lumen 1029 may extend from proximal end 1023 to distal end 1025. An intermediate portion 1031 of lumen 1029 may be expanded in diameter and may be accessible through an opening 1033 in side wall 1027. A proximal portion 1035 of lumen 1029 extending distally from proximal end 1023 to a point spaced proximally from intermediate portion 1031 may be expanded in diameter and may be internally threaded.

Morcellator assembly 1013 may additionally comprise a pair of tubular bushings 1041 and 1043. Bushing 1041, which may be a unitary structure made of a rigid polymer or metal, may be seated within intermediate portion 1031 of lumen 1029, near its proximal end, and may be fixedly secured to housing 1021 with screws 1042. Bushing 1043, which may be a unitary structure made of a rigid polymer or metal, may be seated within intermediate portion 1031 of lumen 1029, near its distal end, and may be fixedly secured to housing 1021 with screws 1044. Bushing 1041 may be shaped to include a bore 1045, and bushing 1043 may be shaped to include a bore 1047, bores 1045 and 1047 being coaxially aligned with lumen 1029 of housing 1021.

Morcellator assembly 1013 may further comprise an elongated shaft 1051. Shaft 1051, which may be a unitary structure made of brass or another suitable rigid metal or polymer, may be shaped to include a proximal portion 1053, a distal portion 1055, an intermediate portion 1057, and a longitudinal bore 1059. Proximal portion 1053 of shaft 1051 may be slidably mounted in bore 1045 of bushing 1041 and may be sized to freely rotate therewithin. Distal portion 1055 of shaft 1051 may be slidably mounted in bore 1047 of bushing 1043 and may be sized to freely rotate therewithin. Intermediate portion 1057 of shaft 1051 may be positioned between bushings 1041 and 1043 and may be in the shape of a gear having an enlarged external diameter relative to proximal portion 1053 and distal portion 1055.

Morcellator assembly 1013 may further comprise a translational coupling block 1061. Block 1061, which may be a unitary structure made of a rigid polymer or metal, may be a tubular member shaped to include a proximal end 1063, a distal end 1064, a side wall 1065, and a longitudinal bore 1066. Block 1061 may be coaxially mounted over proximal portion 1053 of shaft 1051, with bore 1066 being sized relative to proximal portion 1053 so that proximal portion 1053 may freely rotate within bore 1066. Side wall 1065 of block 1061 may be shaped to correspond generally to the shape of intermediate portion 1031 of lumen 1029. In this manner, block 1061 may be kept rotationally stationary within housing 1021. Block 1061 may be translationally fixed relative to shaft 1051 with a retaining ring 1067 inserted coaxially over proximal portion 1053 and secured to proximal portion 1053 with a set screw 1068. A washer 1069 may be inserted coaxially over proximal end 1053 of shaft 1051 between distal end 1063 of block 1061 and intermediate portion 1057 of shaft 1051 to prevent any wear caused by contact between intermediate portion 1057 against distal end 1063 of block 1061 as intermediate portion 1057 rotates. Side wall 1065 of block 1061 may further be shaped to include a waist 1070 of reduced external diameter. In this manner, with block 1061 coaxially mounted over proximal portion 1053 of shaft 1051, a pair of slots 1071-1 and 1071-2 may be formed between block 1061 and housing 1021.

Morcellator assembly 1013 may further comprise a strain relief member 1072. Strain relief member 1072, which may be a unitary structure made of a rigid polymer or metal, may be a tubular member shaped to include a proximal portion 1073 and a distal portion 1074. Proximal portion 1073 may be slightly greater in diameter than distal portion 1074 and may include a bifurcating slot 1075. Proximal portion 1073 of strain relief member 1072 may be disposed within the distal portion of lumen 1029, with distal portion 1074 of strain relief member 1072 extending distally from distal end 1025 of housing 1021 for a short distance, such as, for example, approximately 2 inches.

Morcellator assembly 1013 may further comprise a cutting mechanism. In the present embodiment, the cutting mechanism may comprise an outer tubular member 1076 and an inner tubular member 1077, inner tubular member 1077 moving rotationally and, at the same time, oscillating translationally relative to outer tubular member 1076 in the manner to be described further below. Outer tubular member 1076, which may be a unitary structure made of stainless steel or another similarly suitable material, may be shaped to include an open proximal end 1079, a closed distal end 1081, and a lumen 1083 extending from open proximal end 1079 to a point just prior to closed distal end 1081. Member 1076 may be coaxially mounted within strain relief member 1072, with proximal end 1079 of member 1076 disposed within proximal portion 1073 of strain relief member 1072 and with distal end 1081 of member 1076 extending distally beyond distal portion 1074 of strain relief member 1072 for an extended distance, such as, for example, five inches. The combination of proximal end 1079 of member 1076 and proximal portion 1073 of strain relief member 1072 may be securely retained in housing 1021 using a screw 1085 inserted through an opening 1087 in housing 1021, screw 1085 pressing proximal portion 1073 of strain relief member 1072 tightly against proximal end 1079 of member 1076.

Outer tubular member 1076 may be further shaped to include a resection window 1089 into which tissue may be captured and drawn, window 1089 being located proximate to distal end 1081, such as, for example, 0.25 inch from distal end 1081. Window 1089 may be shaped to include a proximal end 1089-1 and a distal end 1089-2. Proximal end 1089-1 may slope gradually proximally, and distal end 1089-2 may slope gradually distally. More specifically, window 1089 may have a length of approximately 0.55 inch, proximal end 1089-1 may be a radial end having a radius of curvature of, for example, 0.085 inch, and distal end 1089-2 may be a radial end having a radius of curvature of, for example, 0.150 inch. Window 1089 may extend over a substantial portion of the circumference of tubular member 1076, such as, for example, about 60% of the circumference.

Outer tubular member 1076 may have an outer diameter less than about 5.5 mm. However, in order to reduce the risk of injury to the patient and in order to obviate the need for anesthesia to be administered to the patient, outer tubular member 1076 preferably has an outer diameter less than about 5 mm, more preferably less than 4 mm, even more preferably less than 3 mm, and still even more preferably less than 2 mm.

Inner tubular member 1077, which may be an elongated unitary structure made of stainless steel or another similarly suitable material, may be shaped to include a proximal end 1091, a distal end 1092, and a longitudinal lumen 1093. Distal end 1092 may be shaped to include an external bevel, such as, for example, an external bevel of approximately 20 degrees. An intermediate portion of tubular member 1077 may be received within bore 1059 of shaft 1051 and may be fixedly coupled to shaft 1051 for translational and rotational movement therewith using a retaining ring 1094-1, a slotted sleeve 1094-2 and a pair of set screws 1095. The proximal portion of ring 1094-1 may be screwed onto the distal end of shaft 1051, with the distal portion of ring 1094-1 extending over member 1077. Sleeve 1094-2 may be inserted coaxially between member 1077 and ring 1094-1, and set screws 1095 may be inserted through a transverse opening 1096 in retaining ring 1094-1 to couple ring 1094-1 and sleeve 1094-2 to member 1077. Tubular member 1077 may have a suitable length so that, when tubular member 1077 is in a fully retracted (i.e., proximal) position, proximal end 1091 of tubular member 1077 may extend proximally a short distance from proximal end 1023 of housing 1021 and distal end 1092 of tubular member 1077 may be withdrawn sufficiently to permit tissue to enter window 1089. At the same time, tubular member 1077 may have a length so that, when tubular member 1077 is in a fully advanced (i.e., distal) position, distal end 1092 of tubular member 1077 may be positioned distally of distal end 1089-2 of window 1089.

Morcellator assembly 1013 may further comprise a fitting 1097. Fitting 1097, which may be a unitary structure made of a rigid polymer or metal, may be a tubular member shaped to include a proximal portion 1098, a distal portion 1099 and a longitudinal lumen 1100. Proximal portion 1098, which may be barbed, may be coupled through a length of tubing to vacuum assembly 1009. Distal portion 1099 of fitting 1097 may be externally threaded for mating engagement with proximal portion 1035 of housing 1021. Lumen 1100 of fitting 1097 may be dimensioned to slidably receive proximal end 1091 of tubular member 1077. An O-ring 1101 may be disposed within lumen 1100 to provide a seal around tubular member 1077.

Figure 29A:
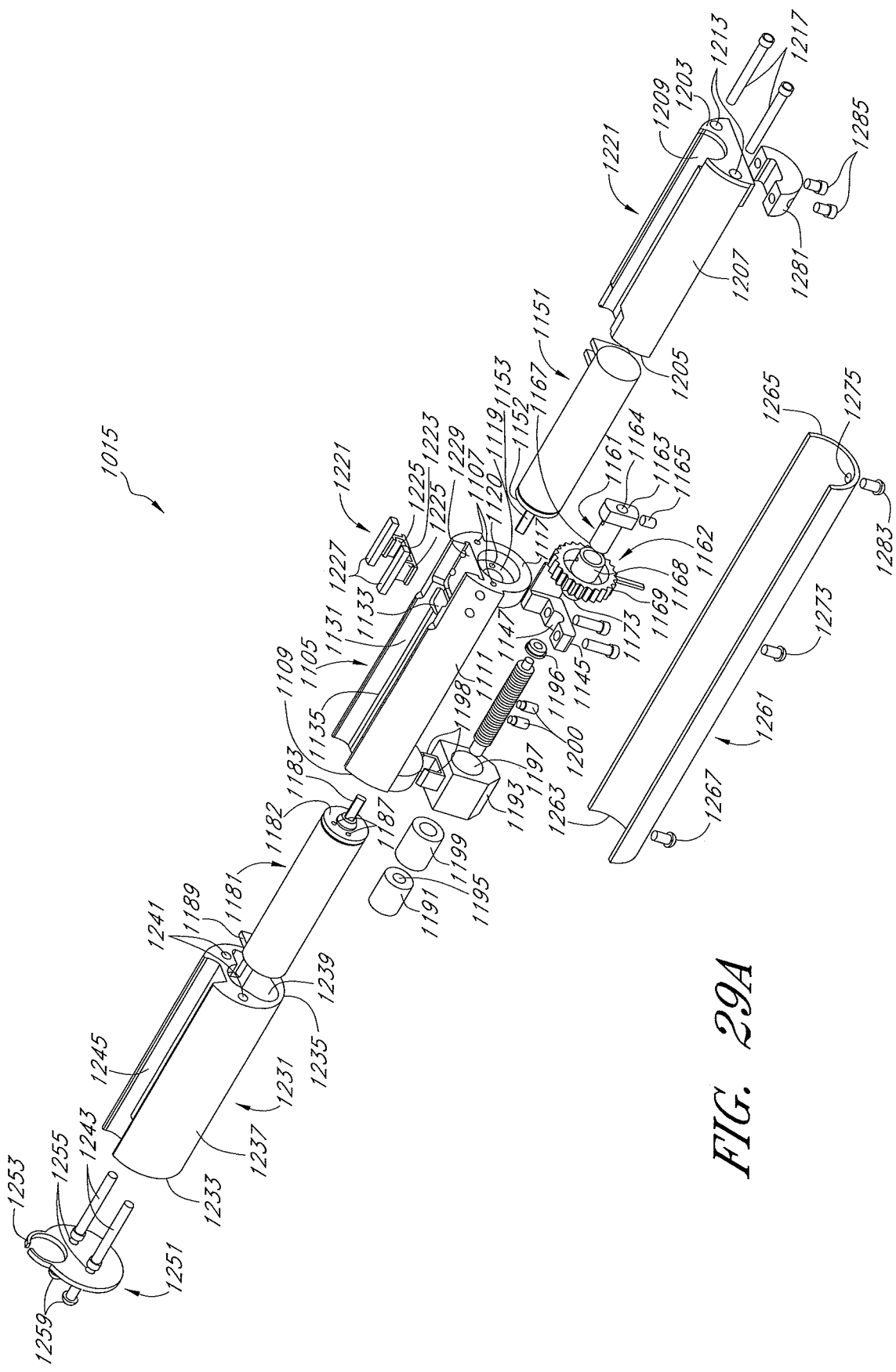
FIGS. 29(a) and 29(b) are partially exploded top perspective and partially exploded bottom perspective views, respectively, of the drive assembly shown in FIG. 27.
Figure 29B:
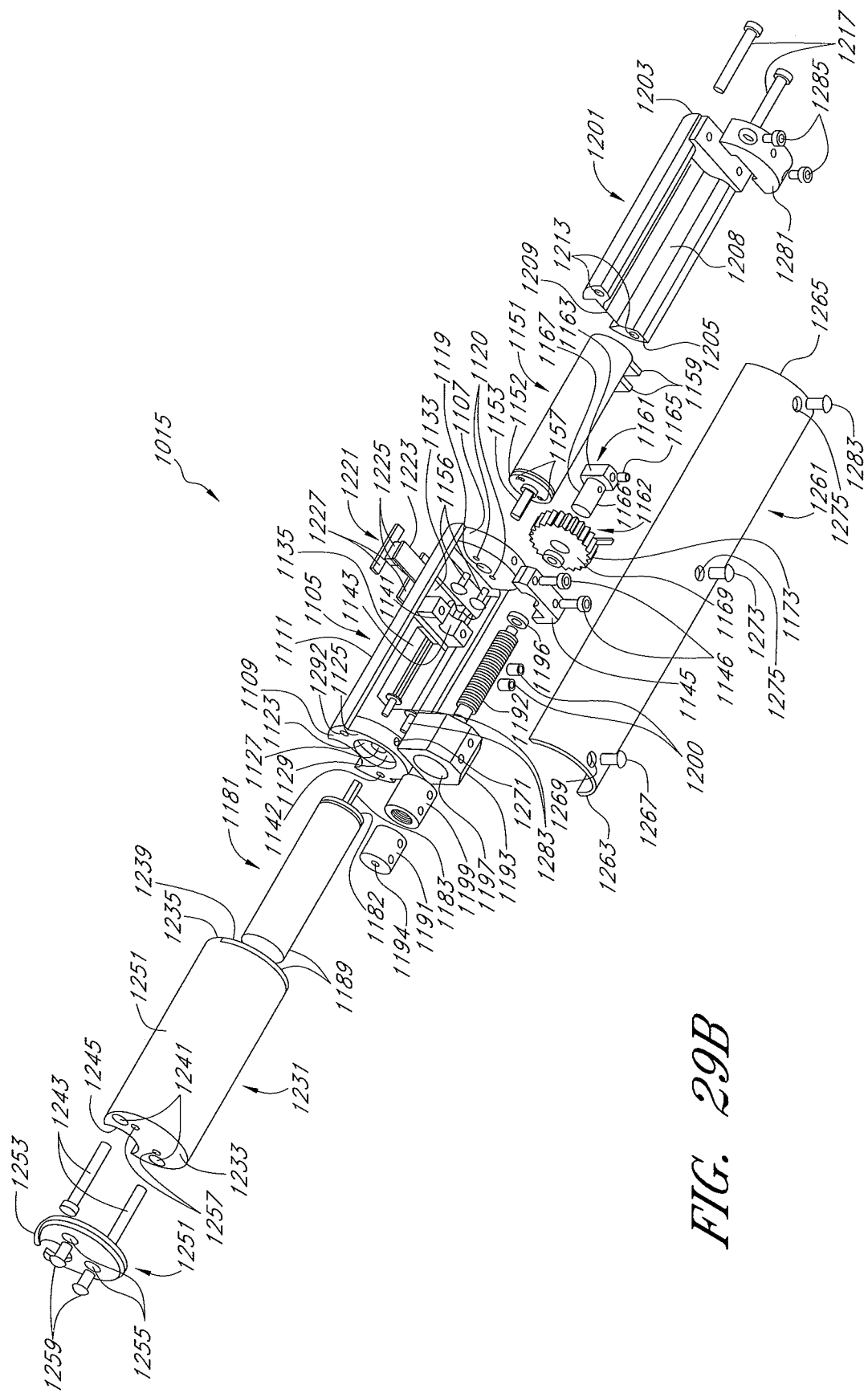

Referring now to FIGS. 29(a) and 29(b), drive assembly 1015 may be seen in greater detail. Drive assembly 1015 may include a main body 1105. Main body 1105, which may be a unitary structure made of a rigid polymer or metal, may be a generally trough-shaped member shaped to include a distal end 1107, a proximal end 1109, and a side wall 1111. Distal end 1107 may be generally circular and may include a distal surface that includes a central portion 1115 and a peripheral portion 1117. Central portion 1115 may be recessed relative to peripheral portion 1117. A central transverse opening 1119 may be provided in central portion 1115, and a pair of smaller transverse openings 1120 may be provided in central portion 1115 on opposite sides of central opening 1119. Proximal end 1109 may be generally circular and may include a proximal surface that includes a central portion 1123 and a peripheral portion 1125. Central portion 1123 may be recessed relative to peripheral portion 1125. A central transverse opening 1127 may be provided in central portion 1123, and a pair of smaller transverse openings 1129 may be provided in central portion 1123 on opposite sides of central opening 1127. Side wall 1111 may extend from distal end 1107 to proximal end 1109 but only over about the top half of their respective circumferences. A longitudinal groove 1131 may be provided along the outer surface of side wall 1111 to receive a corresponding portion of housing 1021 of morcellator assembly 1013. Groove 1131 may include a first transverse slot 1133 extending though side wall 1111 and a second transverse slot 1135 extending through side wall 1111. First transverse slot 1133 may be spaced a short distance from distal end 1107 and may be oriented generally circumferentially relative to side wall 1111. Second transverse slot 1135 may be spaced a short distance from proximal end 1109 and from first transverse slot 1133 and may be oriented generally longitudinally relative to side wall 1111. The inner surface of side wall 1111 may additionally be shaped to include a block 1141 located between first transverse slot 1133 and second transverse slot 1135. Block 1141 may be shaped to include an exterior groove 1143 on its bottom surface, groove 1143 extending parallel to second transverse slot 1135. A bracket 1145, which may be a unitary structure made of a rigid polymer or metal, may be secured to the bottom surface of block 1141 with a pair of screws 1146. Bracket 1145 may be shaped to include a groove 1147 on its top surface that is complementarily shaped to groove 1143, with grooves 1143 and 1147 jointly defining a channel of generally cylindrical shape.

Drive assembly 1015 may additionally comprise a mechanism for driving rotational movement of inner tubular member 1077. Such a mechanism may comprise a first motor 1151. Motor 1151, in turn, may comprise a first end 1152 having a shaft 1153 extending therefrom. First end 1152 may be received within central portion 1115 of distal end 1107 of body 1105 and may be secured thereto with screws 1156 inserted through openings 1120 and into complementary openings 1157 in first end 1152 of motor 1151. With motor 1151 thus secured to distal end 1107, shaft 1153 may extend through central transverse opening 1119 and may freely rotate therewithin. Cables 1159 may be used to connect motor 1151 to control unit 1010.

In addition, the aforementioned mechanism for driving rotational movement of inner tubular member 1077 may further comprise a coupling block 1161 and a gear 1162. Coupling block 1161, which may be a unitary structure made of a rigid polymer or metal, may be shaped to include a distal base 1163 and a proximal post, the proximal post extending proximally from base 1163. Base 1163 may be shaped to include a cavity 1164 accessible from its distal end into which shaft 1153 of motor 1151 may be received and secured with a screw 1165, thereby mechanically coupling shaft 1153 to block 1161. The proximal post may be shaped to include a distal portion 1166 of increased diameter and a proximal portion 1167 of decreased diameter. Gear 1162, which may be a unitary member made of a rigid polymer or metal, may be shaped to include a distal tube 1168 and a proximal toothed wheel 1169. Tube 1168 may be coaxially mounted on portion 1166 of block 1161 and mechanically coupled thereto with a screw 1170. Wheel 1169 may be positioned so that a portion of wheel 1169 extends through slot 1133 for engagement with intermediate portion 1057 of shaft 1051. In this manner, rotation of wheel 1169 causes the rotation of shaft 1051. Proximal portion 1167 of post 1165, which may extend proximally a short distance beyond wheel 1169, may be seated within a bearing 1173, bearing 1173 being seated within the distal end of the channel jointly defined by block 1141 and bracket 1145.

Drive assembly 1015 may further comprise a mechanism for driving oscillating translational movement of inner tubular member 1077. Such a mechanism may comprise a second motor 1181. Motor 1181, in turn, may comprise a first end 1182 having a shaft 1183 extending therefrom. First end 1182 may be received within central portion 1123 of proximal end 1109 of body 1105 and may be secured thereto with screws 1186 inserted through openings 1129 and into complementary openings 1187 in first end 1182 of motor 1181. With motor 1181 thus secured to proximal end 1109, shaft 1183 may extend through central transverse opening 1127 and may freely rotate therewithin. A cable 1189 may be used to connect motor 1181 to control unit 1010.

In addition, the aforementioned mechanism for driving oscillating translational movement of inner tubular member 1077 may further comprise a coupling block 1191, a threaded bolt 1192, and a carriage 1193. Coupling block 1191, which may be a unitary structure made of a rigid polymer or metal, may be shaped to include a proximal opening 1194 and a distal opening 1195. Proximal opening 1194 may be dimensioned to securely receive shaft 1183 of motor 1181, thereby mechanically coupling shaft 1183 to block 1191. Distal opening 1195 may be dimensioned to securely receive the proximal end of threaded bolt 1192, thereby mechanically coupling bolt 1192 to block 1191. The distal end of bolt 1192 may be seated within a bearing 1196, which, in turn, may be seated within the proximal end of the channel jointly defined by block 1141 and bracket 1145. Carriage 1193, which may be a unitary structure made of a rigid polymer or metal, may be shaped to include a bore 1197 and a pair of upwardly extending tines 1198. A rigid collar 1199 may be fixedly mounted within bore 1197 of carriage 1193 using a pair of screws 1200. Collar 1199 may be internally threaded to engage bolt 1192. In this manner, as bolt 1192 rotates, carriage 1193 moves translationally along the longitudinal axis of bolt 1192, with proximal or distal translational movement of carriage 1193 effected by the clockwise or counterclockwise rotation, respectively, of bolt 1192. Carriage 1193 may be mechanically coupled for translational movement to shaft 1051 by tines 1198, with tines 1198 extending through slot 1135 of body 1105 and being received within slots 1071-1 and 1071-2 of morcellator assembly 1013.

As can be appreciated from the above description, the speed at which inner tubular member 1077 rotates and the speed at which inner tubular member 1077 oscillates translationally are separately and independently controlled, with the rotation of inner tubular member 1077 being controlled by motor 1151 and with the oscillating translation of inner tubular member 1077 being controlled by motor 1181.

Drive assembly 1015 may further comprise a body 1201. Body 1201, which may be a unitary structure made of a rigid polymer or metal, may be shaped to include a distal end 1203, a proximal end 1205, a side wall 1207, and a cavity 1208. Distal end 1203 may be generally semi-circular in shape, and proximal end 1205 may be generally semi-annular in shape. Side wall 1207 may be semi-annular in transverse cross-section and may extend from distal end 1203 to proximal end 1205. A longitudinal groove 1209, similar in shape to groove 1131 of body 1105, may be provided along the top, outer surface of side wall 1207 to receive a corresponding portion of housing 1021 of morcellator assembly 1013. Cavity 1208 may be dimensioned to receive motor 1151. A pair of longitudinal lumens 1213 may be provided in body 1201, lumens 1213 extending through distal end 1203, proximal end 1205, and side wall 1207. Lumens 1213 may be aligned with corresponding threaded cavities 1215 in body 1105 so that proximal end 1205 of body 1201 may be fixed to distal end 1107 of body 1105 using screws 1217 inserted through body 1201 and into cavities 1215.

Drive assembly 1015 may further comprise a locking clip 1221. Locking clip 1221, which may be a unitary structure made of a rigid polymer or metal, may be shaped to include a base 1223, a pair of parallel legs 1225, and a pair of parallel feet 1227. Legs 1225 may extend upwardly from base 1223, with legs 1225 being spaced inwardly a short distance from the ends of base 1223. Feet 1227 may extend transversely from legs 1225. Base 1223 may be received within a matingly-shaped recess 1229 provided on body 1105 and may be securely retained within recess 1229 by securing body 1201 to body 1105. With clip 1221 thus mounted on body 1105, legs 1225 extend upwardly beyond body 1105 and may be inserted into corresponding L-shaped slots 1230 in housing 1021 of morcellator assembly 1013. In this manner, clip 1221 may be used to reversibly and lockably couple drive assembly 1015 to morcellator assembly 1013. More specifically, to lockably couple drive assembly 1015 to morcellator assembly 1013, one may insert feet 1227 into the proximal portions 1230-1 of slots 1230 and may then slide feet 1227 distally to the distal portions 1230-2 of slots 1230. To uncouple drive assembly 1015 from morcellator 1013, feet 1227 may be slid proximally from distal portions 1230-2 to proximal portions 1230-1 and may then be removed from slots 1230.

Drive assembly 1015 may further comprise a body 1231. Body 1231, which may be a unitary structure made of a rigid polymer or metal, may be a generally cylindrical member shaped to include a proximal end 1233, a distal end 1235, and a side wall 1237. A cavity 1239 may extend proximally from distal end 1235, cavity 1239 being dimensioned to receive substantially all but first end 1182 and shaft 1183 of motor 1181. A pair of longitudinal lumens 1241 may be provided in body 1231, lumens 1241 extending through proximal end 1233, distal end 1235, and side wall 1237. Lumens 1241 may be aligned with corresponding threaded cavities 1242 in body 1105 so that distal end 1235 of body 1231 may be fixed to proximal end 1109 of body 1105 using screws 1243 inserted through body 1231 and into cavities 1242. A groove 1245 may extend longitudinally from proximal end 1233 to distal end 1235 along the top surface of side wall 1237. Groove 1245 may be aligned with groove 1131 of body 1105 in order to receive a corresponding portion of housing 1021 of morcellator assembly 1013.

Drive assembly 1015 may further comprise an endplate 1251. Endplate 1251, which may be a unitary structure made of a rigid polymer or metal, may be a generally disc-shaped structure shaped to include a retaining loop 1253 at its top. Retaining loop 1253 may be dimensioned to receive the proximal end of housing 1021 of morcellator assembly 1013. A pair of openings 1255 may be provided in endplate 1251. Openings 1255 may be aligned with corresponding threaded cavities 1257 in body 1231 so that endplate 1241 may be fixed to proximal end 1233 of body 1231 using screws 1259 inserted through endplate 1241 and into cavities 1257.

Drive assembly 1015 may further comprise a cover 1261. Cover 1261, which may be a unitary structure made of a rigid polymer or metal, may be in the shape of a half-pipe having a proximal end 1263 and a distal end 1265. Cover 1261 may be dimensioned to complement side walls 1111 and 1207 of bodies 1105 and 1201, respectively. In addition, cover 1261 may be fixed to body 1105 with a screw 1267 inserted through an opening 1269 in cover 1261 and into a corresponding cavity 1271 in proximal end 1109 of body 1105 and with a screw 1273 inserted through an opening 1275 in cover 1261 and into a corresponding cavity 1277 in distal end 1107 of body 1105. Additionally, cover 1261 may be fixed to body 1201 by joining cover 1261 to a block 1281 using a screw 1283 and by joining block 1281 to distal end 1203 of body 1201 using a pair of screws 1285.

Referring back now to FIG. 27, vacuum assembly 1009 may include a specimen collection container 1291 and a vacuum source 1292. The distal end of an evacuation tube 1293 may be inserted over fitting 1097 and may be secured thereto by a friction fit, and the proximal end of evacuation tube 1293 may be coupled to a first port 1294 of container 1291. The distal end of a tube 1295 may be coupled to a second port 1296 of container 1291, and the proximal end of tube 1295 may be coupled to vacuum source 1292. In this manner, vacuum source 1292 may be used to apply suction to device 1008, and any withdrawn tissue, liquids or similar matter suctioned through device 1008 may be collected in container 1291.

Control unit 1010, which may be coupled to a source of electricity, such as an AC wall outlet, using a power cord (not shown), may include electronics (not shown) for controlling the operation of motors 1151 and 1181 using a cable 1298-1 connected to cables 1159 and 1189. A foot pedal 1297 may be coupled to control unit 1010 by a cable 1298-2 and may be used as a power switch to selectively activate or de-activate motors 1151 and 1181. Control unit 1010 may further include a vacuum sensor 1299, which may be coupled to container 1291 by a tube 1300, so that the pressure within container 1291 may be monitored by control unit 1010. In this manner, a sudden increase in vacuum pressure may indicate that a clog has occurred. The presence of a clog may be indicated via an alarm (not shown) located on control unit 1010. The detection of a clog is often a clear indication that the further operation of device 1008 may only aggravate the clogging situation and that a cessation of tissue removal may be necessary. Control unit 1010 may be configured to synchronize actuation of drive assembly 1015 with actuation of vacuum source 1292. In this manner, turning on drive assembly 1015 will turn on vacuum source 1292 at the same time. Correspondingly, vacuum source 1292 may be deactivated whenever drive assembly 1015 is turned off.

In use, the distal end of a hysteroscope may be inserted transcervically into a patient, and a suitable fluid may be conducted through the inlet fluid port of the hysteroscope into the uterus until the uterus is distended. Observation of the uterus and detection of fibroids or other abnormal gynecological tissues may then be performed using the visualization channel of the hysteroscope. The distal ends of outer tubular member 1076 and inner tubular member 1077 may be inserted through a working channel of the hysteroscope and into the uterus, with the remainder of system 1007 remaining proximal to the hysteroscope. Device 1008 may then be manipulated so that window 1089 of outer tubular member 1076 may be positioned in proximity to the fibroid or other targeted tissue. Next, vacuum source 1292 may be operated so as to cause suction to be applied to inner tubular member 1077, thereby drawing tissue into outer tubular member 1076 through window 1089. In addition, motors 1151 and 1181 may be operated so as to cause inner tubular member 1077 simultaneously to rotate and to oscillate back and forth translationally within outer tubular member 1076, thereby causing the tissue drawn through window 1089 to be cut. The cut tissue may then be suctioned from the patient through inner tubular member 1077 by means of the aforementioned suction and, thereafter, collected in container 1291. Once the fibroids or other targeted tissues have thus been removed from the patient, vacuum source 1292 and motors 1151 and 1181 may be turned off, device 1008 may be withdrawn from the hysteroscope, and the hysteroscope may be withdrawn from the patient. Morcellator assembly 1013 may then be detached from drive assembly 1015 and disconnected from vacuum source 1292. Morcellator assembly 1013 may be designed to be a single use device and, if so, may be disposed of after being used on a patient. By contrast, drive assembly 1015 may be used on a number of different patients prior to its disposal, with a different morcellator assembly 1013 preferably being used with each patient.

It should be noted that, although the above-discussion contemplates inserting device 1008 through the working channel of a hysteroscope, one may insert device 1008 transcervically into the uterus without the use of a hysteroscope. In such a situation, fluid may be administered transcervically to the uterus by a fluid dispensing device in order to distend the uterus, and, thereafter, observation of the uterus may be accomplished, for example, by ultrasonic imaging using an ultrasonic probe inserted transcervically into the uterus. Such an ultrasonic probe may be separate from device 1008 or may be integrated into device 1008. Alternatively, imaging of the uterus may be performed by MRI imaging.

Figure 30:
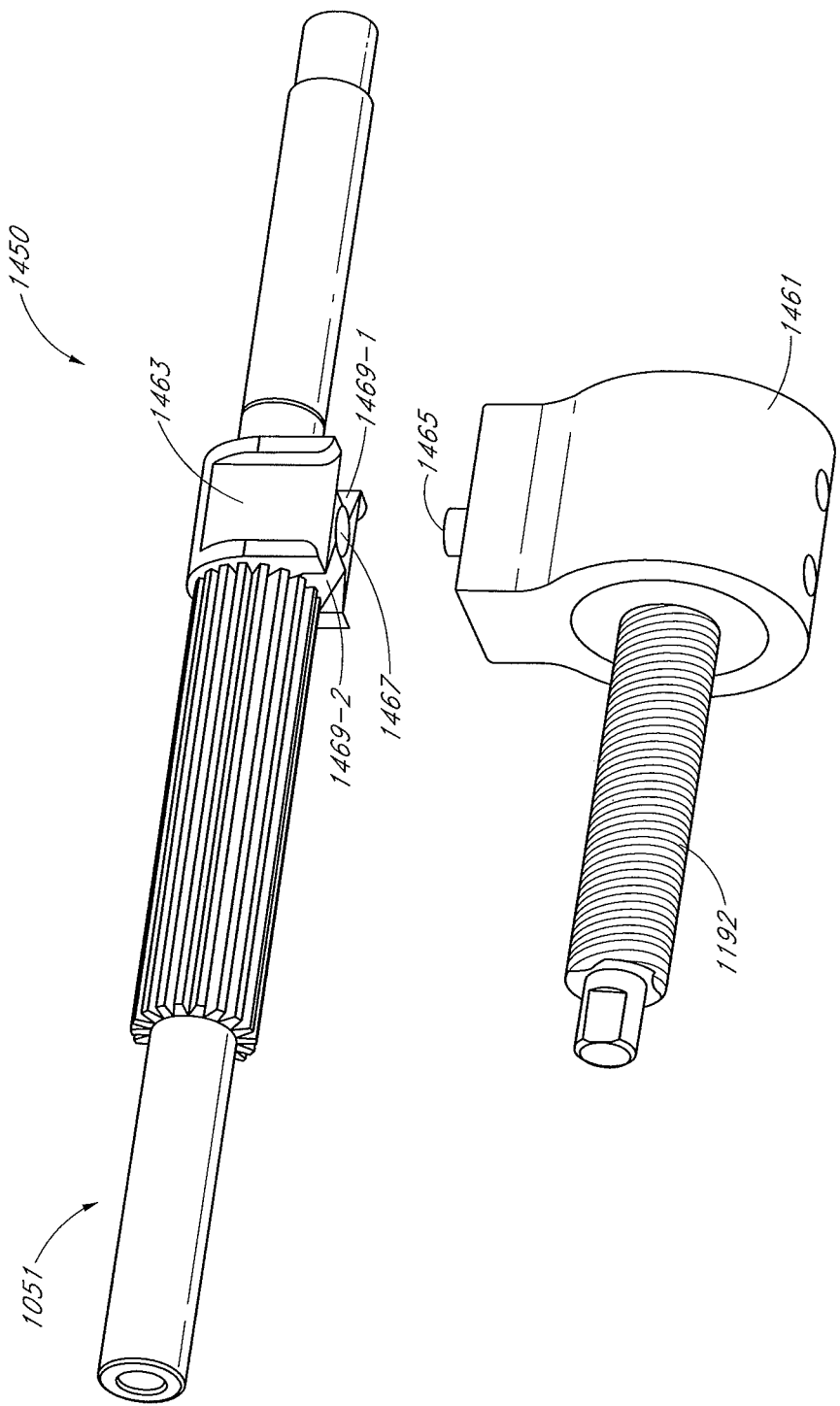
FIG. 30 is a fragmentary, partially exploded, perspective view of an alternate tissue removal device that may be used in the tissue removal system of FIG. 27.

Referring now to FIG. 30, there is shown a fragmentary exploded perspective view of an alternate tissue removal device adapted for use in system 1007, said tissue removal device being represented generally by reference numeral 1450. For simplicity and clarity, certain aspects of device 1450 not important to an understanding of the invention are neither shown nor described herein.

Device 1450 may be similar in most respects to device 1008, the principal differences between the two devices being that carriage 1193 and translational coupling block 1061 of device 1008 may be replaced with carriage 1461 and translational coupling block 1463, respectively, of device 1450. Carriage 1461 of device 1450 may be similar in many respects to carriage 1193 of device 1008, the principal difference between the two carriages being that carriage 1461 may include an upwardly biased spring-loaded pin 1465. Translational coupling block 1463 of device 1450 may be similar in many respects to translation coupling block 1061 of device 1008, the principal differences between the two blocks being that (i) translation coupling block 1463 may be shaped to include a cavity 1467 adapted to receive pin 1465 and (ii) translation coupling block 1463 may be shaped to include ramped surfaces 1469-1 and 1469-2 sloping downwardly towards the open end of cavity 1467 from the proximal and distal ends, respectively, of translation coupling block 1463. In use, the morcellator assembly, which comprises translation coupling block 1463, may be attached to the drive assembly, which comprises carriage 1461, and the translational motor of device 1008 may be actuated to move carriage 1461 translationally back and forth one complete cycle. Regardless of where carriage 1461 and translational coupling block 1463 may be initially positioned translationally relative to one another, as carriage 1461 is moved translationally one complete cycle, pin 1465 is automatically assured of being aligned with cavity 1467. For example, if pin 1465 is initially positioned proximally relative to translation coupling block 1463, as carriage 1461 is moved distally, the top surface of pin 1465 travels across ramped surface 1469-1 and is then received in cavity 1467. One advantage of this arrangement is that pin 1465 and cavity 1467 need not be aligned with one another as the morcellator assembly and the drive assembly are attached to one other. As can be appreciated, because the morcellator assembly may be a single-use item whereas the drive assembly may be a reusable item, pin 1465 and cavity 1467 may not initially be aligned with one another.

Figure 31A:
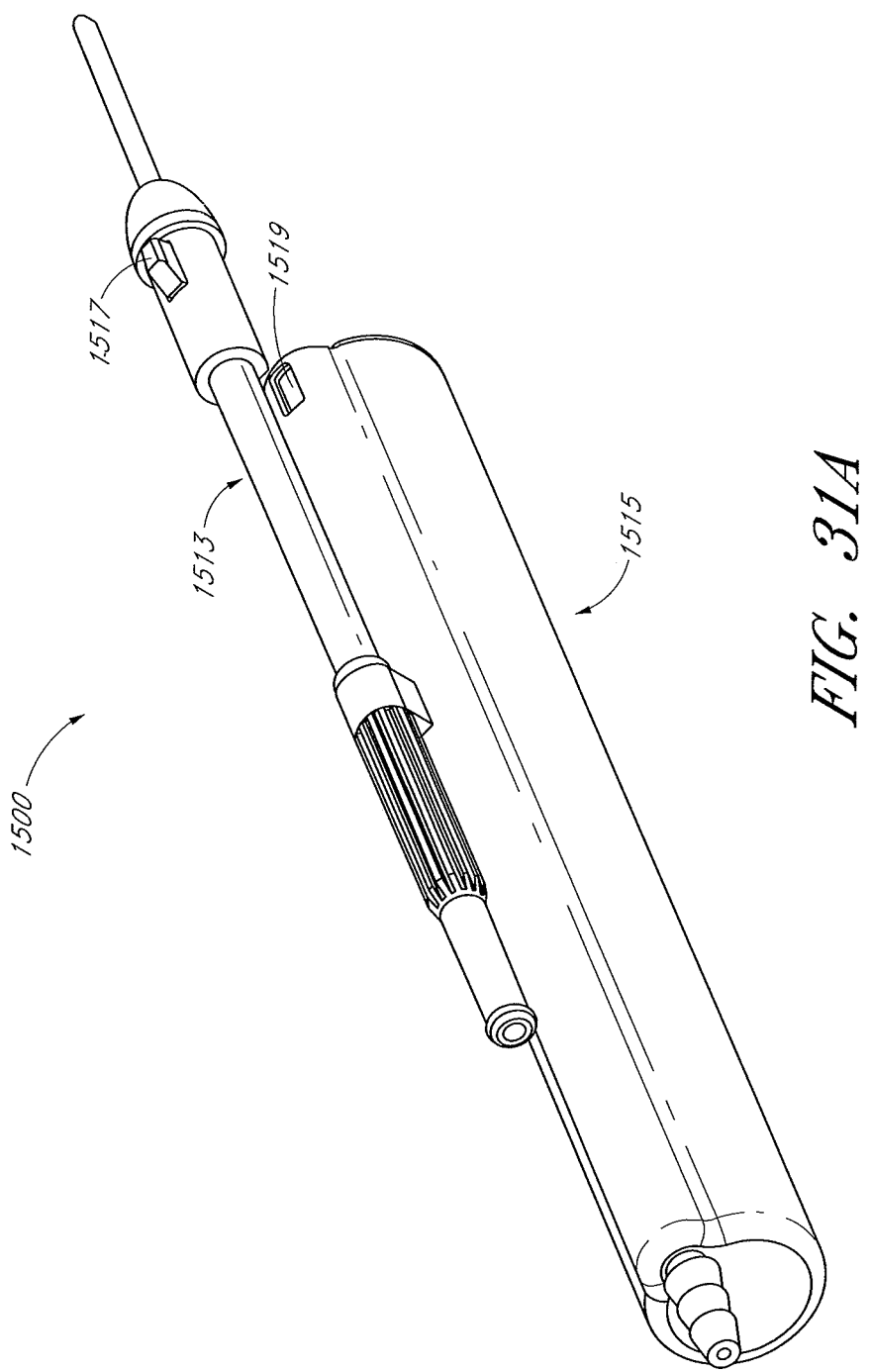
FIGS. 31(a) and 31(b) are fragmentary, partially exploded, perspective views of another alternate tissue removal device that may be used in the tissue removal system of FIG. 27.
Figure 31B:
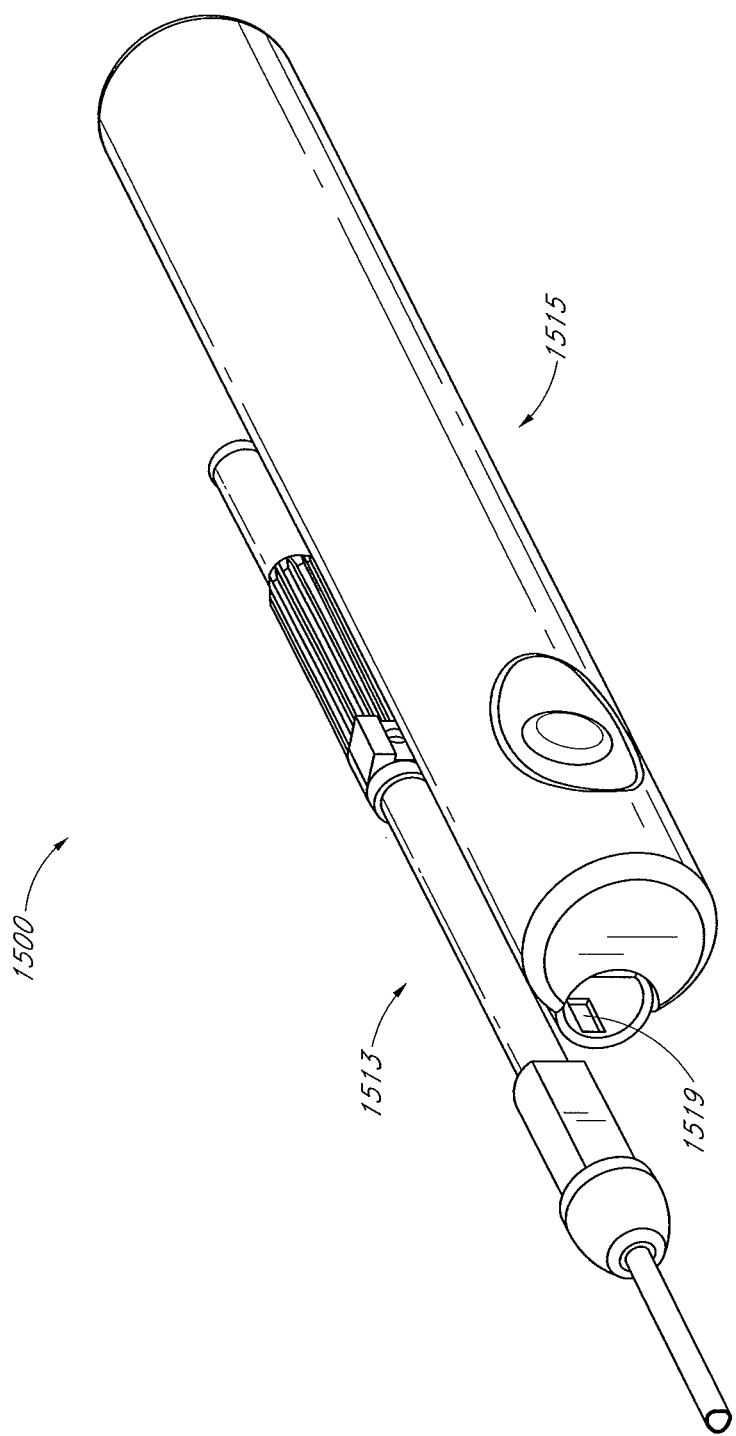

Referring now to FIGS. 31(*a*) and 31(*b*), there are shown fragmentary, partially exploded, perspective views of another alternate tissue removal device adapted for use in system 1007, said tissue removal device being represented generally by reference numeral 1500. For simplicity and clarity, certain aspects of device 1500 not important to an understanding of the invention are neither shown nor described herein.

Device 1500 may comprise a morcellator assembly 1513 and a drive assembly 1515. Morcellator assembly 1513 and drive assembly 1515 may be similar in most respects to morcellator assembly 1013 and drive assembly 1015, respectively, the principal differences between the respective morcellator assemblies and drive assemblies being that morcellator assembly 1513 and drive assembly 1515 may be detachably matingly secured to one another by means of a detent 1517 provided on morcellator assembly 1513 and a slot 1519 provided in drive assembly 1515. Accordingly, when one wishes to use device 1500, detent 1517 of morcellator assembly 1513 is preferably inserted into slot 1519 of drive assembly 1515, thereby physically and operatively coupling together morcellator assembly 1513 and drive assembly 1515. Device 1500 may then be used in the same manner discussed above in connection with device 1008. After device 1500 has been used, morcellator assembly 1513 may be separated from drive assembly 1515, for example, by pulling apart their respective proximal ends until detent 1517 is removed from slot 1519. If desired, morcellator assembly 1513 may then be disposed of whereas drive assembly 1515 may be reused.

Figure 32:
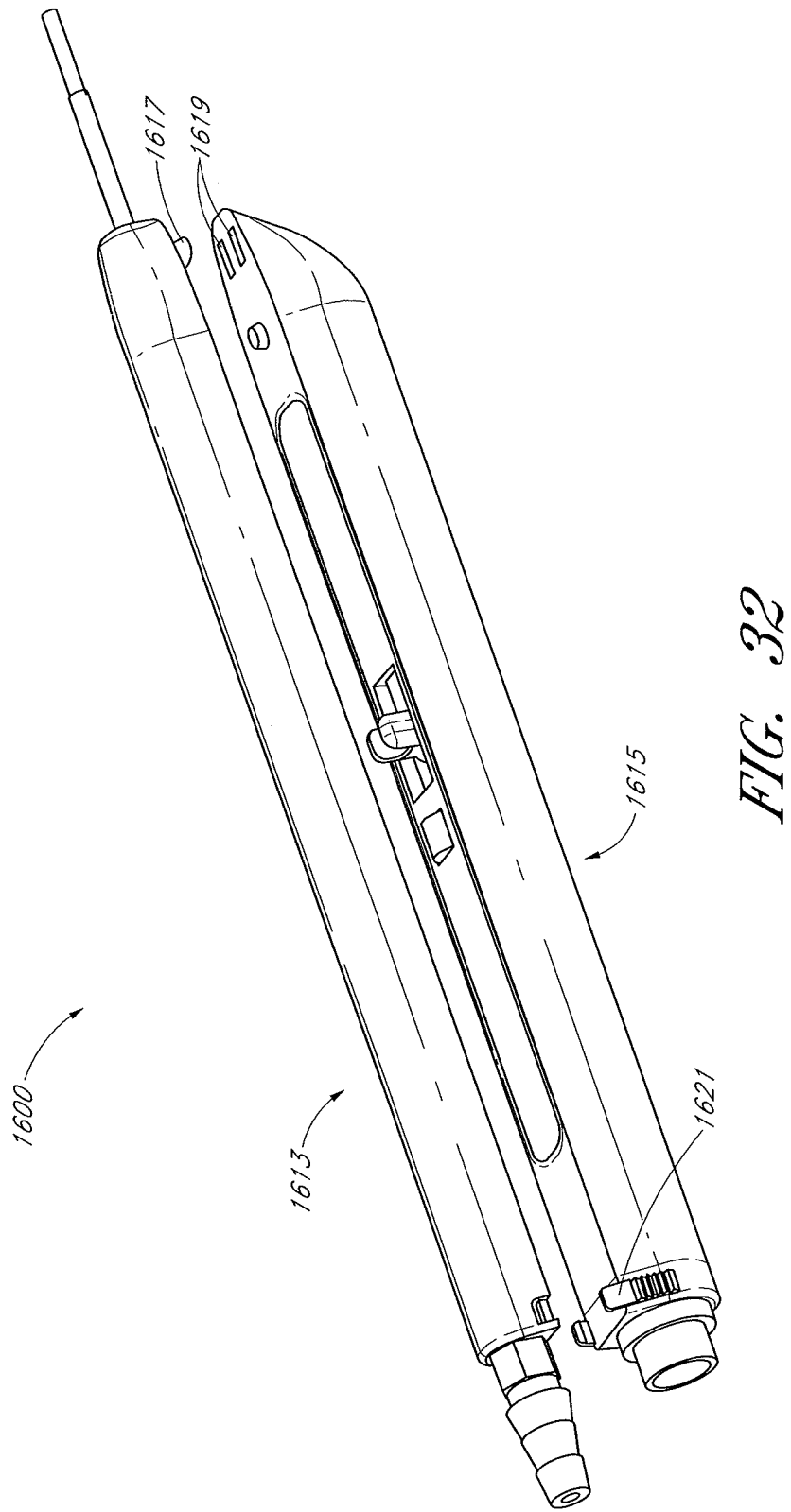
FIG. 32 is a fragmentary, partially exploded, perspective view of another alternate tissue removal device that may be used in the tissue removal system of FIG. 27.

Referring now to FIG. 32, there is shown a fragmentary, partially exploded, perspective view of another alternate tissue removal device adapted for use in system 1007, said tissue removal device being represented generally by reference numeral 1600. For simplicity and clarity, certain aspects of device 1600 not important to an understanding of the invention are neither shown nor described herein.

Device 1600 may comprise a morcellator assembly 1613 and a drive assembly 1615. Morcellator assembly 1613 and drive assembly 1615 may be similar in most respects to morcellator assembly 1013 and drive assembly 1015, respectively, the principal differences between the respective morcellator assemblies and drive assemblies being that morcellator assembly 1613 and drive assembly 1615 may be detachably secured to one another by means of hooks 1617 provided on morcellator assembly 1613 near its distal end and corresponding slots 1619 provided in drive assembly 1615 near its distal end. In addition, drive assembly 1615 may further comprise a spring retention member 1621 at its proximal end for engaging the proximal end of morcellator 1613. Accordingly, when one wishes to use device 1600, hooks 1617 of morcellator assembly 1613 are preferably inserted into slots 1619 of drive assembly 1615 and then spring retention member 1621 engages the proximal end of morcellator assembly 1613, thereby physically and operatively coupling together morcellator assembly 1613 and drive assembly 1615. Device 1600 may then be used in the same manner discussed above in connection with device 1008. After device 1600 has been used, morcellator assembly 1613 may be separated from drive assembly 1615, for example, by pulling apart their respective proximal ends until hooks 1617 are removed from slots 1619. If desired, morcellator assembly 1613 may then be disposed of whereas drive assembly 1615 may be reused.

Figure 33:
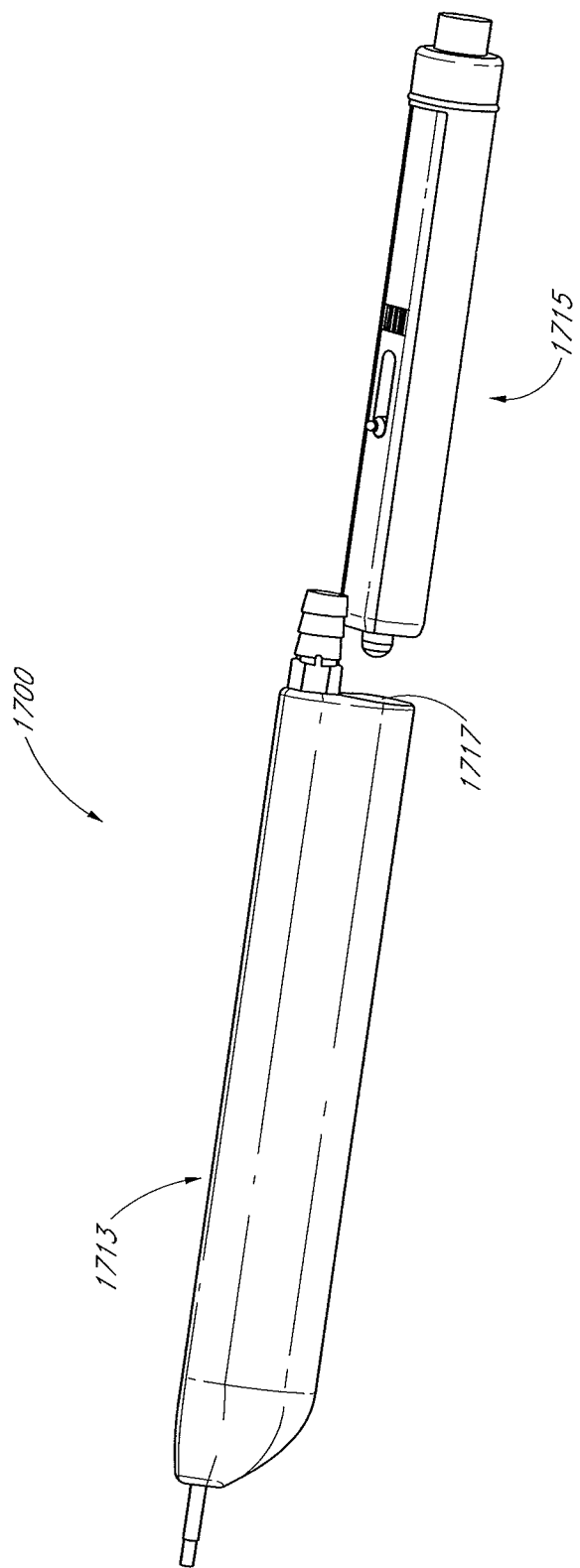
FIG. 33 is a fragmentary, partially exploded, perspective view of another alternate tissue removal device that may be used in the tissue removal system of FIG. 27.

Referring now to FIG. 33, there is shown a fragmentary, partially exploded, perspective view of another alternate tissue removal device adapted for use in system 1007, said tissue removal device being represented generally by reference numeral 1700. For simplicity and clarity, certain aspects of device 1700 not important to an understanding of the invention are neither shown nor described herein.

Device 1700 may comprise a morcellator assembly 1713 and a drive assembly 1715. Morcellator assembly 1713 and drive assembly 1715 may be similar in many respects to morcellator assembly 1013 and drive assembly 1015, respectively, the principal differences between the respective morcellator assemblies and drive assemblies being that (i) morcellator assembly 1713 may be shaped to include a cavity 1717 and (ii) drive assembly 1715 may be shaped to be removably received within cavity 1717 of morcellator assembly 1713. (Although not shown, morcellator assembly 1713 and/or drive assembly 1715 preferably includes a mechanism for releasably retaining drive assembly 1715 within cavity 1717.) Accordingly, when one wishes to use device 1700, drive assembly 1715 is preferably inserted into cavity 1717 of morcellator assembly 1713 until morcellator assembly 1713 and drive assembly 1715 are physically and operatively coupled to one another. Device 1700 may then be used in the same manner discussed above in connection with device 1008. After device 1700 has been used, drive assembly 1715 may be withdrawn from cavity 1717 of morcellator assembly 1713. If desired, morcellator assembly 1713 may then be disposed of whereas drive assembly 1715 may be reused.

Figure 34:
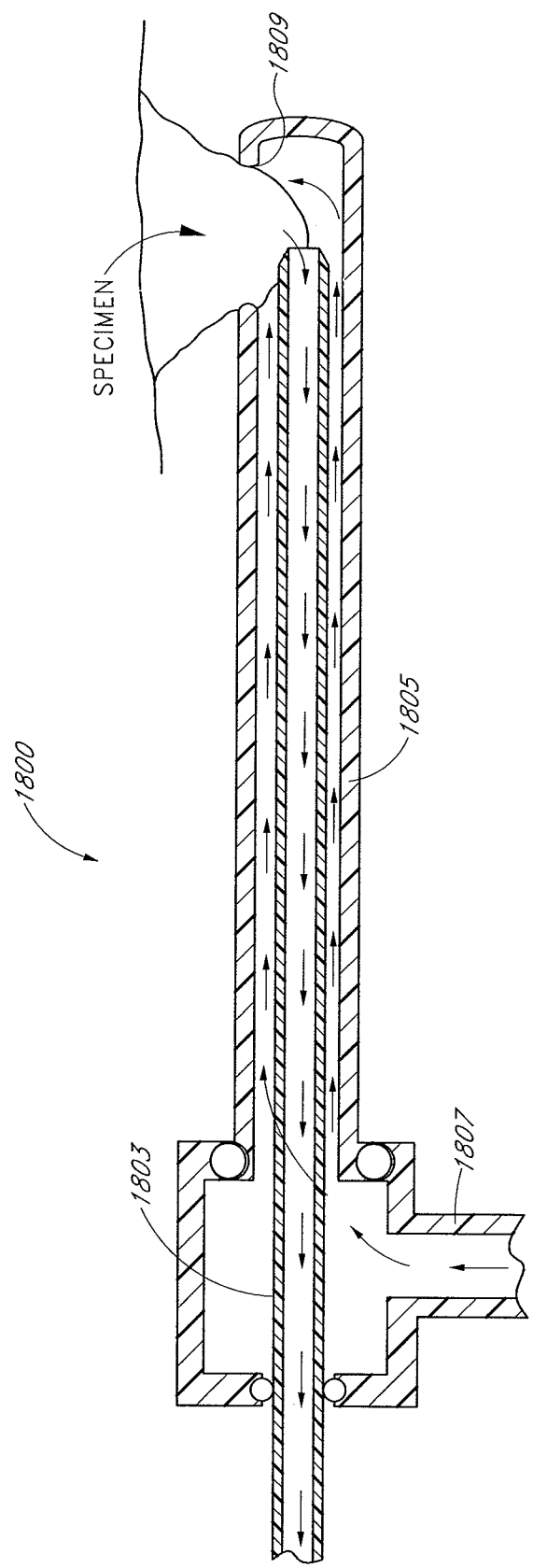
FIG. 34 is a fragmentary section view of another alternate tissue removal device that may be used in the tissue removal system of FIG. 27.

Although the present invention has been discussed above in the context of removing tissue from within a patient's uterus, it should be understood that there may be situations in which it may be desirable to remove fibroids or other tissue located on the exterior of a patient's uterus or elsewhere within a patient. In such situations, it may be desirable to access the targeted tissue by laparoscopy. Unfortunately, however, one cannot simply apply suction in this type of case to draw the tissue into the resection window of the device because the tissue would not be bathed in a liquid, but rather, would simply be surrounded by air. Therefore, according to the present invention, one approach to this problem is to deliver a suitable material to the targeted tissue, which may then be used, with the application of suction, to create a seal to promote the drawing of the targeted tissue into the resection window of the device. Referring now to FIG. 34, there is shown an embodiment of a device designed for such a purpose, the device being represented generally by reference numeral 1800. Certain aspects of device 1800 not important to an understanding of the invention are neither shown nor described herein.

Device 1800 may be similar in certain respects to device 6. One difference between the two devices is that device 1800 may comprise an inner tubular member 1803 and an outer tubular member 1805. Inner tubular member 1803 and outer tubular member 1805 may be similar to inner tubular member 77 and outer tubular member 76, respectively, of device 6, except that (i) outer tubular member 1805 may comprise a port 1807 adapted to receive a suitable liquid or gel (e.g., water, glycine, a thixotropic gel, etc.) from a supply (not shown) and (ii) inner tubular member 1803 may have an outer diameter that is about 0.005-0.006 inch less than the inner diameter of outer tubular member 1805 (as opposed to the about 0.002 inch of device 6) to permit the liquid or gel delivered to outer tubular member 1805 through port 1807 to be delivered to the targeted tissue through a resection window 1809.

Figure 35:
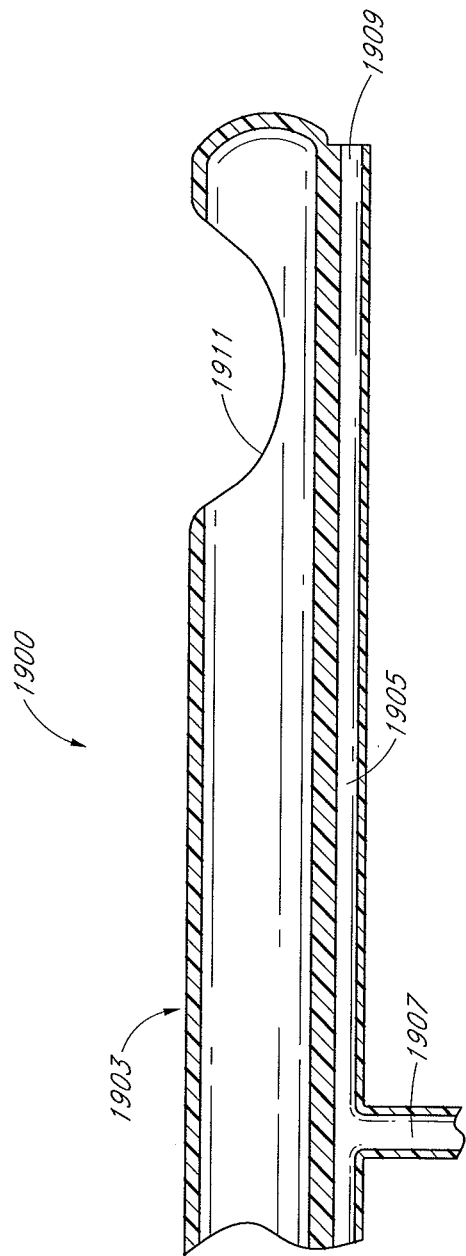
FIG. 35 is a fragmentary section view of another alternate tissue removal device that may be used in the tissue removal system of FIG. 27.

An alternate tissue removal device to device 1800 is shown in FIG. 35, said alternate tissue removal device being represented generally by reference numeral 1900. Certain aspects of device 1900 not important to an understanding of the invention are neither shown nor described herein.

Device 1900 may be similar in most respects to device 6, the principal difference between the two devices being that, whereas device 6 may comprise outer tubular member 76, device 1900 may comprise an outer tubular member 1903. Outer tubular member 1903 may be similar to outer tubular member 76, except that outer tubular member 1903 may be additionally shaped to include a channel 1905 having a proximal input port 1907 and a distal output port 1909. Input port 1907 may be adapted for connection to a supply (not shown) for receipt of a suitable liquid or gel (e.g., water, glycine, a thixotropic gel, etc.). Distal port 1909 may be positioned proximate to a resection window 1911.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A tissue removal device, comprising:
    a housing;
    an outer tube having a distal end and a proximal end, the proximal end of the outer tube supported by the housing, the outer tube configured for transcervical insertion into a uterus and having a tissue resection window located proximate to the distal end of the outer tube, the tissue resection window having a longitudinally oriented length;
    an inner tube disposed within the outer tube and configured to be translated and rotated relative to the outer tube during operation of the tissue removal device, the inner tube having an axial lumen; and
    a unitary distal tip member formed separately from the inner tube, the distal tip member being attached to a distal end of the inner tube such that an axial lumen of the distal tip member is in fluid communication with the axial lumen of the inner tube, and such that the distal tip member translates and rotates relative to the outer tube along with the inner tube during operation of the tissue removal device so that a distal facing open cutting end of the distal tip member in fluid communication with the axial lumen of the distal tip member translates across the tissue resection window of the outer tube to sever tissue extending therethrough,
    wherein the axial lumen of the distal tip member is smaller in cross-sectional area than the axial lumen of the inner tube.

2. The tissue removal device of claim 1, wherein the distal tip member is butt-welded to the inner tube.

3. The tissue removal device of claim 1, wherein an outer diameter of the distal tip member is greater than an outer diameter of the inner tube, such that an outer surface of the distal tip member acts as a bearing surface against an inner surface of the outer tube during operation of the tissue removal device.

4. The tissue removal device of claim 1, wherein the distal facing open cutting end of the distal tip member comprises an external bevel.

5. The tissue removal device of claim 4, wherein the external bevel comprises an angle of about 20 degrees.

6. The tissue removal device of claim 1, wherein the inner tube is formed of a first material and the distal tip member is formed of a second material harder than the first material.

7. The tissue removal device of claim 6, wherein the second material has a hardness that exceeds the hardness of the first material by a Rockwell C hardness of at least about 10.

8. The tissue removal device of claim 6, wherein the second material comprises a Rockwell C hardness of at least about 50.

9. The tissue removal device of claim 8, wherein an outer diameter of the distal tip member is greater than an outer diameter of the inner tube, such that an outer surface of the distal tip member acts as a bearing surface against an inner surface of the outer tube during operation of the tissue removal device.

10. The tissue removal device of claim 1, wherein the inner tube is sufficiently flexible to bend in conformity with a bend in the outer tube while rotating within the outer tube.

11. The tissue removal device of claim 1, wherein the inner tube is formed in a drawing operation and the distal tip member is formed in a milling operation.

12. The tissue removal device of claim 1, wherein the distal tip member has a length greater than a length of the tissue resection window.

13. The tissue removal device of claim 1, further comprising:
    an introducer device comprising an elongate sheath having an outer diameter of about 5.5 mm or less and comprising a first longitudinal lumen extending there through, at least a portion of the elongate sheath being configured to enter a patient's uterus through the patient's cervix;
    wherein the outer tube has an outer diameter of less than about 5.5 mm and is configured to be received within the first longitudinal lumen.

14. A tissue removal device, comprising:
    a housing;
    an outer tube having a distal end and a proximal end, the proximal end of the outer tube supported by the housing, the outer tube configured for transcervical insertion into a uterus and having a tissue resection window located proximate to the distal end of the outer tube, the tissue resection window having a longitudinally oriented length;
    an inner tube disposed within the outer tube and configured to be translated and rotated relative to the outer tube during operation of the tissue removal device, the inner tube having an axial lumen; and
    a unitary distal tip member formed separately from the inner tube, the distal tip member being attached to a distal end of the inner tube such that an axial lumen of the distal tip member is in fluid communication with the axial lumen of the inner tube, and such that the distal tip member translates and rotates relative to the outer tube along with the inner tube during operation of the tissue removal device so that a distal facing open cutting end of the distal tip member in fluid communication with the axial lumen of the distal tip member translates across the tissue resection window of the outer tube to sever tissue extending therethrough, wherein the inner tube is configured to translate and rotate relative to the outer tube during operation of the tissue removal device such that the distal tip member translates across the tissue resection window of the outer tube to sever tissue extending therethrough, and wherein the distal tip member has a length greater than a length of the tissue resection window, wherein an outer diameter of the distal tip member is greater than an outer diameter of the inner tube, such that an outer surface of the distal tip member acts as a bearing surface against an inner surface of the outer tube during operation of the tissue removal device.

15. The tissue removal device of claim 14, wherein the distal tip member is butt-welded to the inner tube.

16. The tissue removal device of claim 14, wherein the inner tube is formed of a first material and the distal tip member is formed of a second material harder than the first material.

17. The tissue removal device of claim 16, wherein the second material has a hardness that exceeds the hardness of the first material by a Rockwell C hardness of at least about 10.

18. The tissue removal device of claim 16, wherein the second material comprises a Rockwell C hardness of at least about 50.

19. The tissue removal device of claim 14, wherein the inner tube is formed in a drawing operation and the distal tip member is formed in a milling operation.

* * * * *